US011236367B2

(12) United States Patent
Beisson et al.

(10) Patent No.: US 11,236,367 B2
(45) Date of Patent: Feb. 1, 2022

(54) FATTY ACID DECARBOXYLASE AND ITS USES

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE D'AIX-MARSEILLE, Marseilles (FR)

(72) Inventors: Frederic Beisson, Aix en Provence (FR); Damien Sorigue, Manosque (FR); Bertrand Legeret, Aix en Provence (FR); Stephan Cuine, Manosque (FR); Stephanie Blangy, La Tour D'Aigues (FR); Gilles Peltier, Pierrevert (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 47 days.

(21) Appl. No.: 16/302,112

(22) PCT Filed: May 19, 2017

(86) PCT No.: PCT/EP2017/062061
§ 371 (c)(1),
(2) Date: Nov. 16, 2018

(87) PCT Pub. No.: WO2017/198802
PCT Pub. Date: Nov. 23, 2017

(65) Prior Publication Data
US 2019/0161771 A1 May 30, 2019

(30) Foreign Application Priority Data

May 20, 2016 (EP) .................................... 16305583

(51) Int. Cl.
C12N 9/88 (2006.01)
C12P 5/02 (2006.01)
C12N 9/02 (2006.01)
C07C 11/02 (2006.01)

(52) U.S. Cl.
CPC ............. *C12P 5/026* (2013.01); *C07C 11/02* (2013.01); *C12N 9/0071* (2013.01); *C12N 9/88* (2013.01); *C12P 5/02* (2013.01); *C12Y 114/14001* (2013.01); *C12Y 101/03013* (2013.01); *C12Y 101/9901* (2013.01); *C12Y 101/99018* (2013.01); *C12Y 301/02* (2013.01)

(58) Field of Classification Search
CPC ................................ C12P 7/24; C12Y 102/01
See application file for complete search history.

(56) References Cited

FOREIGN PATENT DOCUMENTS

WO WO 2014/102201 7/2014

OTHER PUBLICATIONS

Chen, B. et al. "Combinatorial metabolic engineering of *Saccharomyces cerevisiae* for terminal alkene production" *Metabolic Engineering*, Sep. 1, 2015, pp. 53-61, vol. 31.
Database UniProt [Online] Accession No. E1ZTE9, "SubName: Full=Putative uncharacterized protein {ECO:0000313 | EMBL:EFN50890.1}", Nov. 30, 2010, p. 1, XP-002761243.
Sorigué, D. et al. "Microalgae Synthesize Hydrocarbons from Long-Chain Fatty Acids via a Light-Dependent Pathway" *Plant Physiology*, Aug. 2016, pp. 2393-2405, vol. 171, Supplemental Figures. S1-S11.
Written Opinion in International Application No. PCT/EP2017/062061, dated Aug. 31, 2017, pp. 1-6.
Moulin, S. et al. "Fatty acid photodecarboxylase is an ancient photoenzyme responsible for hydrocarbon formation in the thylakoid membranes of algae" *bioRxiv*, Jun. 23, 2020, pp. 1-61.
Sorigué, D. et al. "An algal photoenzyme converts fatty acids to hydrocarbons" *Science*, Sep. 1, 2017, pp. 1-5, vol. 357.
Zhang, W. et al. "Hydrocarbon Synthesis via Photoenzymatic Decarboxylation of Carboxylic Acids" *J. Am. Chem. Soc.*, 2019, pp. 3116-3120, vol. 141.
Database UniProt [Online] Accession No. A0A248QE08, "RecName: Full=Fatty acid photodecarboxylase, chloroplastic {ECO:0000303|PubMed:28860382}", Jun. 17, 2020, pp. 1-5.
Zachos, I. et al. "Photobiocatalytic decarboxylation for olefin synthesis" *Chem. Commun.*, 2015, pp. 1918-1921, vol. 51.
Database UniProt [Online] Accession No. E1ZTE9, "SubName: Full=Putative uncharacterized protein", Nov. 30, 2010, p. 1, Version 1.
Database UniProt [Online] Accession No. E1ZTE9, "SubName: Full=Putative uncharacterized protein {ECO:0000313|EMBL:EFN50890.1}", Jan. 7, 2015, p. 1, Version 12.
Database UniProt [Online] Accession No. A8JHB7, "SubName: Full=Predicted protein {ECO:0000313|EMBL:EDO96742.1}", Apr. 13, 2016, p. 1, Version 45.
Database UniProt [Online] Accession No. R1FBM9, "SubName: Full=Choline dehydrogenase {ECO:0000313|EMBL:EOD32856.1}", Apr. 13, 2016, pp. 1-2, Version 17.

(Continued)

*Primary Examiner* — Tekchand Saidha
(74) *Attorney, Agent, or Firm* — Saliwanchik, Lloyd & Eisenschenk

(57) ABSTRACT

The present invention relates to the identification of a new class of fatty acid decarboxylases and its uses, in particular for producing alkanes/alkenes from fatty acids.

18 Claims, 15 Drawing Sheets
Specification includes a Sequence Listing.

(56) References Cited

OTHER PUBLICATIONS

Database UniProt [Online] Accession No. W7TN63, "SubName: Full=Choline dehydrogenase {ECO:0000313|EMBL:EWM27492. 1}", Apr. 13, 2016, p. 1, Version 8.
Database UniProt [Online] Accession No. R1FBM9, "SubName: Full=Choline dehydrogenase {ECO:0000313|EMBL:EOD32856. 1}", Jun. 17, 2020, pp. 1-2, Version 36.
Database UniProt [Online] Accession No. A8JHB7, "RecName: Full=Fatty acid photodecarboxylase, chloroplastic {ECO: 0000303/ PubMed ID 28860382CiteNPL}", Jun. 17, 2020, pp. 1-3, Version 68.
Database UniProt [Online] Accession No. W7TN63, "SubName: Full=Choline dehydrogenase {ECO:0000313|EMBL:EWM27492. 1}", Apr. 22, 2020, pp. 1-2, Version 20.

Chlorella (SEQ ID No 1) ; Chlamydomonas (SEQ ID No 5) ; Coccomyxa (SEQ ID No 9) ; Volvox (SEQ ID No 10) ; Ectocarpus (SEQ ID No 11); Emiliania (SEQ ID No 12); Aureococcus (SEQ ID No 13); Phaeodactylum (SEQ ID No 7); Nannochloropsis (SEQ ID No 14)

```
SEQ ID
1   ------------------------RASAVEDIRKVLSDSSSPVAGQKYDYILVGGGTAAC  36
5   ---------------------------LSVRAAAGPAGSEKFDYVLVGGGTASC  27
9   --------------------------ALRVRAIIKSDNPAADKYDFILVGGGTAGC  30
10  ---------------------------PVAVKAAASVGSEKFDYILVGGGTAGC  27
11  ----------VPAA----------R----YAT----SSVSMSVAEEGHKFIIIGGGTAGC  32
12  -----------------LRGGSGVTGGSLGRGGGSPAIDGEFDYIIVGGGAAGC  37
13  ------------------------------------------------------  0
7   --------------------------------YDYIICGGGLAGC  13
14  LSKTTIGLQSFVTANYGVRRAISLRGGLQSVS----MKAPAAVASSTYDYIIVGGGIGGC  56

1   VLANRLSADGSKRVLVLEAGPDN-TSRDVKIPAAITRLFRSP-LDWNLFSELQEQLAERQ  94
5   VLANKLSADGNKKVLVLEAGPTG-DAMEVAVPAGITRLFAHPVMDWGMSSLTQKQLVARE  86
9   VLANRLTADGSKKVLLLEAGGAN-KAREVRTPAGLPRLFKSA-LDWNLYSSLQQAASDRS  88
10  VLANKLSANGSKKVLVLEAGPTG-DAMEVAVPAGIARLFAHPVFDWGMSSLTQQQLVARE  86
11  VLANRLSADKDNSVLVLEAGSEKFNDRNIKMPIAILRLFKSV-FDWGFQSENEKFATGDG  91
12  VLANRLSADPAHRVLLIEAGGDASRDKRAQVPWAFTKLLRSE-YDWDFHVEAEAAVNQQE  96
13  -----LSEDPSKKVLVLEAGDRGPNSPLVKIPVAILKLFKSA-YDWNFATRPSEAVADRS  54
7   VLAERLSQDESKRVLVLEAGGSDYKSLFIRIPAGVLRLFRSK-YDWQHETGGEKGCNGRN  72
14  VLANRLTESGRFKVLLLEAGKSAERNPYVNIPAGVVRLFKSA-LDWQFESAPERHLDGKE  115
         *:  .     **::***          *  .. :*:     **         .

1   IYMARGRLLGGSSATNATLYHRGAAGDYDAWG----VEGWSSEDVLSWFVQAETNAD--F  148
5   IYLARGRMLGGSSGSNATLYHRGSAADYDAWG----LEGWSSKDVLDWFVKAECYAD---  139
9   IYLARGKLLGGSSATNATLYHRGTAADYDAWG----VPGWTSQDALRWFIQAENNCR--G  142
10  IYLARGRLLGGSSGTNATLYHRGTPADYDSWG----LEGWTSKDLLDWFVKAECYGD---  139
11  IYLCRGKVLGGSSCTNVMLYHRGEEADYDAWG----VDGWKGKDVLPYFKKAENNRS--K  145
12  VYLCRGKALGGSSVTNVMLYHRGSPADYDAWEEA-GARGWGAKDVLPYYLRVEDYG---D  152
13  LYVCRGKGLGGSSLTNVMLYNRGSANDYDAWAAACGDDSWGAEEMLGYFKKAEDCLVPAH  114
7   VFLQRGKILGGSSCTNVCLHHRGSAEDYNSWN----IPGWTATDVLPFFKQSQKDET--G  126
14  VYLVRGKAMGGSSAVNVMLVHRGSASDYAKWEAE-GAQGWGPEEALRYFKKMEDNLV--G  172
      :::  **:  :****    *.  * .**      **   *            .*     :  *  ::   :  :

1   GPGAYHGSGGPMRVENPRYTNKQLHTAFFKAAEEVGLTPNSDFNDWSHDHAGYGTFQVMQ  208
5   GPKPYHGTGGSMNTEQPRYEN-VLHDEFFKAAAATGLPANPDFNDWSHPQDGFGEFQVSQ  198
9   IEDGVHGTGGLMRVENPRYNN-PLHEVFFQAAKQAGLPENDNFNNWGRSQAGYGEFQVTH  201
10  GPRAFHGQSGSMNVEQPRYQN-VLHDEFFRAAAAAGLPANEDFNDWSRPQEGYGEFQVAQ  198
11  KKGEFHGKGGLMQVENARYMN-PLTKLFFKACEQAGLSENEDFNDWSHSQEGFGRFQVAQ  204
12  GASQYHAVGGHVSVQEVPYQN-QLSATFLRAMGQLGFRPNGDFNDWSSPQEGYGRYKVTQ  211
13  RANHYHGVGGPYASSHVPYTN-EMSTAFVEAAVEDGGVRNGDFNDWSTSQVGFGRFAVSQ  173
7   RDATFHGADGEWVMDEVRYQN-PLSKLFLEVGEAAGLGTNDDFNNWSHPQDGVGRFQVSE  185
14  GEGRWHGQGGMYPVDDVKYQN-PLSKRFLQACEEYGWRANPDFNDWSHPQDGYGSFKVAQ  231
         *.  *      ..  * *   :    *...      *    * :**:*.   :  * * :  * .
```

Figure 8 B

```
1   DKGTRADMYRQYLKPVLGR-RNLQVLTGAAVTKVNIDQA---AGKAQALGVEFSTDGPTG 264
5   KKGQRADTYRTYLKPAMAR-GNLKVVIGARATKVNIEKG----SSGARTTGVEYAMQ-QFG 253
9   SKGERADCFRMYLEPVMGR-SNLTVLTGAKTLKIETEKS---GGATVSRGVTFQVNGQDG 257
10  KNGERADTYRTYLKPAMGR-DNLKVMTGARTTKVHIEKS---STGPRARGVEYATQ-QFG 253
11  KRGKRCSAASSYLKEAMGR-KNLDVQTSAQITKVLI----ENGGA---IGVEYVRD-GE- 254
12  RAGRRCTAADGYLAAARER-ANLVVVTGAQATRLALDSAYDGAGRLQVSGVEFARG-DER 269
13  RKGARVDAATAYLPRKVRRRANLDVVRGAALSGVTW-------NANKATGVEFAFG-G-- 223
7   VNGERCSGATAFLSKAAKR-SNVIVRTGTMVRRIDFDET----KTAKGITYDLMGD-DTC 239
14  KHGKRVTAASGYLNKAVRRRPNLDILSEALVTRVLL----EGEGDVKAVGVEFTGK-DGK 286
     * *        :*      *   *:  :       :        :

1   ERLSAELAPGGEVIMCAGAVHTPFLLKHSGVGPSAELKEFGIPVVSNLAGVGQNLQDQPA 324
5   DRFTAELAPGGEVLMCSGAVHTPHLLMLSGVGPAATLKEHGIDVVSDLSGVGQNLQDHPA 313
9   SKHSAELAAGGEVVLCAGSIHSPQILQLSGIGPQAELRSKDIPVVADLPGVGQNMQDHPA 317
10  ERYTAELTPGGEVLMCTGAVHTPHLLMLSGIGPAPTLLEHGLDVISSLPGVGANLQDHPA 313
11  -KKIAKLAVGGEILLAGGAISSPQVLMLSGVGPAEHLRSKGIEVKSNVPGVGKNLRDHPA 313
12  EPCSVRLARGGEAVLCAGAVQTPHLLLLSGIGPAEHLREVGVPVRADLPGVGSGLQDHPA 329
13  ---VSGIACGGEVILSGGAVHSPQMLMLSGVGAKAQLEEFGIPVVADRPGVGKNLQDHPA 280
7   TTFQACLKEGGEVLVTGGAIASPQLLMCSGIGPGKHLRSLGIPVVHDNSAVGENLQDHPA 299
14  THQVRTTGKAGEVLLAGGAVNSPQLLMLSGIGPEADLQAVGIATKVNRPGVGENLQDHPA 346
      .**  ::   *:: :* :*  **:*     *     :  .   .**    ::*:**

1   CLTAAPVKEKYDGIAISDHIYNE---KGQIRKRAIASYLLGGRGGLTSTGCDRGAFVRTA- 381
5   AVLAARAKPEFEKLSVTSEVYDD---KCNIKLGAVAQYLFQRRGPLATTGCDHGAFVRTSS 371
9   CLSAFYLKESAGPISVTDELLHT---NGRIRARAILKYLLFKKGPLATTGCDHGAFVKTA- 374
10  AVLAVRAKPEFEGLSVTSEIYDS---KCNIRLGAVMKYLFGRRGPLATTGCDHGAFVRTSA 371
11  VTVMADI-NKPI---SITDKVLKEG-SGDVNKITALQWLLTGTGPLTSPGCENGAFFKTTP 369
12  VVVSYES-KKAV--AATDDALLKGYASLVNPLAMLRWLLFGRGPLACAACDHGGFVRSSP 386
13  CLVSWRGSAKAQGKSHSTQLRIPG-TTKTSPKALLQWLFLGRGPLASPGCDHGGFAKVGA 339
7   AVVSFKTPQKGV--SVTSKLRLFG---KTNPIPVFQWLFFKSGLLTSTGCDHGAFVRTSD 354
14  VTIAHNI-TRPI--SLCDDLFLFH-TPVPKPHQVLRWTLTGSGPLTTPGCDHGAFLKTRE 402
                    :    .                :  :    * *:  .*:.*.* :

1   GQALPDLQVRFVPGMALDPDGVSTYVR-FAKFQSQGLKWPSGITMQLIACRPQST-GSVG 439
5   SLSQPDLQMRFVPGCALDPDGVKSYIV-FGELKKQGRAWPGGITLQLLAIRAKSK-GSIG 429
9   GQSEPDLQIRFVPGLALDPDGIGSYTA-FGKMKD--QKWPSGITFQLLGVRPKSR-GSVG 430
10  SHSQPDLQMRFVPGCALDPDGVKSYIV-FGELKKQGRAWPGGITLQLLGIRAKSR-GSIG 429
11  DKAAADLQLRFVPGRSTTPDGVKAYNT-IGTKG----RPPSGVTVQVVGIRPQSE-GHVE 423
12  DLDQPDVQIRFVPARASSASGMNTLIE-LGRRA----RFLPGFSTQVVACRPRSE-GRVR 440
13  GDGDCDVQFRFLATKSITPDGMSTISDSYEAAV----DHPDGLTIQTIVARPKSRAGEVK 395
7   SLEQPDLQIRFLAARALGPDGMTTYTK-FRTMK----TVEDGYSFQSVACRAKSK-GRIR 408
14  DLQEPNVQFRFIAGRGSDPDGVRSYI--MGGSA----RPLSGLTLQVVNIRPKSK-GKLT 455
      ::*.**:    .   .*: :             *  :  *   *  :*   * :

1   LKSADPFAPPKLSPGYLTDKDGADLATLRKGIHWARDVARSSALSEYLDGELFPGSGVVS 499
5   LKAADPFINPAININYFSDP--ADLATLVNAVKMARKIAAQEPLKKYLQEETFPGERASS 487
9   LRSDDPWDAPKLDIGFLTDKEGADLATLRSGIKLSREIAAEPAFGAYVGNELHPGAAASS 490
10  LKAADPFINPAININYFSDP--EDLATLKNGVRIAREIVAQEPLRKYLLEETFPGERANT 487
11  LRSSDPFDKPHIVTNYLESG--EDMASLTNGIEMARKLFDQEAFGEMVDKEVFPGRD--- 478
12  LRSADPFAKPIIEGIHLGAA--EDVASLRHGIRLGRQVCAAAAFDEYRGEEVFPGAAVQS 498
13  LASRDPAAKPVIENAYLSDE--ADVMTMVKALQKARSIASRAPLSAYAGHEEFPGEDVAD 453
7   LSSSNSHVKPMIDGGYLSNQ--DDLATLRAGIKLGRMLGNRPEWGEYLGQEVYPGPDVQT 466
14  LASKDPLKKPRIEVRYLSAA--EDLQALRTGMRIGRDLIKQRAFADILDEEVFPGPAAQT 513
     * :     *  *   .:    *: ::   .:. .* :         * .**
```

Figure 8 B (following)

```
1  DDQIDEYIRRSIHSSNAITGTCKMGNAGDSSSVV-DNQLRVHGVEGLRVVDASVVPKIPG 558
5  DKDLEEYIRRTVHSGNALVGTAAMGASPAAGAVVSSADLKVFGVEGLRVVDASVLPRIPG 547
9  DSAIDSFIRDTVHSGNANVGTCSMGVNGN--AVV-DPSLRVFGIRGLRVADASVIPVIPG 547
10 DKDIEEYVRRTVHSGNALVGTCAMGTTPASGAVVSSADLKVFGVDGLRVVDASVLPRIPG 547
11 NKEISEYIKSTVHSANALVGTCKMGEESDNMSVV-NSALKVKGVAGLRVIDSSVMPSIPG 537
12 DEQIDEYIRSSVHSANALTSSCRMGDPSDPAAVL-DSHLRVRGVGGLRVADASAMPRIIG 557
13 ERQLAAYVRNTAHTANAVVGTCKMGESSDALAVV-DNHLKVIGVSNLRVVDASVMPTLPG 512
7  DEEIDEYIRNSLHTANALTGTCKMGTG--RGAVV-GPDLRVIGVNGVRVGDSSVFPCIPG 523
14 DEELDAYIRDSLHTANALVGTCKMGSVEDRNAVV-DPECRVIGVGGLRVVDASVMPVIPG 572
       :  :   ::: : *:.**  ..:. **         :*:      :* *: :** *:*..* : *

1  GQTGAPVVMIAERAAALLTGKATIGASAAAPATV-------AA-------------------- 594
5  GQTGAATVMVAERAAALLRGQATIAPSRQPVAV---------------------------- 580
9  GQTGAATVMVAERAAEILLGSNQKQPAAAVPAAQ-------PALA---------------- 585
10 GQTGAATVMVAERAAAMLLGQATITSRREPAAV---------------------------- 580
11 GQTAAPTIMIAEKAADMLMA---------------------------------------- 557
12 GQTQAPTYMLAERAADILLHARLQAHEPATESVSQRLEVAAAAL---------------- 601
13 GQTAASTVALAEKAADLIKGG--------------------------------------- 533
7  GQTATPTVMIGDRAAVFVRQPVSQLNIE---IFREKGGTHPGATTASA------------ 568
14 GQTGSGTTMLAEKAADLVRAHAGDLVEMGVQDEERKGGWFNGLLGRKQKVATEKERGERG 632
   *** :  .   :.::** ::
```

Figure 8 B (following)

SEQUENCE LISTING

<160> NUMBER OF SEQ ID NOS: 32

<210> SEQ ID NO 1
<211> LENGTH: 594
<212> TYPE: PRT
<213> ORGANISM: Chlorella variabilis

<400> SEQUENCE: 1

Arg Ala Ser Ala Val Glu Asp Ile Arg Lys Val Leu Ser Asp Ser Ser
1               5                   10                  15

Ser Pro Val Ala Gly Gln Lys Tyr Asp Tyr Ile Leu Val Gly Gly Gly

```
            20                  25                  30
Thr Ala Ala Cys Val Leu Ala Asn Arg Leu Ser Ala Asp Gly Ser Lys
            35                  40                  45

Arg Val Leu Val Leu Glu Ala Gly Pro Asp Asn Thr Ser Arg Asp Val
            50                  55                  60

Lys Ile Pro Ala Ala Ile Thr Arg Leu Phe Arg Ser Pro Leu Asp Trp
 65                 70                  75                  80

Asn Leu Phe Ser Glu Leu Gln Glu Gln Leu Ala Glu Arg Gln Ile Tyr
                85                  90                  95

Met Ala Arg Gly Arg Leu Leu Gly Gly Ser Ala Thr Asn Ala Thr
               100                 105                 110

Leu Tyr His Arg Gly Ala Ala Gly Asp Tyr Asp Ala Trp Gly Val Glu
               115                 120                 125

Gly Trp Ser Ser Glu Asp Val Leu Ser Trp Phe Val Gln Ala Glu Thr
               130                 135                 140

Asn Ala Asp Phe Gly Pro Gly Ala Tyr His Gly Ser Gly Gly Pro Met
145                 150                 155                 160

Arg Val Glu Asn Pro Arg Tyr Thr Asn Lys Gln Leu His Thr Ala Phe
               165                 170                 175

Phe Lys Ala Ala Glu Glu Val Gly Leu Thr Pro Asn Ser Asp Phe Asn
               180                 185                 190

Asp Trp Ser His Asp His Ala Gly Tyr Gly Thr Phe Gln Val Met Gln
               195                 200                 205

Asp Lys Gly Thr Arg Ala Asp Met Tyr Arg Gln Tyr Leu Lys Pro Val
               210                 215                 220

Leu Gly Arg Arg Asn Leu Gln Val Leu Thr Gly Ala Ala Val Thr Lys
225                 230                 235                 240

Val Asn Ile Asp Gln Ala Ala Gly Lys Ala Gln Ala Leu Gly Val Glu
               245                 250                 255

Phe Ser Thr Asp Gly Pro Thr Gly Glu Arg Leu Ser Ala Glu Leu Ala
               260                 265                 270

Pro Gly Gly Glu Val Ile Met Cys Ala Gly Ala Val His Thr Pro Phe
               275                 280                 285

Leu Leu Lys His Ser Gly Val Gly Pro Ser Ala Glu Leu Lys Glu Phe
               290                 295                 300

Gly Ile Pro Val Val Ser Asn Leu Ala Gly Val Gly Gln Asn Leu Gln
305                 310                 315                 320

Asp Gln Pro Ala Cys Leu Thr Ala Ala Pro Val Lys Glu Lys Tyr Asp
               325                 330                 335

Gly Ile Ala Ile Ser Asp His Ile Tyr Asn Glu Lys Gly Gln Ile Arg
               340                 345                 350

Lys Arg Ala Ile Ala Ser Tyr Leu Gly Gly Arg Gly Gly Leu Thr
               355                 360                 365

Ser Thr Gly Cys Asp Arg Gly Ala Phe Val Arg Thr Ala Gly Gln Ala
               370                 375                 380

Leu Pro Asp Leu Gln Val Arg Phe Val Pro Gly Met Ala Leu Asp Pro
385                 390                 395                 400

Asp Gly Val Ser Thr Tyr Val Arg Phe Ala Lys Phe Gln Ser Gln Gly
               405                 410                 415

Leu Lys Trp Pro Ser Gly Ile Thr Met Gln Leu Ile Ala Cys Arg Pro
               420                 425                 430

Gln Ser Thr Gly Ser Val Gly Leu Lys Ser Ala Asp Pro Phe Ala Pro
               435                 440                 445
```

```
Pro Lys Leu Ser Pro Gly Tyr Leu Thr Asp Lys Asp Gly Ala Asp Leu
    450                 455                 460

Ala Thr Leu Arg Lys Gly Ile His Trp Ala Arg Asp Val Ala Arg Ser
465                 470                 475                 480

Ser Ala Leu Ser Glu Tyr Leu Asp Gly Glu Leu Phe Pro Gly Ser Gly
                485                 490                 495

Val Val Ser Asp Asp Gln Ile Asp Glu Tyr Ile Arg Arg Ser Ile His
            500                 505                 510

Ser Ser Asn Ala Ile Thr Gly Thr Cys Lys Met Gly Asn Ala Gly Asp
        515                 520                 525

Ser Ser Ser Val Val Asp Asn Gln Leu Arg Val His Gly Val Glu Gly
    530                 535                 540

Leu Arg Val Val Asp Ala Ser Val Val Pro Lys Ile Pro Gly Gly Gln
545                 550                 555                 560

Thr Gly Ala Pro Val Val Met Ile Ala Glu Arg Ala Ala Ala Leu Leu
                565                 570                 575

Thr Gly Lys Ala Thr Ile Gly Ala Ser Ala Ala Pro Ala Thr Val
        580                 585                 590

Ala Ala

<210> SEQ ID NO 2
<211> LENGTH: 654
<212> TYPE: PRT
<213> ORGANISM: Chlorella variabilis

<400> SEQUENCE: 2

Met Ala Ser Ile Thr Ser Arg Ala Ser Ala Arg Ala Ser Cys Ser Gln
1               5                   10                  15

Ala Asn Thr Arg Ala Gly Arg Val Ala Leu Ser Gly Gly Ala Leu Leu
            20                  25                  30

Arg Pro Ala Arg Pro Ala Arg Ser Phe Val Pro Ala Arg Lys Gln Gln
        35                  40                  45

Gln Gly Ala Val Arg Arg Gly Gly Ala Leu Ser Ala Arg Ala Ser Ala
    50                  55                  60

Val Glu Asp Ile Arg Lys Val Leu Ser Asp Ser Ser Ser Pro Val Ala
65                  70                  75                  80

Gly Gln Lys Tyr Asp Tyr Ile Leu Val Gly Gly Gly Thr Ala Ala Cys
                85                  90                  95

Val Leu Ala Asn Arg Leu Ser Ala Asp Gly Ser Lys Arg Val Leu Val
            100                 105                 110

Leu Glu Ala Gly Pro Asp Asn Thr Ser Arg Asp Val Lys Ile Pro Ala
        115                 120                 125

Ala Ile Thr Arg Leu Phe Arg Ser Pro Leu Asp Trp Asn Leu Phe Ser
    130                 135                 140

Glu Leu Gln Glu Gln Leu Ala Glu Arg Gln Ile Tyr Met Ala Arg Gly
145                 150                 155                 160

Arg Leu Leu Gly Gly Ser Ser Ala Thr Asn Ala Thr Leu Tyr His Arg
                165                 170                 175

Gly Ala Ala Gly Asp Tyr Asp Ala Trp Gly Val Glu Gly Trp Ser Ser
            180                 185                 190

Glu Asp Val Leu Ser Trp Phe Val Gln Ala Glu Thr Asn Ala Asp Phe
        195                 200                 205

Gly Pro Gly Ala Tyr His Gly Ser Gly Gly Pro Met Arg Val Glu Asn
    210                 215                 220
```

```
Pro Arg Tyr Thr Asn Lys Gln Leu His Thr Ala Phe Phe Lys Ala Ala
225                 230                 235                 240

Glu Glu Val Gly Leu Thr Pro Asn Ser Asp Phe Asn Asp Trp Ser His
            245                 250                 255

Asp His Ala Gly Tyr Gly Thr Phe Gln Val Met Gln Asp Lys Gly Thr
            260                 265                 270

Arg Ala Asp Met Tyr Arg Gln Tyr Leu Lys Pro Val Leu Gly Arg Arg
            275                 280                 285

Asn Leu Gln Val Leu Thr Gly Ala Ala Val Thr Lys Val Asn Ile Asp
            290                 295                 300

Gln Ala Ala Gly Lys Ala Gln Ala Leu Gly Val Glu Phe Ser Thr Asp
305                 310                 315                 320

Gly Pro Thr Gly Glu Arg Leu Ser Ala Glu Leu Ala Pro Gly Gly Glu
            325                 330                 335

Val Ile Met Cys Ala Gly Ala Val His Thr Pro Phe Leu Leu Lys His
            340                 345                 350

Ser Gly Val Gly Pro Ser Ala Glu Leu Lys Glu Phe Gly Ile Pro Val
            355                 360                 365

Val Ser Asn Leu Ala Gly Val Gly Gln Asn Leu Gln Asp Gln Pro Ala
            370                 375                 380

Cys Leu Thr Ala Ala Pro Val Lys Glu Lys Tyr Asp Gly Ile Ala Ile
385                 390                 395                 400

Ser Asp His Ile Tyr Asn Glu Lys Gly Gln Ile Arg Lys Arg Ala Ile
            405                 410                 415

Ala Ser Tyr Leu Leu Gly Arg Gly Leu Thr Ser Thr Gly Cys
            420                 425                 430

Asp Arg Gly Ala Phe Val Arg Thr Ala Gly Gln Ala Leu Pro Asp Leu
            435                 440                 445

Gln Val Arg Phe Val Pro Gly Met Ala Leu Asp Pro Asp Gly Val Ser
            450                 455                 460

Thr Tyr Val Arg Phe Ala Lys Phe Gln Ser Gln Gly Leu Lys Trp Pro
465                 470                 475                 480

Ser Gly Ile Thr Met Gln Leu Ile Ala Cys Arg Pro Gln Ser Thr Gly
            485                 490                 495

Ser Val Gly Leu Lys Ser Ala Asp Pro Phe Ala Pro Lys Leu Ser
            500                 505                 510

Pro Gly Tyr Leu Thr Asp Lys Asp Gly Ala Asp Leu Ala Thr Leu Arg
            515                 520                 525

Lys Gly Ile His Trp Ala Arg Asp Val Ala Arg Ser Ser Ala Leu Ser
            530                 535                 540

Glu Tyr Leu Asp Gly Glu Leu Phe Pro Gly Ser Gly Val Val Ser Asp
545                 550                 555                 560

Asp Gln Ile Asp Glu Tyr Ile Arg Arg Ser Ile His Ser Ser Asn Ala
            565                 570                 575

Ile Thr Gly Thr Cys Lys Met Gly Asn Ala Gly Asp Ser Ser Ser Val
            580                 585                 590

Val Asp Asn Gln Leu Arg Val His Gly Val Glu Gly Leu Arg Val Val
            595                 600                 605

Asp Ala Ser Val Val Pro Lys Ile Pro Gly Gly Gln Thr Gly Ala Pro
            610                 615                 620

Val Val Met Ile Ala Glu Arg Ala Ala Ala Leu Leu Thr Gly Lys Ala
625                 630                 635                 640
```

```
Thr Ile Gly Ala Ser Ala Ala Pro Ala Thr Val Ala Ala
            645                 650
```

<210> SEQ ID NO 3
<211> LENGTH: 729
<212> TYPE: PRT
<213> ORGANISM: artificial sequence
<220> FEATURE:
<223> OTHER INFORMATION: shGMC

<400> SEQUENCE: 3

```
Met Gly His His His His His Ser Asp Lys Ile Ile His Leu Thr
1               5                   10                  15

Asp Asp Ser Phe Asp Thr Asp Val Leu Lys Ala Asp Gly Ala Ile Leu
            20                  25                  30

Val Asp Phe Trp Ala Glu Trp Cys Gly Pro Cys Lys Met Ile Ala Pro
        35                  40                  45

Ile Leu Asp Glu Ile Ala Asp Glu Tyr Gln Gly Lys Leu Thr Val Ala
    50                  55                  60

Lys Leu Asn Ile Asp Gln Asn Pro Gly Thr Ala Pro Lys Tyr Gly Ile
65                  70                  75                  80

Arg Gly Ile Pro Thr Leu Leu Leu Phe Lys Asn Gly Glu Val Ala Ala
                85                  90                  95

Thr Lys Val Gly Ala Leu Ser Lys Gly Gln Leu Lys Glu Phe Leu Asp
            100                 105                 110

Ala Asn Leu Ala Gly Ser Gly Ser Gly Val Ser Gly Val Asp Leu Gly
        115                 120                 125

Thr Glu Asn Leu Tyr Phe Gln Ser Ala Ser Ala Val Glu Asp Ile Arg
    130                 135                 140

Lys Val Leu Ser Asp Ser Ser Pro Val Ala Gly Gln Lys Tyr Asp
145                 150                 155                 160

Tyr Ile Leu Val Gly Gly Gly Thr Ala Ala Cys Val Leu Ala Asn Arg
                165                 170                 175

Leu Ser Ala Asp Gly Ser Lys Arg Val Leu Val Leu Glu Ala Gly Pro
            180                 185                 190

Asp Asn Thr Ser Arg Asp Val Lys Ile Pro Ala Ala Ile Thr Arg Leu
        195                 200                 205

Phe Arg Ser Pro Leu Asp Trp Asn Leu Phe Ser Glu Leu Gln Glu Gln
    210                 215                 220

Leu Ala Glu Arg Gln Ile Tyr Met Ala Arg Gly Arg Leu Leu Gly Gly
225                 230                 235                 240

Ser Ser Ala Thr Asn Ala Thr Leu Tyr His Arg Gly Ala Ala Gly Asp
                245                 250                 255

Tyr Asp Ala Trp Gly Val Glu Gly Trp Ser Ser Glu Asp Val Leu Ser
            260                 265                 270

Trp Phe Val Gln Ala Glu Thr Asn Ala Asp Phe Gly Pro Gly Ala Tyr
        275                 280                 285

His Gly Ser Gly Gly Pro Met Arg Val Glu Asn Pro Arg Tyr Thr Asn
    290                 295                 300

Lys Gln Leu His Thr Ala Phe Phe Lys Ala Ala Glu Glu Val Gly Leu
305                 310                 315                 320

Thr Pro Asn Ser Asp Phe Asn Asp Trp Ser His Asp His Ala Gly Tyr
                325                 330                 335

Gly Thr Phe Gln Val Met Gln Asp Lys Gly Thr Arg Ala Asp Met Tyr
            340                 345                 350
```

```
Arg Gln Tyr Leu Lys Pro Val Leu Gly Arg Arg Asn Leu Gln Val Leu
            355                 360                 365

Thr Gly Ala Ala Val Thr Lys Val Asn Ile Asp Gln Ala Ala Gly Lys
370                 375                 380

Ala Gln Ala Leu Gly Val Glu Phe Ser Thr Asp Gly Pro Thr Gly Glu
385                 390                 395                 400

Arg Leu Ser Ala Glu Leu Ala Pro Gly Gly Glu Val Ile Met Cys Ala
                405                 410                 415

Gly Ala Val His Thr Pro Phe Leu Leu Lys His Ser Gly Val Gly Pro
            420                 425                 430

Ser Ala Glu Leu Lys Glu Phe Gly Ile Pro Val Val Ser Asn Leu Ala
435                 440                 445

Gly Val Gly Gln Asn Leu Gln Asp Gln Pro Ala Cys Leu Thr Ala Ala
450                 455                 460

Pro Val Lys Glu Lys Tyr Asp Gly Ile Ala Ile Ser Asp His Ile Tyr
465                 470                 475                 480

Asn Glu Lys Gly Gln Ile Arg Lys Arg Ala Ile Ala Ser Tyr Leu Leu
                485                 490                 495

Gly Gly Arg Gly Gly Leu Thr Ser Thr Gly Cys Asp Arg Gly Ala Phe
            500                 505                 510

Val Arg Thr Ala Gly Gln Ala Leu Pro Asp Leu Gln Val Arg Phe Val
            515                 520                 525

Pro Gly Met Ala Leu Asp Pro Asp Gly Val Ser Thr Tyr Val Arg Phe
            530                 535                 540

Ala Lys Phe Gln Ser Gln Gly Leu Lys Trp Pro Ser Gly Ile Thr Met
545                 550                 555                 560

Gln Leu Ile Ala Cys Arg Pro Gln Ser Thr Gly Ser Val Gly Leu Lys
                565                 570                 575

Ser Ala Asp Pro Phe Ala Pro Pro Lys Leu Ser Pro Gly Tyr Leu Thr
            580                 585                 590

Asp Lys Asp Gly Ala Asp Leu Ala Thr Leu Arg Lys Gly Ile His Trp
            595                 600                 605

Ala Arg Asp Val Ala Arg Ser Ser Ala Leu Ser Glu Tyr Leu Asp Gly
610                 615                 620

Glu Leu Phe Pro Gly Ser Gly Val Val Ser Asp Asp Gln Ile Asp Glu
625                 630                 635                 640

Tyr Ile Arg Arg Ser Ile His Ser Ser Asn Ala Ile Thr Gly Thr Cys
                645                 650                 655

Lys Met Gly Asn Ala Gly Asp Ser Ser Ser Val Val Asp Asn Gln Leu
            660                 665                 670

Arg Val His Gly Val Glu Gly Leu Arg Val Val Asp Ala Ser Val Val
            675                 680                 685

Pro Lys Ile Pro Gly Gly Gln Thr Gly Ala Pro Val Val Met Ile Ala
690                 695                 700

Glu Arg Ala Ala Ala Leu Leu Thr Gly Lys Ala Thr Ile Gly Ala Ser
705                 710                 715                 720

Ala Ala Ala Pro Ala Thr Val Ala Ala
                725

<210> SEQ ID NO 4
<211> LENGTH: 15
<212> TYPE: PRT
<213> ORGANISM: artificial sequence
<220> FEATURE:
<223> OTHER INFORMATION: Consensus sequence
```

-continued

```
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (4)..(7)
<223> OTHER INFORMATION: X is any amino acid
<220> FEATURE:
<221> NAME/KEY: MISC_FEATURE
<222> LOCATION: (9)..(9)
<223> OTHER INFORMATION: X is D or E
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (12)..(12)
<223> OTHER INFORMATION: X is A or G
<220> FEATURE:
<221> NAME/KEY: MISC_FEATURE
<222> LOCATION: (14)..(14)
<223> OTHER INFORMATION: X is any amino acid
<220> FEATURE:
<221> NAME/KEY: MISC_FEATURE
<222> LOCATION: (15)..(15)
<223> OTHER INFORMATION: X is K or R

<400> SEQUENCE: 4

Gly Xaa Leu Xaa Xaa Xaa Xaa Cys Xaa Xaa Gly Xaa Phe Xaa Xaa
1               5                   10                  15

<210> SEQ ID NO 5
<211> LENGTH: 580
<212> TYPE: PRT
<213> ORGANISM: Chlamydomonas reinhardtii

<400> SEQUENCE: 5

Leu Ser Val Arg Ala Ala Ala Gly Pro Ala Gly Ser Glu Lys Phe Asp
1               5                   10                  15

Tyr Val Leu Val Gly Gly Gly Thr Ala Ser Cys Val Leu Ala Asn Lys
                20                  25                  30

Leu Ser Ala Asp Gly Asn Lys Lys Val Leu Val Leu Glu Ala Gly Pro
            35                  40                  45

Thr Gly Asp Ala Met Glu Val Ala Val Pro Ala Gly Ile Thr Arg Leu
        50                  55                  60

Phe Ala His Pro Val Met Asp Trp Gly Met Ser Ser Leu Thr Gln Lys
65                  70                  75                  80

Gln Leu Val Ala Arg Glu Ile Tyr Leu Ala Arg Gly Arg Met Leu Gly
                85                  90                  95

Gly Ser Ser Gly Ser Asn Ala Thr Leu Tyr His Arg Gly Ser Ala Ala
            100                 105                 110

Asp Tyr Asp Ala Trp Gly Leu Glu Gly Trp Ser Ser Lys Asp Val Leu
        115                 120                 125

Asp Trp Phe Val Lys Ala Glu Cys Tyr Ala Asp Gly Pro Lys Pro Tyr
    130                 135                 140

His Gly Thr Gly Gly Ser Met Asn Thr Glu Gln Pro Arg Tyr Glu Asn
145                 150                 155                 160

Val Leu His Asp Glu Phe Phe Lys Ala Ala Ala Thr Gly Leu Pro
                165                 170                 175

Ala Asn Pro Asp Phe Asn Asp Trp Ser His Pro Gln Asp Gly Phe Gly
            180                 185                 190

Glu Phe Gln Val Ser Gln Lys Lys Gly Gln Arg Ala Asp Thr Tyr Arg
```

```
                195                 200                 205
Thr Tyr Leu Lys Pro Ala Met Ala Arg Gly Asn Leu Lys Val Val Ile
210                 215                 220
Gly Ala Arg Ala Thr Lys Val Asn Ile Glu Lys Gly Ser Ser Gly Ala
225                 230                 235                 240
Arg Thr Thr Gly Val Glu Tyr Ala Met Gln Gln Phe Gly Asp Arg Phe
                245                 250                 255
Thr Ala Glu Leu Ala Pro Gly Gly Glu Val Leu Met Cys Ser Gly Ala
            260                 265                 270
Val His Thr Pro His Leu Leu Met Leu Ser Gly Val Gly Pro Ala Ala
            275                 280                 285
Thr Leu Lys Glu His Gly Ile Asp Val Val Ser Asp Leu Ser Gly Val
290                 295                 300
Gly Gln Asn Leu Gln Asp His Pro Ala Ala Val Leu Ala Ala Arg Ala
305                 310                 315                 320
Lys Pro Glu Phe Glu Lys Leu Ser Val Thr Ser Glu Val Tyr Asp Asp
                325                 330                 335
Lys Cys Asn Ile Lys Leu Gly Ala Val Ala Gln Tyr Leu Phe Gln Arg
            340                 345                 350
Arg Gly Pro Leu Ala Thr Thr Gly Cys Asp His Gly Ala Phe Val Arg
            355                 360                 365
Thr Ser Ser Ser Leu Ser Gln Pro Asp Leu Gln Met Arg Phe Val Pro
370                 375                 380
Gly Cys Ala Leu Asp Pro Asp Gly Val Lys Ser Tyr Ile Val Phe Gly
385                 390                 395                 400
Glu Leu Lys Lys Gln Gly Arg Ala Trp Pro Gly Gly Ile Thr Leu Gln
                405                 410                 415
Leu Leu Ala Ile Arg Ala Lys Ser Lys Gly Ser Ile Gly Leu Lys Ala
            420                 425                 430
Ala Asp Pro Phe Ile Asn Pro Ala Ile Asn Ile Asn Tyr Phe Ser Asp
            435                 440                 445
Pro Ala Asp Leu Ala Thr Leu Val Asn Ala Val Lys Met Ala Arg Lys
450                 455                 460
Ile Ala Ala Gln Glu Pro Leu Lys Lys Tyr Leu Gln Glu Glu Thr Phe
465                 470                 475                 480
Pro Gly Glu Arg Ala Ser Ser Asp Lys Asp Leu Glu Glu Tyr Ile Arg
                485                 490                 495
Arg Thr Val His Ser Gly Asn Ala Leu Val Gly Thr Ala Ala Met Gly
            500                 505                 510
Ala Ser Pro Ala Ala Gly Ala Val Val Ser Ser Ala Asp Leu Lys Val
            515                 520                 525
Phe Gly Val Glu Gly Leu Arg Val Val Asp Ala Ser Val Leu Pro Arg
            530                 535                 540
Ile Pro Gly Gly Gln Thr Gly Ala Ala Thr Val Met Val Ala Glu Arg
545                 550                 555                 560
Ala Ala Ala Leu Leu Arg Gly Gln Ala Thr Ile Ala Pro Ser Arg Gln
                565                 570                 575
Pro Val Ala Val
            580

<210> SEQ ID NO 6
<211> LENGTH: 611
<212> TYPE: PRT
<213> ORGANISM: Chlamydomonas reinhardtii
```

<400> SEQUENCE: 6

```
Met Met Leu Gly Pro Lys Thr Val Thr Arg Gly Ala Thr Lys Gly Ala
1               5                   10                  15

Ala Pro Arg Ser Met Ala Ala Arg Arg Val Gly Gly Ala Arg Arg Leu
                20                  25                  30

Ser Val Arg Ala Ala Ala Gly Pro Ala Gly Ser Glu Lys Phe Asp Tyr
            35                  40                  45

Val Leu Val Gly Gly Thr Ala Ser Cys Val Leu Ala Asn Lys Leu
    50                  55                  60

Ser Ala Asp Gly Asn Lys Lys Val Leu Val Leu Glu Ala Gly Pro Thr
65                  70                  75                  80

Gly Asp Ala Met Glu Val Ala Val Pro Ala Gly Ile Thr Arg Leu Phe
                85                  90                  95

Ala His Pro Val Met Asp Trp Gly Met Ser Ser Leu Thr Gln Lys Gln
                100                 105                 110

Leu Val Ala Arg Glu Ile Tyr Leu Ala Arg Gly Arg Met Leu Gly Gly
            115                 120                 125

Ser Ser Gly Ser Asn Ala Thr Leu Tyr His Arg Gly Ser Ala Ala Asp
130                 135                 140

Tyr Asp Ala Trp Gly Leu Glu Gly Trp Ser Ser Lys Asp Val Leu Asp
145                 150                 155                 160

Trp Phe Val Lys Ala Glu Cys Tyr Ala Asp Gly Pro Lys Pro Tyr His
                165                 170                 175

Gly Thr Gly Gly Ser Met Asn Thr Glu Gln Pro Arg Tyr Glu Asn Val
                180                 185                 190

Leu His Asp Glu Phe Phe Lys Ala Ala Ala Thr Gly Leu Pro Ala
            195                 200                 205

Asn Pro Asp Phe Asn Asp Trp Ser His Pro Gln Asp Gly Phe Gly Glu
    210                 215                 220

Phe Gln Val Ser Gln Lys Lys Gly Gln Arg Ala Asp Thr Tyr Arg Thr
225                 230                 235                 240

Tyr Leu Lys Pro Ala Met Ala Arg Gly Asn Leu Lys Val Val Ile Gly
                245                 250                 255

Ala Arg Ala Thr Lys Val Asn Ile Glu Lys Gly Ser Ser Gly Ala Arg
            260                 265                 270

Thr Thr Gly Val Glu Tyr Ala Met Gln Gln Phe Gly Asp Arg Phe Thr
            275                 280                 285

Ala Glu Leu Ala Pro Gly Gly Glu Val Leu Met Cys Ser Gly Ala Val
    290                 295                 300

His Thr Pro His Leu Leu Met Leu Ser Gly Val Gly Pro Ala Ala Thr
305                 310                 315                 320

Leu Lys Glu His Gly Ile Asp Val Val Ser Asp Leu Ser Gly Val Gly
                325                 330                 335

Gln Asn Leu Gln Asp His Pro Ala Ala Val Leu Ala Ala Arg Ala Lys
            340                 345                 350

Pro Glu Phe Glu Lys Leu Ser Val Thr Ser Glu Val Tyr Asp Asp Lys
            355                 360                 365

Cys Asn Ile Lys Leu Gly Ala Val Ala Gln Tyr Leu Phe Gln Arg Arg
        370                 375                 380

Gly Pro Leu Ala Thr Thr Gly Cys Asp His Gly Ala Phe Val Arg Thr
385                 390                 395                 400

Ser Ser Ser Leu Ser Gln Pro Asp Leu Gln Met Arg Phe Val Pro Gly
```

```
                    405                 410                 415
Cys Ala Leu Asp Pro Asp Gly Val Lys Ser Tyr Ile Val Phe Gly Glu
                420                 425                 430

Leu Lys Lys Gln Gly Arg Ala Trp Pro Gly Gly Ile Thr Leu Gln Leu
            435                 440                 445

Leu Ala Ile Arg Ala Lys Ser Lys Gly Ser Ile Gly Leu Lys Ala Ala
        450                 455                 460

Asp Pro Phe Ile Asn Pro Ala Ile Asn Ile Asn Tyr Phe Ser Asp Pro
465                 470                 475                 480

Ala Asp Leu Ala Thr Leu Val Asn Ala Val Lys Met Ala Arg Lys Ile
                485                 490                 495

Ala Ala Gln Glu Pro Leu Lys Lys Tyr Leu Gln Glu Thr Phe Pro
            500                 505                 510

Gly Glu Arg Ala Ser Ser Asp Lys Asp Leu Glu Tyr Ile Arg Arg
        515                 520                 525

Thr Val His Ser Gly Asn Ala Leu Val Gly Thr Ala Ala Met Gly Ala
        530                 535                 540

Ser Pro Ala Ala Gly Ala Val Val Ser Ser Ala Asp Leu Lys Val Phe
545                 550                 555                 560

Gly Val Glu Gly Leu Arg Val Val Asp Ala Ser Val Leu Pro Arg Ile
                565                 570                 575

Pro Gly Gly Gln Thr Gly Ala Ala Thr Val Met Val Ala Glu Arg Ala
            580                 585                 590

Ala Ala Leu Leu Arg Gly Gln Ala Thr Ile Ala Pro Ser Arg Gln Pro
        595                 600                 605

Val Ala Val
    610

<210> SEQ ID NO 7
<211> LENGTH: 568
<212> TYPE: PRT
<213> ORGANISM: Phaeodactylum tricornutum

<400> SEQUENCE: 7

Tyr Asp Tyr Ile Ile Cys Gly Gly Gly Leu Ala Gly Cys Val Leu Ala
1               5                   10                  15

Glu Arg Leu Ser Gln Asp Glu Ser Lys Arg Val Leu Val Leu Glu Ala
                20                  25                  30

Gly Gly Ser Asp Tyr Lys Ser Leu Phe Ile Arg Ile Pro Ala Gly Val
            35                  40                  45

Leu Arg Leu Phe Arg Ser Lys Tyr Asp Trp Gln His Glu Thr Gly Gly
        50                  55                  60

Glu Lys Gly Cys Asn Gly Arg Asn Val Phe Leu Gln Arg Gly Lys Ile
65                  70                  75                  80

Leu Gly Gly Ser Ser Cys Thr Asn Val Cys Leu His His Arg Gly Ser
                85                  90                  95

Ala Glu Asp Tyr Asn Ser Trp Asn Ile Pro Gly Trp Thr Ala Thr Asp
            100                 105                 110

Val Leu Pro Phe Phe Lys Gln Ser Gln Lys Asp Glu Thr Gly Arg Asp
        115                 120                 125

Ala Thr Phe His Gly Ala Asp Gly Glu Trp Val Met Asp Glu Val Arg
    130                 135                 140

Tyr Gln Asn Pro Leu Ser Lys Leu Phe Leu Glu Val Gly Glu Ala Ala
145                 150                 155                 160
```

-continued

```
Gly Leu Gly Thr Asn Asp Asp Phe Asn Asn Trp Ser His Pro Gln Asp
                165                 170                 175
Gly Val Gly Arg Phe Gln Val Ser Glu Val Asn Gly Glu Arg Cys Ser
            180                 185                 190
Gly Ala Thr Ala Phe Leu Ser Lys Ala Ala Lys Arg Ser Asn Val Ile
        195                 200                 205
Val Arg Thr Gly Thr Met Val Arg Arg Ile Asp Phe Asp Glu Thr Lys
    210                 215                 220
Thr Ala Lys Gly Ile Thr Tyr Asp Leu Met Gly Asp Asp Thr Cys Thr
225                 230                 235                 240
Thr Phe Gln Ala Cys Leu Lys Glu Gly Gly Glu Val Leu Val Thr Gly
                245                 250                 255
Gly Ala Ile Ala Ser Pro Gln Leu Leu Met Cys Ser Gly Ile Gly Pro
            260                 265                 270
Gly Lys His Leu Arg Ser Leu Gly Ile Pro Val Val His Asp Asn Ser
        275                 280                 285
Ala Val Gly Glu Asn Leu Gln Asp His Pro Ala Ala Val Val Ser Phe
    290                 295                 300
Lys Thr Pro Gln Lys Gly Val Ser Val Thr Ser Lys Leu Arg Leu Phe
305                 310                 315                 320
Gly Lys Thr Asn Pro Ile Pro Val Phe Gln Trp Leu Phe Phe Lys Ser
                325                 330                 335
Gly Leu Leu Thr Ser Thr Gly Cys Asp His Gly Ala Phe Val Arg Thr
            340                 345                 350
Ser Asp Ser Leu Glu Gln Pro Asp Leu Gln Ile Arg Phe Leu Ala Ala
        355                 360                 365
Arg Ala Leu Gly Pro Asp Gly Met Thr Thr Tyr Thr Lys Phe Arg Thr
    370                 375                 380
Met Lys Thr Val Glu Asp Gly Tyr Ser Phe Gln Ser Val Ala Cys Arg
385                 390                 395                 400
Ala Lys Ser Lys Gly Arg Ile Arg Leu Ser Ser Ser Asn Ser His Val
                405                 410                 415
Lys Pro Met Ile Asp Gly Gly Tyr Leu Ser Asn Gln Asp Asp Leu Ala
            420                 425                 430
Thr Leu Arg Ala Gly Ile Lys Leu Gly Arg Met Leu Gly Asn Arg Pro
        435                 440                 445
Glu Trp Gly Glu Tyr Leu Gly Gln Glu Val Tyr Pro Gly Pro Asp Val
    450                 455                 460
Gln Thr Asp Glu Glu Ile Asp Glu Tyr Ile Arg Asn Ser Leu His Thr
465                 470                 475                 480
Ala Asn Ala Leu Thr Gly Thr Cys Lys Met Gly Thr Gly Arg Gly Ala
                485                 490                 495
Val Val Gly Pro Asp Leu Arg Val Ile Gly Val Asn Gly Val Arg Val
            500                 505                 510
Gly Asp Ser Ser Val Phe Pro Cys Ile Pro Gly Gly Gln Thr Ala Thr
        515                 520                 525
Pro Thr Val Met Ile Gly Asp Arg Ala Ala Val Phe Val Arg Gln Pro
    530                 535                 540
Val Ser Gln Leu Asn Ile Glu Ile Phe Arg Glu Lys Gly Gly Thr His
545                 550                 555                 560
Pro Gly Ala Thr Thr Ala Ser Ala
                565
```

```
<210> SEQ ID NO 8
<211> LENGTH: 614
<212> TYPE: PRT
<213> ORGANISM: Phaeodactylum tricornutum

<400> SEQUENCE: 8

Met Lys Lys Ser Leu Arg Ser Leu Leu Val Trp Thr Leu Ser Val Ser
1               5                   10                  15

Ser Ala Ser Ala Thr Thr Met Ala Gly Ala Lys Pro Leu Gly Asn Val
            20                  25                  30

Pro Arg Ala Gln Glu Asp Glu Arg Lys Val Val Ala Glu Pro Tyr Asp
        35                  40                  45

Tyr Ile Ile Cys Gly Gly Gly Leu Ala Gly Cys Val Leu Ala Glu Arg
    50                  55                  60

Leu Ser Gln Asp Glu Ser Lys Arg Val Leu Val Leu Glu Ala Gly Gly
65                  70                  75                  80

Ser Asp Tyr Lys Ser Leu Phe Ile Arg Ile Pro Ala Gly Val Leu Arg
                85                  90                  95

Leu Phe Arg Ser Lys Tyr Asp Trp Gln His Glu Thr Gly Gly Glu Lys
            100                 105                 110

Gly Cys Asn Gly Arg Asn Val Phe Leu Gln Arg Gly Lys Ile Leu Gly
        115                 120                 125

Gly Ser Ser Cys Thr Asn Val Cys Leu His His Arg Gly Ser Ala Glu
    130                 135                 140

Asp Tyr Asn Ser Trp Asn Ile Pro Gly Trp Thr Ala Thr Asp Val Leu
145                 150                 155                 160

Pro Phe Phe Lys Gln Ser Gln Lys Asp Glu Thr Gly Arg Asp Ala Thr
                165                 170                 175

Phe His Gly Ala Asp Gly Glu Trp Val Met Asp Glu Val Arg Tyr Gln
            180                 185                 190

Asn Pro Leu Ser Lys Leu Phe Leu Glu Val Gly Glu Ala Ala Gly Leu
        195                 200                 205

Gly Thr Asn Asp Asp Phe Asn Asn Trp Ser His Pro Gln Asp Gly Val
    210                 215                 220

Gly Arg Phe Gln Val Ser Glu Val Asn Gly Glu Arg Cys Ser Gly Ala
225                 230                 235                 240

Thr Ala Phe Leu Ser Lys Ala Ala Lys Arg Ser Asn Val Ile Val Arg
                245                 250                 255

Thr Gly Thr Met Val Arg Arg Ile Asp Phe Asp Glu Thr Lys Thr Ala
            260                 265                 270

Lys Gly Ile Thr Tyr Asp Leu Met Gly Asp Asp Thr Cys Thr Thr Phe
        275                 280                 285

Gln Ala Cys Leu Lys Glu Gly Gly Glu Val Leu Val Thr Gly Gly Ala
    290                 295                 300

Ile Ala Ser Pro Gln Leu Leu Met Cys Ser Gly Ile Gly Pro Gly Lys
305                 310                 315                 320

His Leu Arg Ser Leu Gly Ile Pro Val Val His Asp Asn Ser Ala Val
                325                 330                 335

Gly Glu Asn Leu Gln Asp His Pro Ala Ala Val Val Ser Phe Lys Thr
            340                 345                 350

Pro Gln Lys Gly Val Ser Val Thr Ser Lys Leu Arg Leu Phe Gly Lys
        355                 360                 365

Thr Asn Pro Ile Pro Val Phe Gln Trp Leu Phe Phe Lys Ser Gly Leu
    370                 375                 380
```

```
Leu Thr Ser Thr Gly Cys Asp His Gly Ala Phe Val Arg Thr Ser Asp
385                 390                 395                 400

Ser Leu Glu Gln Pro Asp Leu Gln Ile Arg Phe Leu Ala Ala Arg Ala
                405                 410                 415

Leu Gly Pro Asp Gly Met Thr Thr Tyr Thr Lys Phe Arg Thr Met Lys
            420                 425                 430

Thr Val Glu Asp Gly Tyr Ser Phe Gln Ser Val Ala Cys Arg Ala Lys
        435                 440                 445

Ser Lys Gly Arg Ile Arg Leu Ser Ser Ser Asn Ser His Val Lys Pro
    450                 455                 460

Met Ile Asp Gly Gly Tyr Leu Ser Asn Gln Asp Asp Leu Ala Thr Leu
465                 470                 475                 480

Arg Ala Gly Ile Lys Leu Gly Arg Met Leu Gly Asn Arg Pro Glu Trp
                485                 490                 495

Gly Glu Tyr Leu Gly Gln Glu Val Tyr Pro Gly Pro Asp Val Gln Thr
                500                 505                 510

Asp Glu Glu Ile Asp Glu Tyr Ile Arg Asn Ser Leu His Thr Ala Asn
            515                 520                 525

Ala Leu Thr Gly Thr Cys Lys Met Gly Thr Gly Arg Gly Ala Val Val
        530                 535                 540

Gly Pro Asp Leu Arg Val Ile Gly Val Asn Gly Val Arg Val Gly Asp
545                 550                 555                 560

Ser Ser Val Phe Pro Cys Ile Pro Gly Gly Gln Thr Ala Thr Pro Thr
                565                 570                 575

Val Met Ile Gly Asp Arg Ala Ala Val Phe Val Arg Gln Pro Val Ser
            580                 585                 590

Gln Leu Asn Ile Glu Ile Phe Arg Glu Lys Gly Gly Thr His Pro Gly
        595                 600                 605

Ala Thr Thr Ala Ser Ala
        610

<210> SEQ ID NO 9
<211> LENGTH: 585
<212> TYPE: PRT
<213> ORGANISM: Coccomyxa subellipsoidea

<400> SEQUENCE: 9

Ala Leu Arg Val Arg Ala Ile Ile Lys Ser Asp Asn Pro Ala Ala Asp
1               5                   10                  15

Lys Tyr Asp Phe Ile Leu Val Gly Gly Thr Ala Gly Cys Val Leu
                20                  25                  30

Ala Asn Arg Leu Thr Ala Asp Gly Ser Lys Lys Val Leu Leu Leu Glu
            35                  40                  45

Ala Gly Gly Ala Asn Lys Ala Arg Glu Val Arg Thr Pro Ala Gly Leu
    50                  55                  60

Pro Arg Leu Phe Lys Ser Ala Leu Asp Trp Asn Leu Tyr Ser Ser Leu
65                  70                  75                  80

Gln Gln Ala Ala Ser Asp Arg Ser Ile Tyr Leu Ala Arg Gly Lys Leu
                85                  90                  95

Leu Gly Gly Ser Ser Ala Thr Asn Ala Thr Leu Tyr His Arg Gly Thr
                100                 105                 110

Ala Ala Asp Tyr Asp Ala Trp Gly Val Pro Gly Trp Thr Ser Gln Asp
            115                 120                 125

Ala Leu Arg Trp Phe Ile Gln Ala Glu Asn Asn Cys Arg Gly Ile Glu
        130                 135                 140
```

```
Asp Gly Val His Gly Thr Gly Leu Met Arg Val Glu Asn Pro Arg
145                 150                 155                 160

Tyr Asn Asn Pro Leu His Glu Val Phe Phe Gln Ala Ala Lys Gln Ala
            165                 170                 175

Gly Leu Pro Glu Asn Asp Asn Phe Asn Asn Trp Gly Arg Ser Gln Ala
            180                 185                 190

Gly Tyr Gly Glu Phe Gln Val Thr His Ser Lys Gly Glu Arg Ala Asp
        195                 200                 205

Cys Phe Arg Met Tyr Leu Glu Pro Val Met Gly Arg Ser Asn Leu Thr
        210                 215                 220

Val Leu Thr Gly Ala Lys Thr Leu Lys Ile Glu Thr Glu Lys Ser Gly
225                 230                 235                 240

Gly Ala Thr Val Ser Arg Gly Val Thr Phe Gln Val Asn Gly Gln Asp
                245                 250                 255

Gly Ser Lys His Ser Ala Glu Leu Ala Ala Gly Gly Glu Val Val Leu
            260                 265                 270

Cys Ala Gly Ser Ile His Ser Pro Gln Ile Leu Gln Leu Ser Gly Ile
        275                 280                 285

Gly Pro Gln Ala Glu Leu Arg Ser Lys Asp Ile Pro Val Val Ala Asp
290                 295                 300

Leu Pro Gly Val Gly Gln Asn Met Gln Asp His Pro Ala Cys Leu Ser
305                 310                 315                 320

Ala Phe Tyr Leu Lys Glu Ser Ala Gly Pro Ile Ser Val Thr Asp Glu
                325                 330                 335

Leu Leu His Thr Asn Gly Arg Ile Arg Ala Arg Ala Ile Leu Lys Tyr
            340                 345                 350

Leu Leu Phe Lys Lys Gly Pro Leu Ala Thr Thr Gly Cys Asp His Gly
        355                 360                 365

Ala Phe Val Lys Thr Ala Gly Gln Ser Glu Pro Asp Leu Gln Ile Arg
        370                 375                 380

Phe Val Pro Gly Leu Ala Leu Asp Pro Asp Gly Ile Gly Ser Tyr Thr
385                 390                 395                 400

Ala Phe Gly Lys Met Lys Asp Gln Lys Trp Pro Ser Gly Ile Thr Phe
                405                 410                 415

Gln Leu Leu Gly Val Arg Pro Lys Ser Arg Gly Ser Val Gly Leu Arg
            420                 425                 430

Ser Asp Asp Pro Trp Asp Ala Pro Lys Leu Asp Ile Gly Phe Leu Thr
        435                 440                 445

Asp Lys Glu Gly Ala Asp Leu Ala Thr Leu Arg Ser Gly Ile Lys Leu
        450                 455                 460

Ser Arg Glu Ile Ala Ala Glu Pro Ala Phe Gly Ala Tyr Val Gly Asn
465                 470                 475                 480

Glu Leu His Pro Gly Ala Ala Ala Ser Ser Asp Ser Ala Ile Asp Ser
                485                 490                 495

Phe Ile Arg Asp Thr Val His Ser Gly Asn Ala Asn Val Gly Thr Cys
            500                 505                 510

Ser Met Gly Val Asn Gly Asn Ala Val Val Asp Pro Ser Leu Arg Val
        515                 520                 525

Phe Gly Ile Arg Gly Leu Arg Val Ala Asp Ala Ser Val Ile Pro Val
        530                 535                 540

Ile Pro Gly Gly Gln Thr Gly Ala Ala Thr Val Met Val Ala Glu Arg
545                 550                 555                 560
```

```
Ala Ala Glu Ile Leu Leu Gly Ser Asn Gln Lys Gln Pro Ala Ala Ala
                565                 570                 575

Val Pro Ala Ala Gln Pro Ala Leu Ala
            580                 585

<210> SEQ ID NO 10
<211> LENGTH: 580
<212> TYPE: PRT
<213> ORGANISM: Volvox carteri

<400> SEQUENCE: 10

Pro Val Ala Val Lys Ala Ala Ser Val Gly Ser Glu Lys Phe Asp
1               5                   10                  15

Tyr Ile Leu Val Gly Gly Thr Ala Gly Cys Val Leu Ala Asn Lys
                20                  25                  30

Leu Ser Ala Asn Gly Ser Lys Lys Val Leu Val Glu Ala Gly Pro
                35                  40                  45

Thr Gly Asp Ala Met Glu Val Ala Val Pro Ala Gly Ile Ala Arg Leu
    50                  55                  60

Phe Ala His Pro Val Phe Asp Trp Gly Met Ser Ser Leu Thr Gln Gln
65                  70                  75                  80

Gln Leu Val Ala Arg Glu Ile Tyr Leu Ala Arg Gly Arg Leu Leu Gly
                85                  90                  95

Gly Ser Ser Gly Thr Asn Ala Thr Leu Tyr His Arg Gly Thr Pro Ala
                100                 105                 110

Asp Tyr Asp Ser Trp Gly Leu Glu Gly Trp Thr Ser Lys Asp Leu Leu
                115                 120                 125

Asp Trp Phe Val Lys Ala Glu Cys Tyr Gly Asp Gly Pro Arg Ala Phe
        130                 135                 140

His Gly Gln Ser Gly Ser Met Asn Val Glu Gln Pro Arg Tyr Gln Asn
145                 150                 155                 160

Val Leu His Asp Glu Phe Phe Arg Ala Ala Ala Ala Gly Leu Pro
                165                 170                 175

Ala Asn Glu Asp Phe Asn Asp Trp Ser Arg Pro Gln Glu Gly Tyr Gly
                180                 185                 190

Glu Phe Gln Val Ala Gln Lys Asn Gly Glu Arg Ala Asp Thr Tyr Arg
            195                 200                 205

Thr Tyr Leu Lys Pro Ala Met Gly Arg Asp Asn Leu Lys Val Met Thr
    210                 215                 220

Gly Ala Arg Thr Thr Lys Val His Ile Glu Lys Ser Ser Thr Gly Pro
225                 230                 235                 240

Arg Ala Arg Gly Val Glu Tyr Ala Thr Gln Gln Phe Gly Glu Arg Tyr
                245                 250                 255

Thr Ala Glu Leu Thr Pro Gly Gly Val Leu Met Cys Thr Gly Ala
            260                 265                 270

Val His Thr Pro His Leu Leu Met Leu Ser Gly Ile Gly Pro Ala Pro
                275                 280                 285

Thr Leu Leu Glu His Gly Leu Asp Val Ile Ser Ser Leu Pro Gly Val
    290                 295                 300

Gly Ala Asn Leu Gln Asp His Pro Ala Val Leu Ala Val Arg Ala
305                 310                 315                 320

Lys Pro Glu Phe Glu Gly Leu Ser Val Thr Ser Glu Ile Tyr Asp Ser
                325                 330                 335

Lys Cys Asn Ile Arg Leu Gly Ala Val Met Lys Tyr Leu Phe Gly Arg
                340                 345                 350
```

```
Arg Gly Pro Leu Ala Thr Thr Gly Cys Asp His Gly Ala Phe Val Arg
            355                 360                 365

Thr Ser Ala Ser His Ser Gln Pro Asp Leu Gln Met Arg Phe Val Pro
        370                 375                 380

Gly Cys Ala Leu Asp Pro Asp Gly Val Lys Ser Tyr Ile Val Phe Gly
385                 390                 395                 400

Glu Leu Lys Lys Gln Gly Arg Ala Trp Pro Gly Gly Ile Thr Leu Gln
                405                 410                 415

Leu Leu Gly Ile Arg Ala Lys Ser Arg Gly Ser Ile Gly Leu Lys Ala
            420                 425                 430

Ala Asp Pro Phe Ile Asn Pro Ala Ile Asn Ile Asn Tyr Phe Ser Asp
        435                 440                 445

Pro Glu Asp Leu Ala Thr Leu Lys Asn Gly Val Arg Ile Ala Arg Glu
    450                 455                 460

Ile Val Ala Gln Glu Pro Leu Arg Lys Tyr Leu Leu Glu Glu Thr Phe
465                 470                 475                 480

Pro Gly Glu Arg Ala Asn Thr Asp Lys Asp Ile Glu Glu Tyr Val Arg
                485                 490                 495

Arg Thr Val His Ser Gly Asn Ala Leu Val Gly Thr Cys Ala Met Gly
            500                 505                 510

Thr Thr Pro Ala Ser Gly Ala Val Val Ser Ser Ala Asp Leu Lys Val
        515                 520                 525

Phe Gly Val Asp Gly Leu Arg Val Asp Ala Ser Val Leu Pro Arg
    530                 535                 540

Ile Pro Gly Gly Gln Thr Gly Ala Ala Thr Val Met Val Ala Glu Arg
545                 550                 555                 560

Ala Ala Ala Met Leu Leu Gly Gln Ala Thr Ile Thr Ser Arg Arg Glu
                565                 570                 575

Pro Ala Ala Val
            580

<210> SEQ ID NO 11
<211> LENGTH: 557
<212> TYPE: PRT
<213> ORGANISM: Ectocarpus siliculosus

<400> SEQUENCE: 11

Val Pro Ala Ala Arg Tyr Ala Thr Ser Ser Val Ser Met Ser Val Ala
1               5                   10                  15

Glu Glu Gly His Lys Phe Ile Ile Gly Gly Gly Thr Ala Gly Cys
                20                  25                  30

Val Leu Ala Asn Arg Leu Ser Ala Asp Lys Asp Asn Ser Val Leu Val
            35                  40                  45

Leu Glu Ala Gly Ser Glu Lys Phe Asn Asp Arg Asn Ile Lys Met Pro
        50                  55                  60

Ile Ala Ile Leu Arg Leu Phe Lys Ser Val Phe Asp Trp Gly Phe Gln
65                  70                  75                  80

Ser Glu Asn Glu Lys Phe Ala Thr Gly Asp Gly Ile Tyr Leu Cys Arg
                85                  90                  95

Gly Lys Val Leu Gly Gly Ser Ser Cys Thr Asn Val Met Leu Tyr His
                100                 105                 110

Arg Gly Glu Glu Ala Asp Tyr Asp Ala Trp Gly Val Asp Gly Trp Lys
            115                 120                 125

Gly Lys Asp Val Leu Pro Tyr Phe Lys Lys Ala Glu Asn Asn Arg Ser
```

```
                130             135             140
Lys Lys Lys Gly Glu Phe His Gly Lys Gly Leu Met Gln Val Glu
145                 150                 155                 160

Asn Ala Arg Tyr Met Asn Pro Leu Thr Lys Leu Phe Lys Ala Cys
                165                 170                 175

Glu Gln Ala Gly Leu Ser Glu Asn Glu Asp Phe Asn Asp Trp Ser His
                180                 185                 190

Ser Gln Glu Gly Phe Gly Arg Phe Gln Val Ala Gln Lys Arg Gly Lys
                195                 200                 205

Arg Cys Ser Ala Ala Ser Ser Tyr Leu Lys Glu Ala Met Gly Arg Lys
                210                 215                 220

Asn Leu Asp Val Gln Thr Ser Ala Gln Ile Thr Lys Val Leu Ile Glu
225                 230                 235                 240

Asn Gly Gly Ala Ile Gly Val Glu Tyr Val Arg Asp Gly Glu Lys Lys
                245                 250                 255

Ile Ala Lys Leu Ala Val Gly Gly Glu Ile Leu Leu Ala Gly Gly Ala
                260                 265                 270

Ile Ser Ser Pro Gln Val Leu Met Leu Ser Gly Val Gly Pro Ala Glu
                275                 280                 285

His Leu Arg Ser Lys Gly Ile Glu Val Lys Ser Asn Val Pro Gly Val
                290                 295                 300

Gly Lys Asn Leu Arg Asp His Pro Ala Val Thr Val Met Ala Asp Ile
305                 310                 315                 320

Asn Lys Pro Ile Ser Ile Thr Asp Lys Val Leu Lys Glu Gly Ser Gly
                325                 330                 335

Asp Val Asn Lys Ile Thr Ala Leu Gln Trp Leu Leu Thr Gly Thr Gly
                340                 345                 350

Pro Leu Thr Ser Pro Gly Cys Glu Asn Gly Ala Phe Phe Lys Thr Thr
                355                 360                 365

Pro Asp Lys Ala Ala Ala Asp Leu Gln Leu Arg Phe Val Pro Gly Arg
                370                 375                 380

Ser Thr Thr Pro Asp Gly Val Lys Ala Tyr Asn Thr Ile Gly Thr Lys
385                 390                 395                 400

Gly Arg Pro Pro Ser Gly Val Thr Val Gln Val Val Gly Ile Arg Pro
                405                 410                 415

Gln Ser Glu Gly His Val Glu Leu Arg Ser Ser Asp Pro Phe Asp Lys
                420                 425                 430

Pro His Ile Val Thr Asn Tyr Leu Glu Ser Gly Glu Asp Met Ala Ser
                435                 440                 445

Leu Thr Asn Gly Ile Glu Met Ala Arg Lys Leu Phe Asp Gln Glu Ala
450                 455                 460

Phe Gly Glu Met Val Asp Lys Glu Val Phe Pro Gly Arg Asp Asn Lys
465                 470                 475                 480

Glu Ile Ser Glu Tyr Ile Lys Ser Thr His Ser Ala Asn Ala Leu
                485                 490                 495

Val Gly Thr Cys Lys Met Gly Glu Glu Ser Asp Asn Met Ser Val Val
                500                 505                 510

Asn Ser Ala Leu Lys Val Lys Gly Val Ala Gly Leu Arg Val Ile Asp
                515                 520                 525

Ser Ser Val Met Pro Ser Ile Pro Gly Gly Gln Thr Ala Ala Pro Thr
                530                 535                 540

Ile Met Ile Ala Glu Lys Ala Ala Asp Met Leu Met Ala
545                 550                 555
```

<210> SEQ ID NO 12
<211> LENGTH: 601
<212> TYPE: PRT
<213> ORGANISM: Emiliania huxleyi

<400> SEQUENCE: 12

```
Leu Arg Gly Gly Ser Gly Val Thr Gly Gly Ser Leu Arg Gly Gly
1               5                   10                  15

Gly Ser Pro Ala Ile Asp Gly Glu Phe Asp Tyr Ile Ile Val Gly
                20                  25                  30

Gly Ala Ala Gly Cys Val Leu Ala Asn Arg Leu Ser Ala Asp Pro Ala
            35                  40                  45

His Arg Val Leu Leu Ile Glu Ala Gly Gly Asp Ala Ser Arg Asp Lys
    50                  55                  60

Arg Ala Gln Val Pro Trp Ala Phe Thr Lys Leu Leu Arg Ser Glu Tyr
65                  70                  75                  80

Asp Trp Asp Phe His Val Glu Ala Glu Ala Val Asn Gln Gln Glu
                85                  90                  95

Val Tyr Leu Cys Arg Gly Lys Ala Leu Gly Gly Ser Ser Val Thr Asn
            100                 105                 110

Val Met Leu Tyr His Arg Gly Ser Pro Ala Asp Tyr Asp Ala Trp Glu
        115                 120                 125

Glu Ala Gly Ala Arg Gly Trp Gly Ala Lys Asp Val Leu Pro Tyr Tyr
    130                 135                 140

Leu Arg Val Glu Asp Tyr Gly Asp Gly Ala Ser Gln Tyr His Ala Val
145                 150                 155                 160

Gly Gly His Val Ser Val Gln Glu Val Pro Tyr Gln Asn Gln Leu Ser
                165                 170                 175

Ala Thr Phe Leu Arg Ala Met Gly Gln Leu Gly Phe Arg Pro Asn Gly
            180                 185                 190

Asp Phe Asn Asp Trp Ser Ser Pro Gln Glu Gly Tyr Gly Arg Tyr Lys
        195                 200                 205

Val Thr Gln Arg Ala Gly Arg Arg Cys Thr Ala Ala Asp Gly Tyr Leu
    210                 215                 220

Ala Ala Ala Arg Glu Arg Ala Asn Leu Val Val Val Thr Gly Ala Gln
225                 230                 235                 240

Ala Thr Arg Leu Ala Leu Asp Ser Ala Tyr Asp Gly Ala Gly Arg Leu
                245                 250                 255

Gln Val Ser Gly Val Glu Phe Ala Arg Gly Asp Glu Arg Glu Pro Cys
            260                 265                 270

Ser Val Arg Leu Ala Arg Gly Gly Glu Ala Val Leu Cys Ala Gly Ala
        275                 280                 285

Val Gln Thr Pro His Leu Leu Leu Leu Ser Gly Ile Gly Pro Ala Glu
    290                 295                 300

His Leu Arg Glu Val Gly Val Pro Val Arg Ala Asp Leu Pro Gly Val
305                 310                 315                 320

Gly Ser Gly Leu Gln Asp His Pro Ala Val Val Ser Tyr Glu Ser
                325                 330                 335

Lys Lys Ala Val Ala Ala Thr Asp Asp Ala Leu Leu Lys Gly Tyr Ala
            340                 345                 350

Ser Leu Val Asn Pro Leu Ala Met Leu Arg Trp Leu Leu Phe Gly Arg
        355                 360                 365

Gly Pro Leu Ala Cys Ala Ala Cys Asp His Gly Gly Phe Val Arg Ser
```

```
              370                 375                 380
Ser Pro Asp Leu Asp Gln Pro Asp Val Gln Ile Arg Phe Val Pro Ala
385                 390                 395                 400

Arg Ala Ser Ser Ala Ser Gly Met Asn Thr Leu Ile Glu Leu Gly Arg
                405                 410                 415

Arg Ala Arg Phe Leu Pro Gly Phe Ser Thr Gln Val Val Ala Cys Arg
                420                 425                 430

Pro Arg Ser Glu Gly Arg Val Arg Leu Arg Ser Ala Asp Pro Phe Ala
                435                 440                 445

Lys Pro Ile Ile Glu Gly Ile His Leu Gly Ala Ala Glu Asp Val Ala
                450                 455                 460

Ser Leu Arg His Gly Ile Arg Leu Gly Arg Gln Val Cys Ala Ala Ala
465                 470                 475                 480

Ala Phe Asp Glu Tyr Arg Gly Glu Val Phe Pro Gly Ala Ala Val
                485                 490                 495

Gln Ser Asp Glu Gln Ile Asp Glu Tyr Ile Arg Ser Val His Ser
                500                 505                 510

Ala Asn Ala Leu Thr Ser Ser Cys Arg Met Gly Asp Pro Ser Asp Pro
                515                 520                 525

Ala Ala Val Leu Asp Ser His Leu Arg Val Arg Gly Val Gly Gly Leu
                530                 535                 540

Arg Val Ala Asp Ala Ser Ala Met Pro Arg Ile Ile Gly Gly Gln Thr
545                 550                 555                 560

Gln Ala Pro Thr Tyr Met Leu Ala Glu Arg Ala Ala Asp Ile Leu Leu
                565                 570                 575

His Ala Arg Leu Gln Ala His Glu Pro Ala Thr Glu Ser Val Ser Gln
                580                 585                 590

Arg Leu Glu Val Ala Ala Ala Leu
                595                 600

<210> SEQ ID NO 13
<211> LENGTH: 533
<212> TYPE: PRT
<213> ORGANISM: Aureococcus anophagefferens

<400> SEQUENCE: 13

Leu Ser Glu Asp Pro Ser Lys Lys Val Leu Val Leu Glu Ala Gly Asp
1               5                   10                  15

Arg Gly Pro Asn Ser Pro Leu Val Lys Ile Pro Val Ala Ile Leu Lys
                20                  25                  30

Leu Phe Lys Ser Ala Tyr Asp Trp Asn Phe Ala Thr Arg Pro Ser Glu
                35                  40                  45

Ala Val Ala Asp Arg Ser Leu Tyr Val Cys Arg Gly Lys Gly Leu Gly
                50                  55                  60

Gly Ser Ser Leu Thr Asn Val Met Leu Tyr Asn Arg Gly Ser Ala Asn
65              70                  75                  80

Asp Tyr Asp Ala Trp Ala Ala Cys Gly Asp Ser Trp Gly Ala
                85                  90                  95

Glu Glu Met Leu Gly Tyr Phe Lys Lys Ala Glu Asp Cys Leu Val Pro
                100                 105                 110

Ala His Arg Ala Asn His Tyr His Gly Val Gly Gly Pro Tyr Ala Ser
                115                 120                 125

Ser His Val Pro Tyr Thr Asn Glu Met Ser Thr Ala Phe Val Glu Ala
                130                 135                 140
```

Ala Val Glu Asp Gly Gly Val Arg Asn Gly Asp Phe Asn Asp Trp Ser
145                 150                 155                 160

Thr Ser Gln Val Gly Phe Gly Arg Phe Ala Val Ser Gln Arg Lys Gly
            165                 170                 175

Ala Arg Val Asp Ala Ala Thr Ala Tyr Leu Pro Arg Lys Val Arg Arg
            180                 185                 190

Arg Ala Asn Leu Asp Val Val Arg Gly Ala Ala Leu Ser Gly Val Thr
            195                 200                 205

Trp Asn Ala Asn Lys Ala Thr Gly Val Glu Phe Ala Phe Gly Gly Val
210                 215                 220

Ser Gly Ile Ala Cys Gly Gly Glu Val Ile Leu Ser Gly Gly Ala Val
225                 230                 235                 240

His Ser Pro Gln Met Leu Met Leu Ser Gly Val Gly Ala Lys Ala Gln
            245                 250                 255

Leu Glu Glu Phe Gly Ile Pro Val Val Ala Asp Arg Pro Gly Val Gly
            260                 265                 270

Lys Asn Leu Gln Asp His Pro Ala Cys Leu Val Ser Trp Arg Gly Ser
            275                 280                 285

Ala Lys Ala Gln Gly Lys Ser His Ser Thr Gln Leu Arg Ile Pro Gly
            290                 295                 300

Thr Thr Lys Thr Ser Pro Lys Ala Leu Leu Gln Trp Leu Phe Leu Gly
305                 310                 315                 320

Arg Gly Pro Leu Ala Ser Pro Gly Cys Asp His Gly Phe Ala Lys
            325                 330                 335

Val Gly Ala Gly Asp Gly Asp Cys Asp Val Gln Phe Arg Phe Leu Ala
            340                 345                 350

Thr Lys Ser Ile Thr Pro Asp Gly Met Ser Thr Ile Ser Asp Ser Tyr
            355                 360                 365

Glu Ala Ala Val Asp His Pro Asp Gly Leu Thr Ile Gln Thr Ile Val
            370                 375                 380

Ala Arg Pro Lys Ser Arg Ala Gly Glu Val Lys Leu Ala Ser Arg Asp
385                 390                 395                 400

Pro Ala Ala Lys Pro Val Ile Glu Asn Ala Tyr Leu Ser Asp Glu Ala
            405                 410                 415

Asp Val Met Thr Met Val Lys Ala Leu Gln Lys Ala Arg Ser Ile Ala
            420                 425                 430

Ser Arg Ala Pro Leu Ser Ala Tyr Ala Gly His Glu Glu Phe Pro Gly
            435                 440                 445

Glu Asp Val Ala Asp Glu Arg Gln Leu Ala Ala Tyr Val Arg Asn Thr
450                 455                 460

Ala His Thr Ala Asn Ala Val Val Gly Thr Cys Lys Met Gly Glu Ser
465                 470                 475                 480

Ser Asp Ala Leu Ala Val Val Asp Asn His Leu Lys Val Ile Gly Val
            485                 490                 495

Ser Asn Leu Arg Val Val Asp Ala Ser Val Met Pro Thr Leu Pro Gly
            500                 505                 510

Gly Gln Thr Ala Ala Ser Thr Val Ala Leu Ala Glu Lys Ala Ala Asp
            515                 520                 525

Leu Ile Lys Gly Gly
    530

<210> SEQ ID NO 14
<211> LENGTH: 1236
<212> TYPE: PRT

<213> ORGANISM: Nannochloropsis gaditana

<400> SEQUENCE: 14

```
Leu Ser Lys Thr Thr Ile Gly Leu Gln Ser Phe Val Thr Ala Asn Tyr
1               5                   10                  15

Gly Val Arg Arg Ala Ile Ser Leu Arg Gly Gly Leu Gln Ser Val Ser
            20                  25                  30

Met Lys Ala Pro Ala Ala Val Ala Ser Ser Thr Tyr Asp Tyr Ile Ile
        35                  40                  45

Val Gly Gly Gly Ile Gly Gly Cys Val Leu Ala Asn Arg Leu Thr Glu
    50                  55                  60

Ser Gly Arg Phe Lys Val Leu Leu Glu Ala Gly Lys Ser Ala Glu
65                  70                  75                  80

Arg Asn Pro Tyr Val Asn Ile Pro Ala Gly Val Val Arg Leu Phe Lys
                85                  90                  95

Ser Ala Leu Asp Trp Gln Phe Glu Ser Ala Pro Glu Arg His Leu Asp
            100                 105                 110

Gly Lys Glu Val Tyr Leu Val Arg Gly Lys Ala Met Gly Gly Ser Ser
        115                 120                 125

Ala Val Asn Val Met Leu Val His Arg Gly Ser Ala Ser Asp Tyr Ala
    130                 135                 140

Lys Trp Glu Ala Glu Gly Ala Gln Gly Trp Gly Pro Glu Glu Ala Leu
145                 150                 155                 160

Arg Tyr Phe Lys Lys Met Glu Asp Asn Leu Val Gly Gly Glu Gly Arg
                165                 170                 175

Trp His Gly Gln Gly Gly Met Tyr Pro Val Asp Asp Val Lys Tyr Gln
            180                 185                 190

Asn Pro Leu Ser Lys Arg Phe Leu Gln Ala Cys Glu Glu Tyr Gly Trp
        195                 200                 205

Arg Ala Asn Pro Asp Phe Asn Asp Trp Ser His Pro Gln Asp Gly Tyr
    210                 215                 220

Gly Ser Phe Lys Val Ala Gln Lys His Gly Lys Arg Val Thr Ala Ala
225                 230                 235                 240

Ser Gly Tyr Leu Asn Lys Ala Val Arg Arg Pro Asn Leu Asp Ile
                245                 250                 255

Leu Ser Glu Ala Leu Val Thr Arg Val Leu Leu Glu Gly Glu Gly Asp
            260                 265                 270

Val Lys Ala Val Gly Val Glu Phe Thr Gly Lys Asp Gly Lys Thr His
        275                 280                 285

Gln Val Arg Thr Thr Gly Lys Ala Gly Glu Val Leu Leu Ala Gly Gly
        290                 295                 300

Ala Val Asn Ser Pro Gln Leu Leu Met Leu Ser Gly Ile Gly Pro Glu
305                 310                 315                 320

Ala Asp Leu Gln Ala Val Gly Ile Ala Thr Lys Val Asn Arg Pro Gly
                325                 330                 335

Val Gly Glu Asn Leu Gln Asp His Pro Ala Val Thr Ile Ala His Asn
            340                 345                 350

Ile Thr Arg Pro Ile Ser Leu Cys Asp Asp Leu Phe Leu Phe His Thr
        355                 360                 365

Pro Val Pro Lys Pro His Gln Val Leu Arg Trp Thr Leu Thr Gly Ser
    370                 375                 380

Gly Pro Leu Thr Thr Pro Gly Cys Asp His Gly Ala Phe Leu Lys Thr
385                 390                 395                 400
```

```
Arg Glu Asp Leu Gln Glu Pro Asn Val Gln Phe Arg Phe Ile Ala Gly
                405                 410                 415

Arg Gly Ser Asp Pro Asp Gly Val Arg Ser Tyr Ile Met Gly Gly Ser
            420                 425                 430

Ala Arg Pro Leu Ser Gly Leu Thr Leu Gln Val Val Asn Ile Arg Pro
        435                 440                 445

Lys Ser Lys Gly Lys Leu Thr Leu Ala Ser Lys Asp Pro Leu Lys Lys
    450                 455                 460

Pro Arg Ile Glu Val Arg Tyr Leu Ser Ala Ala Glu Asp Leu Gln Ala
465                 470                 475                 480

Leu Arg Thr Gly Met Arg Ile Gly Arg Asp Leu Ile Lys Gln Arg Ala
                485                 490                 495

Phe Ala Asp Ile Leu Asp Glu Glu Val Phe Pro Gly Pro Ala Ala Gln
            500                 505                 510

Thr Asp Glu Glu Leu Asp Ala Tyr Ile Arg Asp Ser Leu His Thr Ala
        515                 520                 525

Asn Ala Leu Val Gly Thr Cys Lys Met Gly Ser Val Glu Asp Arg Asn
    530                 535                 540

Ala Val Asp Pro Glu Cys Arg Val Ile Gly Val Gly Gly Leu Arg
545                 550                 555                 560

Val Val Asp Ala Ser Val Met Pro Val Ile Pro Gly Gly Gln Thr Gly
                565                 570                 575

Ser Gly Thr Thr Met Leu Ala Glu Lys Ala Ala Asp Leu Val Arg Ala
            580                 585                 590

His Ala Gly Asp Leu Val Glu Met Gly Val Gln Asp Glu Arg Lys
        595                 600                 605

Gly Gly Trp Phe Asn Gly Leu Leu Gly Arg Lys Gln Lys Val Ala Thr
    610                 615                 620

Glu Lys Glu Arg Gly Glu Arg Gly Lys Ser Glu Arg Phe Val Ser Glu
625                 630                 635                 640

Val Ile Arg His Met Gly Arg Val Phe Val Gln Val Ser Arg Ala Arg
                645                 650                 655

Arg Ala Gln Thr Cys Met Arg Val Gly Lys Gly Leu Asp Arg Glu Arg
            660                 665                 670

Gln Leu Glu Cys Ala Met Arg Lys Glu Leu Thr Ile Ala Leu Phe Tyr
        675                 680                 685

Ala Met Leu Phe Thr Met Arg His Ser Gly Phe Leu Ser Thr Thr Gly
    690                 695                 700

Arg Ala Ser Tyr Lys Asp Leu Gly Tyr Leu Thr Gly Ser Cys Arg Ala
705                 710                 715                 720

His Pro Cys Thr Ser Pro Ser Ser Leu Cys Leu Phe Pro Glu Lys Pro
                725                 730                 735

Phe Met Lys Leu Ser Pro Ala Leu Ala Val Val Gly Phe Cys Phe Asn
            740                 745                 750

Ser Ile Asn Val Gln Gly Phe Leu Leu Ser Asn Leu Ala Gly Arg Ser
        755                 760                 765

Leu Lys His Pro Val Pro Gln Lys Gly Leu Tyr Ser Arg Ile Glu Tyr
    770                 775                 780

Asp Ala Arg Glu Pro Arg Leu Asp Glu Phe Gly Leu Pro Leu Asp Pro
785                 790                 795                 800

Ala Asp Leu Met Glu Lys Pro Arg Val Pro Leu Lys Asp Arg Val Tyr
                805                 810                 815

His Ile Ile Asp Met Thr Asn Asp Trp Val Asp Ala Val Ser Arg Gly
```

```
                    820                 825                 830
Arg Arg Glu Glu Glu Thr Arg Arg Ile Ile Gln Arg Arg Ala Ala
                835                 840                 845
Ala Lys Ala Met Ala Ile Lys Asp Lys Val Leu Ile Ser Leu Asp Tyr
        850                 855                 860
Val Phe His Pro Val Lys Ala Trp Arg Thr Phe Val Ala Asp Pro Leu
865                 870                 875                 880
Glu Ala Arg His Gln Arg Gln Leu Arg Gln Gln Ala Glu Lys Arg Ala
                885                 890                 895
Arg Leu Glu Arg Tyr Leu Gln Arg Tyr Asn Thr Val Lys Asn Arg Phe
        900                 905                 910
His Asp Thr Leu Asp Leu Leu Glu Ser Thr Thr Arg Thr Ser Val Lys
        915                 920                 925
Val Ala Lys Ser Val Ser Ser Ala Val Val Gly Ala Pro Gly Thr Val
        930                 935                 940
Thr Arg Thr Val Lys Glu Val Lys Ser Gln Ala Gln Gly Thr Ala Glu
945                 950                 955                 960
Ala Val Ala Lys Val Ser Ser Val Ser Ser Val Ser Lys Ile
                965                 970                 975
Thr Ser Val Ile Arg Lys Glu Asp Gly Ala Leu Ala Gly Ala Lys Gly
        980                 985                 990
Lys Lys Asp Pro Arg Ser Glu Asp Glu Gly Lys Ala Asp Pro Val Lys
        995                 1000                1005
Val Arg Glu Ile Trp Glu Thr Lys Glu Gln Thr Ala  Ile Arg Thr
        1010                1015                1020
Ile Trp Glu Ala Asp Glu Leu Val Thr Pro Val Thr  Pro Pro Ala
        1025                1030                1035
Thr Ala Met Ala Ser Thr Val Ser Val Ser Glu Pro  Gln Asp Glu
        1040                1045                1050
Asn Glu Ala Ser Ile Ser Gln Gly Ala Ala Pro Ser  Pro Ser Thr
        1055                1060                1065
Ser Ser Pro Ser Ser Pro Glu Pro Val Thr Arg Leu  Ser Phe Arg
        1070                1075                1080
Ala Arg Val Glu Ala Asp Glu Lys Glu Arg Phe Gly  Ser Arg Arg
        1085                1090                1095
Leu Lys Ile Ser Gly Asn Val Pro Pro Thr Ala Ser  Pro Thr Arg
        1100                1105                1110
Gly Ala Ser Ser Leu Pro Leu Asp Thr Leu Ser Ser  Ser Ala Thr
        1115                1120                1125
Gln Thr Phe Glu Arg Ser Lys Val Gly Pro Pro Ile  Arg Thr Ser
        1130                1135                1140
Lys Ala Arg Cys Ile Gly Lys Cys Val His Asn Gly  Trp Lys Gly
        1145                1150                1155
Ile Cys Glu Glu Trp Phe Val His Ile Ser Phe Pro  Thr Tyr Ala
        1160                1165                1170
Val Ser Ile Val Arg Pro Pro Met His Val His Asn  Phe Lys Val
        1175                1180                1185
Ile Cys Cys Val Leu Ala Val Arg His Ala Arg Arg  Lys Lys Glu
        1190                1195                1200
Met Ser Thr Ala Leu Ser Thr His Leu Ile Tyr Leu  Leu Leu Lys
        1205                1210                1215
Thr Val Lys Met Leu Gln Asp Leu Pro Gln Leu Arg  Arg Lys Gly
        1220                1225                1230
```

Lys Thr Asn
1235

<210> SEQ ID NO 15
<211> LENGTH: 1785
<212> TYPE: DNA
<213> ORGANISM: Chlorella variabilis

<400> SEQUENCE: 15

```
cgcgcctctg cggtggagga catccgcaag gtgctgtctg acagcagcag cccggtggcg      60
gggcagaagt acgactacat tctggtcggc ggcggcaccg cggcctgcgt gctggccaat     120
cgcctgtccg ccgacggctc caagcgtgtg ctggtgctgg aagccggccc cgacaacacc     180
tcgcgcgacg tcaagatccc cgccgccatc acccgcctct ccgcagccc cctcgactgg      240
aacctcttct ccgagctgca ggagcagctg gcggagcgcc agatctacat ggcgcgcggc     300
cggctgctgg gcggcagcag cgccaccaat gccacgctgt accaccgcgg cgcggcgggc     360
gactatgatg cctggggcgt ggagggctgg agctcggagg acgtgctcag ctggtttgtg     420
caggcggaga ccaacgccga cttttggccct ggcgcgtacc acggcagcgg cggccctatg     480
cgtgtcgaga acccacgcta caccaacaag cagctgcaca ccgccttctt caaggccgca     540
gaggaggtgg ggcttacccc aaacagcgat ttcaacgact ggagccacga tcatgctggg     600
tacggtacct tccaggtcat gcaggacaag ggcacacgtg ccgacatgta ccggcagtac     660
ctcaagcccg tgctgggccg cagaaacctg caggtgctga ccggcgcggc cgtgaccaag     720
gtcaacattg accaggctgc aggcaaggcg caggctctgg tgtggagtt ctcaaccgac      780
gggcccacag gtgagcggct gagcgctgag ctggcgccag gcggcgaggt gatcatgtgt     840
gccgcgcgcc tgcacacgcc cttcctgctc aagcacagcg gcgtggggcc ctcggcggag     900
ctcaaggagt ttggcatccc ggtggtttcc aacctggcag gtgtgggtca gaacctgcag     960
gaccagcccg cctgcctgac cgcggcgccg gtcaaggaaa agtatgatgg catcgccatc    1020
agcgaccaca tctacaacga aagggccag atccgcaagc gcgccattgc cagctacctg     1080
ctgggcggcc gcgcggcct cacatccacc ggatgcgacc gcggcgcctt tgtgcgcacg    1140
gcaggccagg cgctgccaga tctgcaggtg cgctttgtgc cgggcatggc gctggacccg    1200
gatggcgtgt ccacgtatgt gcgctttgcc aagttccagt cccagggggct caagtggccc    1260
agcggcatca ccatgcagct gatcgcctgc cgcccgcaaa gcacgggcag cgtgggcctc    1320
aagagtgccg accccttttgc gccgcccaag ctgagcccccg gctatctgac ggacaaggac    1380
ggcgctgacc tggccacgct ccgcaagggc atccactggg cgcgcgacgt ggcgcgcagc    1440
agcgcgctca gcgagtacct ggatggcgag ctgttccccg gcagcggagt ggtgagcgat    1500
gatcagattg atgagtacat ccgccgcagc atccatagct ccaacgccat cacaggcaca    1560
tgcaagatgg gcaatgccgg cgacagcagc agcgtggtgg acaaccagct gcgggtgcac    1620
ggtgtggagg gcctgcgggt ggtggatgcc tcggtggtgc ccaagatccc aggtggccag    1680
acgggcgcgc cagtggtgat gattgcggag cgcgccgccg cgctgttgac tggcaaggcg    1740
acgatcgggg cgagcgctgc ggccccggcg acagtggcag catga                    1785
```

<210> SEQ ID NO 16
<211> LENGTH: 1743
<212> TYPE: DNA
<213> ORGANISM: Chlamydomonas reinhardtii

<400> SEQUENCE: 16

```
ctgtcggtgc gtgctgctgc gggcccagct ggctcggaga agttcgacta cgtgcttgtc    60
gggggtggca ctgcctcgtg cgtgcttgct aacaagctgt cggctgatgg aaacaagaag   120
gttctggttc tggaggctgg ccctaccggt gacgccatgg aggtggctgt gccgccggc    180 atcacccgct tgttcgcgca cccagtgatg gactggggca tgtcgtcgct gacacagaag   240
cagctggtgg cccgcgagat ctacctggcc cgcggccgca tgctgggcgg ctcctccggc   300
tctaacgcca cgctgtacca ccgcggcagc gccgccgact acgacgcttg gggcctggag   360
ggctggagca gtaaggacgt gctggactgg ttcgtcaagg cggagtgcta cgccgacggc   420
cccaagccct accacggcac tgggggcagc atgaacacgg agcagccgcg ctacgagaac   480
gtgctgcacg atgagttctt caaggccgcc gccgccaccg gcctgcccgc caaccccgat   540
ttcaacgact ggagccaccc gcaggacggc ttcggtgagt ccaggtgtc tcagaagaag    600 ggccagcgcg ccgacaccta ccgcacctac ctcaagcccg ccatggcgcg cggcaacctc   660
aaggtggtga ttggtgcccg ggccaccaag gtcaacattg agaagggctc gtcgggcgca   720
cgcacgaccg gcgtggagta cgccatgcag cagttcggcg accgcttcac cgccgagctg   780
gcccctggcg gcgaggtgct gatgtgctcg ggcgcggtgc acacgccgca cctgctcatg   840
ctgtcgggcg tgggccccgc cgccacgctg aaggagcacg gcatcgatgt ggtgtcggac   900
ctgtcgggtg tggggcagaa cctgcaggac caccccgcgg cggtgctggc ggcgcgcgcc   960
aagccagagt ttgagaagct gtcggtgacc agcgaggtgt atgacgacaa gtgcaacatc  1020
aagctgggcg ccgtggcgca gtacctgttc cagcgccgcg gcccgctggc caccaccggc  1080
tgcgaccacg gagccttcgt gcgcacctcc tcctcgctct cgcagcccga cctgcagatg  1140
cgcttcgtgc cgggctgcgc cctggacccc gatggcgtca gtcctacat cgtgtttggc   1200 gagctcaaga agcagggccg cgcatggccc ggcggcatca cgctgcagct gctggccatc  1260
cgcgccaaga gcaagggcag catcggcctg aaggcggctg acccgttcat caaccccgcc  1320
atcaacatca actacttctc cgaccccgcc gacctggcca cgctggtcaa cgccgtcaag  1380
atggcgcgca agatcgcggc gcaggagccg ctcaagaagt acctgcagga ggagacgttc  1440
cccggcgagc gcgcctccag cgacaaggac ctggaggagt acatccgccg caccgtgcac  1500
tcgggcaacg cgttggtggg caccgcggcc atgggcgcct cgcccgcggc cggcgccgtg  1560
gtgtcctccg ccgacctcaa ggtcttcggc gtggagggcc tgcgtgtggt ggacgcctcg  1620
gtgctgccgc gcatccccgg cggccagacc ggccgcgcca ctgtcatggt ggcggagcgc  1680
gcggcggcgc tgctgcgcgg ccaggccacc atcgcgccca ccgccagcc cgtggccgtg  1740 taa                                                                1743
```

<210> SEQ ID NO 17
<211> LENGTH: 1707
<212> TYPE: DNA
<213> ORGANISM: Phaeodactylum tricornutum

<400> SEQUENCE: 17

```
tacgactaca ttatctgcgg gggagggttg gctgggtgcg ttttggctga acgcctttcg    60
caggacgagt ccaagcgtgt gctcgtacta gaggctggcg gctcggacta caaaagtctt   120
ttcatcagga ttccggctgg agtcttacgg ctctttcgca gtaaatacga ttggcaacat   180
gaaacgggcg gtgaaaaggg ttgcaacgga cggaatgtgt ttttgcaacg cggcaagatt   240
ctcggcggat cttcgtgcac caatgtatgt ctgcatcacc gtgggtcagc ggaagattac   300
```

```
aacagctgga acattccccgg gtggacggct actgatgtgc ttcctttctt caagcaatcg    360
caaaaggatg agacgggccg ggatgccacg ttccacggtg cggatgggga gtgggtcatg    420
gatgaggtgc gataccaaaa tccattgagc aagttattcc tggaggtagg ggaggcagct    480
ggcctcggaa ccaatgatga tttcaacaac tggtcgcatc cgcaggatgg cgttgggcgc    540
ttccaggttt cagaagtaaa cggagaacga tgttcgggag ccacagcatt tctaagtaaa    600
gcggccaagc gctcaaatgt catagttcga actggcacta tggtgagaag gatcgacttt    660
gatgagacaa aaacagcgaa agggattacc tacgatttga tgggcgatga cacatgtacg    720
acatttcaag cttgtttgaa agagggtggc gaagtgctgg tgacaggtgg agcaattgca    780
tcccctcagc ttctcatgtg ctccggaatt ggacctggca agcacttacg gtcgctgggc    840
attccagtag tccacgacaa ctcggcagtt ggtgagaacc tgcaggatca cccagctgct    900
gtcgtttcct ttaaaacccc tcaaaaggga gtttctgtta cttctaaatt gcggctcttc    960
ggtaagacaa accccattcc agtcttccag tggctatttt ttaaaagtgg tcttttgacc   1020
tccactggat gcgatcatgg cgctttcgtt cggacatcgg attcactcga acaaccggac   1080
ttgcagatta gattcttggc agctcgcgct cttggacccg acggaatgac cacgtatacc   1140
aaattccgta cgatgaaaac agttgaagat ggttattcgt tccagagtgt tgcatgtcga   1200
gcaaaaagca agggaaggat tcggttatct tcgtccaact cgcacgtaaa gcctatgatt   1260
gatggcggat acctctctaa ccaggatgat cttgccacac tacgtgctgg tatcaagctt   1320
ggacgtatgc tcggtaaccg accggaatgg ggcgagtacc ttggtcaaga ggtgtatcca   1380
gggcagatg tgcaaacgga tgaagagatt gacgaataca ttcgtaactc gctccatacc   1440
gccaatgctt taacggggac atgcaaaatg gaacgggtc gtggggctgt tgttgggccc    1500
gatttacgtg taattgggt caatggtgta cgtgtggggg attcatctgt ttcccctgc    1560
attccagggg gacaaacggc aacaccgacc gtcatgatag gggatcgggc cgctgttttt   1620
gttcggcaac ccgtatccca gctgaacatt gaaattttca gagaaaaagg gggcacacat   1680
cctgggggcaa cgaccgcctc agcctag                                     1707
```

<210> SEQ ID NO 18
<211> LENGTH: 1758
<212> TYPE: DNA
<213> ORGANISM: Coccomyxa subellipsoidea

<400> SEQUENCE: 18

```
gcactgcggg tcagggcgat aatcaaaagc gacaatccag ctgcagataa gtatgacttc     60
atcctggtcg gcggcggcac agcaggctgc gtgctggcca acaggctgac agcagatgga    120
tccaagaagg tcctgctgct cgaggcggga ggcgccaaca aggcgcggga ggtacgcaca    180
ccggccgggc tgccgcgcct gttcaagagc gccctcgact ggaacctcta ctcctccctg    240
cagcaggcag ccagcgacag atcgatctac ctggcacggg aaagcttct gggtggcagc    300
tccgcaacta atgccacgct gtaccaccgg ggactgcgg cagactacga cgcgtggggt    360
gtgccggggt ggacctccca ggacgccctg cgctggttta ttcaggcaga gaacaactgc    420
agagggattg aggacggggt gcatgggacc ggggggattga tgcgcgtgga gaaccctcgc    480
tacaacaacc ccctgcacga ggtcttttttc caggcggcca agcaggccgg cctcccagag    540
aacgacaact ttaacaactg gggcagatca caggcggggt acgggagtt ccaggtgact    600
cacagcaagg gtgagcgcgc cgactgcttc cggatgtacc tggagccagt catggggcgt    660
tccaacctca cagtgctcac cggagccaaa acgctcaaaa tcgaaactga aaagtccggc    720
```

```
ggcgccacgg tctcgcgcgg cgtcaccttc caggtcaacg gccaggacgg cagcaagcac    780
tcagctgagc tggcggctgg cggcgaggtg gtgctgtgcg cggggtcaat ccactcgccc    840
cagatcctgc agctctccgg catcggcccc caggcggagc tgcgctccaa ggacatccct    900
gtcgtcgcag acctgcccgg cgtcggccag aatatgcagg accacccggc gtgcctgtca    960
gccttctacc tcaaagagag cgcgggtccc atcagtgtga ctgatgagtt gctgcacacc   1020
aatggccgaa tccgcgcgcg cgcaatccta agtacctgc tcttcaaaaa ggggcccctc   1080
gccaccacag gatgcgacca cggcgccttt gtgaagactg caggtcagag tgagccggac   1140
ctgcagatcc gctttgtgcc gggtctggcg cttgaccctg acggcatcgg atcctacacg   1200
gcctttggca agatgaagga ccagaagtgg ccctccggaa tcaccttcca gctgctcgga   1260
gtgcggccca gagccgcgg tcggtgggt cttcgcagcg acgaccctg ggacgcgcca   1320 aaactggaca tcggcttcct gactgacaag gagggcgctg acctggccac gctgaggagc   1380
ggcatcaagc tctcgcgcga gatcgcacg gagccggcat tcggagcata tgtaggcaac   1440
gaacttcacc cgggcgcagc cgcctcgtcc gattctgcga tcgactcatt catccgtgac   1500
acggtgcact cgggcaatgc caacgtgggc acatgctcga tggggtgaa tgggaacgcc   1560 gtcgtggacc cgtcactcag agtgttcggc atccgcggcc tgcgagtggc cgacgcatca   1620
gtcatccccg tcatcccagg aggccagacc ggcgctgcaa cggtgatggt ggcagagagg   1680
gccgcggaga ttctcctcgg ctcgaaccag aagcagccgg ccgccgccgt ccccgccgcg   1740
cagccggccc tggcttga                                                 1758
```

<210> SEQ ID NO 19
<211> LENGTH: 1744
<212> TYPE: DNA
<213> ORGANISM: Volvox carteri

<400> SEQUENCE: 19

```
tccagttgca gtcaaagctg cggcaagcgt ggggtcggag aagttcgact acatccttgt     60
gggaggaggg acggcaggtt gcgttctggc aaacaaattg tccgctaatg gcagcaagaa    120
ggttcttgtt cttgaggctg gtccaaccgg cgatgctatg gaagtggccg taccggccgg    180
tattgcccgt ctctttgcac atccagtttt tgactggggt atgtccagtt gacgcagca    240 gcagctggtt gcacgcgaga tctaccttgc tcgcggtcgc cttctgggcg gttcctctgg    300
gaccaacgca acgctgtatc atcgcggcac ccccgctgac tacgacagtt ggggcttgga    360
gggctggacg agcaaggatc tacttgattg gttcgttaag gccgaatgct atggagacgg    420
tccccgggcc ttccatggcc agtccggttc tatgaatgtg gagcaaccgc gttaccagaa    480
cgtcctgcac gacgagtttt tcagggctgc tgcggcagct ggattacctg ccaacgagga    540
tttcaatgac tggagccggc cgcaggaggg ctatgggag ttccaggtgg cccagaagaa    600
cggtgagcgc gcgacacgt atcggaccta cctcaagccg gctatgggcc gcgacaacct    660
gaaggtgatg accggcgcgc gtacgaccaa agtgcatatc gagaagagct cgacgggtcc    720
acgtgcccgc ggtgtcgagt atgctaccca gcaatttggg gagcgctaca ccgccgagct    780
gactcctggt ggcgaggttc tcatgtgcac cggtgccgtg cacacaccgc acctactgat    840
gctttcgggc attgggccgg cgccgaccct ccttgagcac ggactcgacg tgatatcaag    900
cctgcctggc gtgggtgcca acctgcagga tcacccagcc gcggtgcttg ctgtccgggc    960
taagcccgag ttcgagggac tgtcggtcac ttcggaaatc tatgacagca agtgcaacat   1020
```

| | |
|---|---:|
| ccggttgggc gccgttatga agtacctgtt cggacgccgc gggccacttg caaccacagg | 1080 |
| ctgtgatcat ggcgcttttg tgcgcacttc ggcctcgcat tcgcagccgg acctgcagat | 1140 |
| gcgattcgtg cccggttgcg cgctggaccc cgacggcgtg aagtcgtaca ttgtgttcgg | 1200 |
| cgagctgaag aagcagggcc gtgcttggcc cggcggtatc acgttgcagc tgctgggcat | 1260 |
| ccgcgccaag agcaggggca gcatcggtct caaggccgcg gatcccttca tcaaccccgc | 1320 |
| cattaacata aactatttct ccgatcctga ggaccttgcc acgcttaaga acggtgtgcg | 1380 |
| cattgcgcgc gaaatcgttg cccaggagcc attgcgcaaa taccttctgg aggagacctt | 1440 |
| ccccggggag cgggcgaaca ctgacaagga cattgaggag tatgtccggc gcacggtcca | 1500 |
| cagcggcaac gcgcttgtgg gcacctgcgc gatgggtacc acgccagcca gtggcgccgt | 1560 |
| ggtgtcttct gctgacctca aggtgttcgg tgttgacggg ctgcgtgtcg tggatgcgtc | 1620 |
| tgtgctgcca cgcattccag gcgggcaaac aggagcggcc actgtcatgg ttgcagagcg | 1680 |
| ggcggcggcc atgctgcttg gacaggcgac gattacttct cgtcgcgagc ctgcggctgt | 1740 |
| ttag | 1744 |

<210> SEQ ID NO 20
<211> LENGTH: 1674
<212> TYPE: DNA
<213> ORGANISM: Ectocarpus siliculosus

<400> SEQUENCE: 20

| | |
|---|---:|
| gtgcctgcag cacgttatgc gacgtcttcg gtgagcatgt cggtggcgga agaaggccac | 60 |
| aagttcatca tcatcggcgg gggtacggct gggtgtgttc tggcgaaccg cctctctgcc | 120 |
| gacaaggaca attcagtgct ggtgttggag gccggctcgg aaaaattcaa tgacaggaat | 180 |
| atcaagatgc ccatcgcaat cctaaggttg ttcaagtctg tcttcgactg gggcttccag | 240 |
| tcggaaaacg agaagtttgc caccggcgac ggcatctacc tctgccgtgg caaggtcctc | 300 |
| ggcgggtcta gctgcaccaa cgtcatgctt taccatcgcg gagaggaggc tgactatgac | 360 |
| gcgtgggggg tggatggatg gaaaggcaag gacgtgctcc cctacttcaa gaaggcggag | 420 |
| aacaaccgat ccaagaaaaa gggggagttc cacggcaagg gaggcctgat gcaggtggaa | 480 |
| aacgcgcgtt acatgaaccc tttgacgaag ttgttcttca aggcgtgcga gcaggcaggc | 540 |
| ctgtcggaga cgaggactt caacgattgg tcccactcgc aggagggctt cggtcgcttc | 600 |
| caggttgcac agaagagagg caagcgctgt tcggcagcct cctcctacct caaggaagcc | 660 |
| atggggcgca aaaacctgga cgtgcagacc agcgcccaga tcaccaaggt cttgatcgag | 720 |
| aacggcggtg ccataggcgt tgagtacgtg cgggatggcg aaaagaagat cgccaagctt | 780 |
| gccgtgggcg gagagatcct gctagcagga ggtgccatca gctcaccgca ggtgctgatg | 840 |
| ctcagtgggg tgggtccggc cgagcacttg aggtccaagg gcatcgaggt gaagagcaat | 900 |
| gtgcctgggg tcggaaagaa cctccgcgac catcccgctg tcaccgtgat ggccgacatc | 960 |
| aacaagccta tctccatcac cgacaaggtt ctcaaggagg gctctgggga cgtgaacaaa | 1020 |
| attacggccc ttcagtggct gttgacggga actgggccgc tgacctcgcc agggtgcgag | 1080 |
| aacgcgcgt tcttcaagac cacgcctgac aaagcggcgg cagatctgca gttgcgattt | 1140 |
| gtccctggaa gatccactac cccagacggg gtgaaggcgt acaacactat tggcaccaag | 1200 |
| ggaggcctc cttcgggtgt caccgtgcag gtggtgggga tccggccgca gagtgaaggc | 1260 |
| cacgtcgagc tgcgttcttc ggaccccgttc gacaagccac acatcgtcac taactacctt | 1320 |
| gagagtgggg aggacatggc gtctttgacg aacggaatcg aaatggcacg aaagctgttc | 1380 |

```
gaccaggagg ccttcggaga aatggtggac aaagaagtct tccccggcag agacaacaag    1440
gagatctcgg agtacatcaa gtctaccgtg cactccgcca acgccttggt tggcacttgc    1500
aagatgggcg aagaatcaga acacatgtct gttgtgaact cggcactcaa ggtaaagggt    1560
gttgccgggc tgagggtgat cgattcttcg gtgatgcctt caatcccggg cggtcaaaca    1620
gcggcaccga cgatcatgat cgcagagaaa gcggcggaca tgctcatggc ttag          1674
```

<210> SEQ ID NO 21
<211> LENGTH: 1808
<212> TYPE: DNA
<213> ORGANISM: Emiliania huxleyi

<400> SEQUENCE: 21

```
gccttcgcgg cggcagcggc gtcactggcg gcagcctcgg ccgcggcggc ggctcgccgg      60
cgatcgacgg cgagtttgac tacatcatcg ttggaggcgg cgccgcgggc tgcgtgctcg    120
ccaatcggct gagcgccgac ccggcgcacc gggtgctgct gatcgaggcc ggaggcgacg    180
cgtcgcgcga caagcgtgcg caggtgccgt gggccttcac caagctgctg cgttccgagt    240
acgactggga ctttcacgtg gaggcggagg cggcggtgaa ccagcaggag gtgtacctct    300
gccgcggcaa ggcgctgggc ggctcttcgg tcacaaacgt gatgctctac caccggggca    360
gccccgcgga ctacgacgct tgggaggagg ctggcgcgcg agggtggggc gcgaaggacg    420
tgctcccgta ttacctccgc gtcgaggact acggcgacgg cgcctcgcag taccacgccg    480
tcggcgggca cgtctcggtg caggaggtgc cgtaccagaa ccaactctcg gcaaccttcc    540
tgcgggcgat ggggcagctg ggcttccggc cgaacggaga cttcaacgac tggtccagcc    600
cgcaggaggg gtacgccgcc tacaaggtga cccagcgggc cggccgccgc tgcaccgctg    660
ccgacggcta cctggcggcg gcgagagagc gcgcgaacct ggtggtggtg accggcgcgc    720
aggcgacccg cctcgccctc gacagtgcgt acgacggcgc gggccggctg caggtctccg    780
gcgtcgagtt tgcacgcggc gacgagcgcg agccgtgctc cgtccggctc gcgcgcggcg    840
gagaggccgt cctctgcgcc ggcgcggtcc agacgccgca cttgctgctc ctctccggga    900
tcggcccggc ggagcacctg cgcgaggttg gcgtgccggt gcgggcggac ctgcctgggg    960
tggggtccgg cctgcaggac cacccgcgcg tggtcgtctc gtacgagagc aagaaagcgg   1020
tcgccgcgac ggacgacgcg ctcctcaagg gctacgcgtc gctggtcaac ccgctcgcga   1080
tgctgcgctg gctcctgttt gggcgcgggc cgctggcgtg cgccgcgtgc gaccacggcg   1140
gcttcgtccg ctcctcgccc gacctcgacc agcccgacgt ccagatccgc ttcgtgcctg   1200
cgcgcgcctc gtccgcctcc gggatgaaca cgctgatcga gctgggcagg agagcgcgct   1260
tcctgccggg cttctcgacg caggtcgtcg cttgccgccc gcggagcgag gggcgcgtgc   1320
ggctgcggtc ggccgacccg ttcgccaagc cgatcatcga gggcatccac ttgggcgcag   1380
cggaggacgt cgccgtcgtg cgccacggca tccggctcgg ccggcaggtt tgcgccgcgg   1440
cagccttcga cgagtaccgc ggagaggagg tcttccccgg cgcggcggtg cagtccgacg   1500
agcagatcga cgagtacatc cgctcgtcgg tgcactctgc gaacgcgctc acctcgtcct   1560
gccgcatggg cgacccgtcc gacccggccg cagtcctcga ctcccacttg cgcgtgcgcg   1620
gcgtcggcgg cttgcgcgtg gccgacgcct ccgccatgcc tcgcatcatc ggagggcaga   1680
cgcaggcgcc cacgtacatg ctcgccgaac gtgccgccga catcctgctg cacgcgcgcc   1740
tgcaggcgca cgagccagcc accgagagcg tctcgcagcg gctcgaggtt gcggcggccg   1800
``` cactctag 1808

<210> SEQ ID NO 22
<211> LENGTH: 1605
<212> TYPE: DNA
<213> ORGANISM: Aureococcus anophagefferens

<400> SEQUENCE: 22

```
cgcctcagcg aggacccgag caagaaggtg ctcgtgctcg aggccggcga ccggggcccg      60
aactcgccgc tcgtgaagat ccccgtggcc atcctcaagc tcttcaagtc cgcgtacgat     120
tggaacttcg cgacgaggcc gtccgaggcc gtcgcggacc ggagcctcta cgtctgccgg     180
ggcaagggcc tgggcggcag ctccctgacg aacgtcatgc tctacaaccg gggctcggcc     240
aacgactacg acgcgtgggc ggccgcgtgc ggcgacgact cgtgggggc ggaagagatg     300
ctcggctact tcaagaaggc cgaggactgc ctcgtgccgg cgcaccgagc gaaccactac     360
cacggcgtcg gcgggcccta cgcgtcgagc cacgtgccct acacgaacga gatgtcgacg     420
gcgttcgtcg aggccgccgt cgaggacggc ggcgtgcgca acgcgactt caacgactgg     480
tccacgtccc aggtcggctt cggccgcttc gccgtgagcc agcgcaaggg ggcaagggtg     540
gacgcggcga cggcctacct cccgcggaag gtccggcggc gcgcgaactt ggacgtggtc     600
cgcggcgcgg cgctctccgg cgtcacgtgg aacgcgaaca aggccacggg cgtcgagttc     660
gccttcggcg gcgtctcggg catcgcctgc ggcggcgagg tgatcctctc cggcggcgcg     720
gtccactcgc cgcagatgct catgctctcc ggcgtcggcg cgaaagcgca gctcgaggag     780
ttcggcatcc ccgtcgtcgc ggaccggccg ggcgtgggca agaatttgca ggaccacccg     840
gcctgcctcg tgtcctggcg cgggtcggcc aaggcccagg gcaagagcca ctcgacgcag     900
ctccggatcc ccgggacgac gaagacctcg cccaaggcgc tcctccagtg gctcttcctc     960
ggccggggcc ccttggcctc gccgggctgc gaccacggcg gcttcgccaa ggtcggcgcc    1020
ggcgacggcg actgcgacgt ccagttccgg ttcctcgcga cgaagtcgat cacgcccgac    1080
ggcatgtcta ccatctccga ctcctacgag gccgccgtgg accaccccga cggcttgacg    1140
atccagacca tcgtcgcccg gcccaagagc cgcgcggggc aggtgaaact cgcgtcccgg    1200
gacccggcgg cgaagcccgt catcgagaac gcgtacctct ccgacgaggc cgacgtcatg    1260
accatggtca aggcgctcca gaaggcgcgg tccatcgcga gccgggcgcc gttgagcgcc    1320
tacgcgggac acgaggagtt cccggggaag gacgtcgcgg acgagcgcca actggcggcc    1380
tacgtgcgga acaccgctca taccgcgaac gcggtcgtcg ggacctgcaa gatgggcgag    1440
tccagcgacg ccctcgccgt cgtcgacaac cacctcaagg tcatcggcgt ctcgaacctg    1500
cgggtggtgg acgcgtcggt gatgccgacg ctgccgggcg ccagacggc cgcgtcgacc    1560
gtcgcgctcg cggagaaggc cgcggacctc atcaagggg gctga                     1605
```

<210> SEQ ID NO 23
<211> LENGTH: 3711
<212> TYPE: DNA
<213> ORGANISM: Nannochloropsis gaditana

<400> SEQUENCE: 23

```
ctctccaaga ccaccatcgg cctccaatcc ttcgtgacag caattatgg agtgaggaga       60
gcaatctctc tccgagggg gctacaatct gtttcgatga aggcaccggc tgccgttgct     120
tcgtccacct acgactacat catagtcggt ggcggcatcg gcggttgtgt tctcgccaac    180
cgactgacag aaagcgggcg tttcaaggtc cttctcctgg aggccggaaa atcagcagag    240
```

```
cgaaacccgt acgtgaacat ccccgcgggc gtggtccgcc tctttaaatc ggccttggat    300
tggcagtttg agagcgcccc cgaaagacac ctgacgggga aggaggtgta cttggtcagg    360 ggggaaggcca tgggaggctc cagtgcggtg aatgtgatgc tcgtacaccg cggctcggcc   420
tccgactacg cgaagtggga ggcggaggga gctcagggat ggggcccgga ggaagcctta   480
cgctacttca agaaaatgga agacaacttg gtgggcgggg aagggcggtg gcacggccag   540
gggggcatgt acccggtgga cgacgtcaag taccaaaacc ctttgtccaa gcgctttta    600 caggcgtgcg aggagtacgg gtggcgggcg aacccggatt ttaacgactg gtcccatccc   660
caggacggat acgggagctt caaagtggcg cagaagcacg gcaaacgggt gacggccgcc   720
tccgggtact tgaacaaggc cgttcgacgt cgaccaaacc tagacattct gtcagaggcc   780
cttgtgaccc gggttttgct tgagggagag ggggatgtga aggcggtcgg ggtggagttc    840
acgggcaaag atgggaagac gcaccaggtt cggaccacgg ggaaggcggg agaagttctc    900
ttggcgggcg cgcgggtcaa cagcccccaa ctcctgatgc tgagtgggat cggacccgag    960
gcagacctcc aggcagtagg catcgcgacc aaagtaaacc gtccgggcgt gggggagaac    1020
ttgcaagacc atcccgccgt cactattgcg cacaacatca cgcgccctat ctcgctctgc    1080
gacgacctct tccttttcca cacacctgtc cctaagcccc accaggtgct ccggtggacc    1140
ttgaccggat cgggccccgct gaccacccca ggctgcgacc acggcgcgtt cctgaagacc   1200
cgagaagacc tccaggaacc caacgtacag tttcgtttca tagccgggcg gggttcggac    1260
cctgacggcg tgcgctccta catcatggga ggctcagcac gccccctgtc gggattgacg    1320
cttcaagtcg tcaacatccg ccccaaaagc aaagggaagc tgaccttggc gagcaaggac    1380
ccgttgaaga agccccggat cgaagtccgg tacttgtccg cggccgaaga cttgcaggcc    1440
cttcgcacgg gcatgaggat tggccgggat ctgatcaagc aacgggcttt tgcggatatc   1500
ttggacgagg aagtgttccc ggggcccgcc gctcagacgg acgaggaact ggacgcctac    1560
atccgggata gcttgcacac ggccaacgcc ctggtaggca cctgcaagat ggggagtgtg    1620
gaggatcgga acgcagtggt ggacccgag tgccgggtca tcggcgtggg aggcctgcgg    1680
gtggtggatg caagcgtgat gcccgttatc cccggagggc aaacgggaag tggcacgacc    1740
atgctggccg aaaaagcggc cgacctggtc agggcccacg ctgggatttt ggtggagatg    1800
ggagtgcaag atgaggagag gaagggagga tggtttaacg gcctgttagg gcgcaaacag    1860
aaggtggcga cagaaaagga gcgaggcgaa cgtggtaaaa gcgaacgatt tgtttctgag    1920
gtgattaggc atatgggtcg ggttttcgta caagtttcga gggcaaggcg tgcgcaaacg    1980
tgcatgaggg tagggaaggg tctcgatagg aacggcagt tggagtgtgc catgcgcaag    2040
gaattgacga ttgcgctttt ttacgcaatg ctttttacaa tgagacatag tggatttctt    2100
tcgacgactg gtcgcgcctc atataaggac cttggatact tgacagggtc ctgtcgcgcc    2160 caccccttgta catctccatc ctccttgtgc ctgtttccag aaaaaccttt catgaagcta    2220
agccctgctt tggcggtcgt tggcttttgc tttaattcta tcaatgtcca aggtttccta    2280
ctcagcaacc ttgccggtcg gagcctgaag catccggtcc cacaaaaggg cttgtatagt   2340
cgcattgagt acgatgcacg ggagccacgt ctcgatgaat tcggcctccc tcttgatccg    2400
gcggatttga tggaaaaacc ccgagtgccc ctgaaggacc gagtttatca catcattgac    2460
atgacaaacg actgggtcga tgctgtgagc cgcggacggc gagaggagga gacgcgtcgc    2520
atcatccaac gacgtcgtgc cgctgccaag gccatggcaa tcaaggacaa ggtcttgatt   2580
```

```
tctcttgact acgtcttcca tccagtcaag gcctggagga ccttcgtggc ggaccccttg   2640
gaagcacggc atcagcgcca gctgcgtcag caggcagaaa agcgagcgag actagaacgg   2700
tatctgcaac gctataacac ggtcaagaat cgcttccatg atactctgga tcttttggag   2760
tcgacgaccc ggacatcggt gaaagtggcc aagtccgtga gttccgcagt ggtgggggcg   2820
cctgggacgg tgacgcggac cgtgaaggag gtgaaaagcc aggcacaggg cacagcggag   2880
gcagtggcga aggtgtcttc ctccgtctcc tcggtggtgt ccaagatcac gtcggtgatc   2940
aggaaggaag acggggctct ggcggggggcc aaggggaaaa aggacccgag atcagaagac   3000
gaaggaaaag ccgatccagt caaggtccgg gagatctggg aaacgaaaga gcagaccgcg   3060
attcgcacca tctgggaagc ggatgagctt gtcacgccgg taacaccgcc agccacggct   3120
atggcgtcga cggtttcggt gtcagagcct caggacgaga acgaagcttc catctctcag   3180
ggagcggcgc cttcccccag cacctcatca ccatcctccc ccgagcccgt cacacgcctc   3240
tctttccggg cacgtgtgga ggcggacgag aaggaacgct ttgggtcccg aagattgaag   3300
atatcgggga atgtcccgcc gaccgcttct cccactcggg gggcttcttc tctcccttttg   3360 gacacgcttt cctcctccgc cacccaaacc tttgagcgtt ccaaagtggg gccgcccata   3420
cgaacaagta aggcgagatg cattggaaaa tgtgtacata acgggtggaa agggatatgt   3480
gaggaatggt ttgtgcacat tagttttcca acgtatgcgg tctctatcgt ccgtccaccc   3540
atgcacgtgc ataattttaa agtgatttgt tgtgttctag cggtccgaca tgcaagaagg   3600
aagaaggaga tgagcacggc tttatctaca catttaattt atttactgct gaaaacggta   3660 aaatgttgc aagatcttcc ccagctacgg agaaagggca aacaaacta g               3711
```

<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24

```
atggcgtcaa ttacatcgcg                                                20
```

<210> SEQ ID NO 25
<211> LENGTH: 18
<212> TYPE: DNA
<213> ORGANISM: artificial sequence
<220> FEATURE:
<223> OTHER INFORMATION: Primer

<400> SEQUENCE: 25

```
tcatgctgcc actgtcgc                                                  18
```

<210> SEQ ID NO 26
<211> LENGTH: 15
<212> TYPE: PRT
<213> ORGANISM: artificial sequence
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (4)..(7)
<223> OTHER INFORMATION: X is any amino acid
<220> FEATURE:
<221> NAME/KEY: MISC_FEATURE

```
<222> LOCATION: (9)..(9)
<223> OTHER INFORMATION: X is D or E
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (12)..(12)
<223> OTHER INFORMATION: X is A or G
<220> FEATURE:
<221> NAME/KEY: MISC_FEATURE
<222> LOCATION: (14)..(14)
<223> OTHER INFORMATION: X is any amino acid
<220> FEATURE:
<221> NAME/KEY: MISC_FEATURE
<222> LOCATION: (15)..(15)
<223> OTHER INFORMATION: X is K, R, S or E

<400> SEQUENCE: 26

Gly Xaa Leu Xaa Xaa Xaa Xaa Cys Xaa Xaa Gly Xaa Phe Xaa Xaa
1               5                   10                  15

<210> SEQ ID NO 27
<211> LENGTH: 37
<212> TYPE: DNA
<213> ORGANISM: artificial sequence
<220> FEATURE:
<223> OTHER INFORMATION: primer

<400> SEQUENCE: 27
ctgtacttcc aatcagccag cgcagttgaa gatattc                      37

<210> SEQ ID NO 28
<211> LENGTH: 41
<212> TYPE: DNA
<213> ORGANISM: artificial sequence
<220> FEATURE:
<223> OTHER INFORMATION: primer

<400> SEQUENCE: 28
tatccacctt tactgttatc atgctgcaac ggttgccggt g                 41

<210> SEQ ID NO 29
<211> LENGTH: 33
<212> TYPE: DNA
<213> ORGANISM: artificial sequence
<220> FEATURE:
<223> OTHER INFORMATION: primer

<400> SEQUENCE: 29
tacttccaat caatgatgct gggtccgaaa acc                          33

<210> SEQ ID NO 30
<211> LENGTH: 41
<212> TYPE: DNA
<213> ORGANISM: artificial sequence
<220> FEATURE:
<223> OTHER INFORMATION: primer

<400> SEQUENCE: 30
tatccacctt tactgttcta ctaaactgca accggctgac g                 41

<210> SEQ ID NO 31
<211> LENGTH: 33
<212> TYPE: DNA
<213> ORGANISM: artificial sequence
<220> FEATURE:
<223> OTHER INFORMATION: primer
```

```
<400> SEQUENCE: 31
tacttccaat caatgaaaaa aagcctgcgt agc                           33

<210> SEQ ID NO 32
<211> LENGTH: 36
<212> TYPE: DNA
<213> ORGANISM: artificial sequence
<220> FEATURE:
<223> OTHER INFORMATION: primer

<400> SEQUENCE: 32
tatccacctt tactgttcta ctatgcgctt gcggtg                        36
```

FATTY ACID DECARBOXYLASE AND ITS USES

CROSS-REFERENCE TO RELATED APPLICATION

This application is the U.S. national stage application of International Patent Application No. PCT/EP2017/062061, filed May 19, 2017.

The Sequence Listing for this application is labeled "Seq-List.txt" which was created on Oct. 16, 2018 and is 98 KB. The entire content of the sequence listing is incorporated herein by reference in its entirety.

FIELD OF THE INVENTION

The present invention relates to the field of the enzymology, in particular to fatty acid decarboxylase.

BACKGROUND OF THE INVENTION

Alkanes and alkenes are major components of fossil fuels but they also occur naturally in plants, insects, cyanobacteria and some bacteria. Diatoms and the colonial Chlorophyceae *Botryococcus braunii* are also known to produce alka(e)nes with more than 21 carbons.

Most alka(e)ne biosynthetic pathways involve the conversion of activated fatty acids (acyl-ACPs or acyl-CoAs) to an aldehyde intermediate and the final decarbonylation to alka(e)ne. These reactions are catalyzed by a variety of enzymes. In plants, very long chain alkanes from 27 to 33 carbons are produced from fatty acids by the action of two homologous putative oxidoreductases ECERIFERUM1 (CER1) and ECERIFERUM3 (CER3) (Bernard et al., 2012, *The Plant Cell*, 24(7), 3106-18; Bourdenx et al., 2011, *Plant Physiology*, 156(1), 29-45). In insects, synthesis of cuticular alka(e)nes from 21 to 37 carbons involves an acyl-ester reductase and a cytochrome P450 (Qiu et al., 2012, *PNAS*, 109, 14858-14863). In Cyanobacteria, the pathway is composed of an acyl-ACP reductase and an aldehyde deformylating oxygenase (Li et al., 2012, *Biochemistry*, 51(40), 7908-16; Rude et al., 2011, *Applied and Environmental Microbiology*, 77(5), 1718-27). Only the bacteria *Jeotgalicoccus* spp and *Pseudomonas* sp are able to produce hydrocarbons by direct decarboxylation of free fatty acids (Grant et al 2015, *Journal of the American Chemical Society*, 137(15), 4940-3; Rui et al., 2014, *PNAS*, 111, 18237-18242; Rude et al., 2011, *Applied and Environmental Microbiology*, 77(5), 1718-27). However these bacterial fatty acid decarboxylases can produce alkenes (bearing terminal unsaturations) but not alkanes. In microalgae, no enzyme catalyzing the synthesis of hydrocarbons is known. Attempts have been made to purify the alkane synthesis system of the microalga *Botryococcus braunii* and it has been suggested that the synthesis proceeds through decarbonylation of a fatty aldehyde intermediate by a cobalt-porphyrin enzyme (Dennis & Kolattukudy, 1992, *PNAS*, 89(12), 5306-10). However, the protein has never been identified.

Therefore, there is still a strong need of enzymes suitable for producing alkanes/alkenes from fatty acids.

SUMMARY OF THE INVENTION

The present invention relates to the identification of a new class of enzymes for the synthesis of alkanes and alkenes, which was identified in microalgae. It is the first time that an alkane synthase is identified in these microorganisms. The enzyme catalyzes the conversion of free fatty acids into alkanes and/or alkenes by decarboxylation. The enzyme belongs to a superfamily of FAD-dependent proteins present in prokaryotes and eukaryotes (GMC (Glucose-Methanol-Choline) oxidoreductases) and which includes various enzymes (mainly alcohol oxidases). So far, no GMC oxidoreductase from microalgae has been characterized from a biochemical point of view and no other member of the GMC oxidoreductase superfamily has been identified as an alkane synthase. So this is a new enzyme for the synthesis of alkanes and alkenes with applications in biofuels, green chemistry, diagnosis and nutrition.

Accordingly, the present invention relates to the use of a polypeptide or a cell expressing said polypeptide for producing alkanes and/or alkenes from fatty acids, wherein the polypeptide has a fatty acid decarboxylase activity and comprises a sequence having at least 40% of identity with SEQ ID No 1.

Preferably, the polypeptide comprises the consensus sequence G-X-L-(X)$_4$-C-[D/E]-X-G-[A/G]-F-X-[K/R] (SEQ ID No 4), X being any amino acid. Alternatively or in addition, one, two, three, four, five or six amino acids in positions C372, R391, Y406, Q426, H512 and N515 of SEQ ID No 1 are conserved. Alternatively or in addition, at least 40% of the amino acid residues between positions 388-428 are hydrophobic residues selected from the groups consisting of V, I, L, M, F, W, C A and Y.

In a more specific embodiment, the polypeptide comprises or essentially consists in an amino acid sequence selected from the group consisting of SEQ ID Nos 1-3 and 5-14 and amino acid sequences having at least 80% of identity with one of them.

Preferably, the polypeptide is from algae, preferably microalgae or cyanobacteria.

Preferably, the fatty acids and the corresponding decarboxylated alkanes and/or alkenes comprise from 8 to 24 carbon atoms preferably from 12 to 22 carbon atoms.

Optionally, the fatty acids and the corresponding decarboxylated alkanes and/or alkenes are substituted and/or interrupted by one or several functional groups. Preferably, the fatty acids and the corresponding decarboxylated alkanes and/or alkenes are substituted by one or several groups such as an hydroxyl, a $C_1$-$C_3$ alcohol, a $C_1$-$C_3$ acyl, a $C_1$-$C_3$ ester, a $C_1$-$C_3$ amine, an amino group, a $C_1$-$C_3$ amide, a carboxyl, an aldehyde, an epoxy, an halogen, a $C_1$-$C_3$ alkoxy, a $C_1$-$C_3$ thioalkyl, a $C_1$-$C_3$ imine, a nitrile, a sulfur group such as $C_1$-$C_3$ sulfone or $C_1$-$C_3$ sulfoxide, a thiol, a nitro, a cyano, a $C_1$-$C_3$ halogenoalkyl, or may be interrupted by an heteroatom such as O, N or S, an acetylenic group, an ether such as a divinyl ether group, or an oxo group.

The present invention also relates to a method for producing alkanes and/or alkenes from fatty acids, wherein a polypeptide as defined above is contacted with fatty acids and submitted to light in presence of the FAD cofactor of the polypeptide. Preferably, the light has a wavelength between 300 and 540 nm, more preferably between 400 and 520 nm. For instance, the light is a white light or any light containing blue or UV photons (e.g. from 400 to 520 nm).

The present invention further relates to a recombinant host cell comprising a nucleic acid sequence encoding a heterologous polypeptide as defined above. Preferably, the host cell is a bacterium, a microalgae, a filamentous fungus or a yeast.

In a first embodiment, the heterologous polypeptide is co-expressed with a thioesterase, preferably in a microalga, a cyanobacteria or *E. coli*. In another embodiment, the heterologous polypeptide is co-expressed with a lipase, preferably in a bacterium or a microalga.

The present invention relates to a method for producing alkanes and/or alkenes from fatty acids, wherein a recombinant host cell according to the present invention is cultured and the alkanes and/or alkenes were recovered.

In addition, the present invention relates to the use of a polypeptide as defined above for dosage of free fatty acids in a sample. More particularly, the method for dosing free fatty acids in a sample comprises (a) contacting the sample with a fatty acid decarboxylase of the present invention in conditions suitable for converting fatty acids into alkanes/alkenes, (b) recovering the alkanes/alkenes and/or $CO_2$; and (c) quantifying the alkanes/alkenes and/or $CO_2$. Alternatively, the method for dosing free fatty acids in a sample comprises (a) contacting the sample with a fatty acid decarboxylase of the present invention in conditions suitable for converting fatty acids into alkanes/alkenes, and (b) measuring the fluorescence emitted by the fatty acid decarboxylase. Optionally, the method comprises a previous step of contacting the sample with a lipase, in particular in conditions suitable for converting fatty acids into free fatty acids.

The present invention also relates to the use of a polypeptide as defined above for decarboxylation of fatty acids.

DETAILED DESCRIPTION OF THE INVENTION

The inventors identified a new class of enzymes capable of converting free fatty acids into alkanes and alkenes by an activity of fatty acid decarboxylation.

Definitions

About: When used herein, "about" means more or less 10%, preferably more or less 5%. For instance, about 100 means between 90 and 110, preferably between 95 and 105.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof. The genetic code can be optimized for the host cell.

Control sequences: The term "control sequences" means nucleic acid sequences necessary for expression of a polynucleotide encoding an enzyme of the present invention. Control sequences may be native (i.e., from the same gene) or heterologous (i.e., from a different gene and/or a different species) to the polynucleotide encoding the enzyme. Preferably, control sequences are heterologous. Well-known control sequences and currently used by the person skilled in the art will be preferred. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding the enzyme. The functional combination of control sequences and coding sequences can be referred as expression cassette.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding the enzyme of the invention and is operably linked to control sequences that provide for its expression. Then the expression vector comprises an expression cassette suitable for expressing the enzyme of the invention.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance).

Recombinant: Recombinant refers to a nucleic acid construct, a vector and a protein produced by genetic engineering.

Heterologous: in the context of a host cell, a vector or a nucleic acid construct, it designates a coding sequence for the enzyme introduced into the host cell, the vector or the nucleic acid construct by genetic engineering. In the context of a host cell, it means that the coding sequence for the enzyme originates from a source different from the cell in which it is introduced or that the coding sequence for the enzyme comes from the same species as the cell in which it is introduced but it is considered heterologous due to its environment which is not natural, for example because it is under the control of a promoter which is not its natural promoter, or is introduced at a location which differs from its natural location.

Nucleic acid construct: The term "nucleic acid construct" means a nucleic acid molecule, either single- or double-stranded, which is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to a coding sequence, in such a way that the control sequence directs expression of the coding sequence.

Overexpress: The term overexpress means to express or cause to be expressed a nucleic acid or polypeptide in a cell at a greater concentration than is normally expressed in a corresponding wild-type cell.

Sequence identity: The sequence identity between two amino acid sequences is described by the parameter "sequence identity". For purposes of the present invention, the "percentage identity" between two amino acid sequences (A) and (B) is determined by comparing the two sequences aligned in an optimal manner, through a window of comparison. Said alignment of sequences can be carried out by well-known methods, for example, using the algorithm for global alignment of Needleman-Wunsch. Protein analysis software matches similar sequences using measures of similarity assigned to various substitutions, deletions and other modifications, including conservative amino acid substitutions. Once the total alignment is obtained, the percentage of identity can be obtained by dividing the full number of identical amino acid residues aligned by the full number of residues contained in the longest sequence between the sequence (A) and (B).

Sequence identity is typically determined using sequence analysis software. For comparing two amino acid sequences, one can use, for example, the tool "Emboss needle" for pairwise sequence alignment of proteins providing by EMBL-EBI and available on: Worldwide Web site: ebi.ac.uk/Tools/services/web/toolform.ebi?tool=emboss_needle&context=protein, using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

Alternatively, Sequence identity can also be typically determined using sequence analysis software Clustal Omega using the HHalign algorithm and its default settings as its core alignment engine. The algorithm is described in Söding, J. (2005) 'Protein homology detection by HMM-HMM comparison'. Bioinformatics 21, 951-960, with the default ettings (see Worldwide Web site: ebi.ac.uk/Tools/msa/clustalo/).

Amino acids: The amino acid sequences defined herein are represented by a one-letter symbol as shown below: A, Ala, (alanine); R, Arg, (arginine); N, Asn, (asparagine); D, Asp, (aspartic acid); C, Cys, (cysteine); Q, Gln, (glutamine); E, Glu, (glutamic acid); G, Gly, (glycine); H, His, (histidine); I, Ile, (isoleucine); L, Leu, (leucine); K, Lys, (lysine); M, Met, (methionine); F, Phe, (phenylalanine); P, Pro, (proline); S, Ser, (serine); T, Thr, (threonine); W, Trp, (tryptophan); Y, Tyr, (tyrosine); and V, Val, (valine).

By "consist essentially" is intended that the polypeptide has the indicated SEQ ID No and can further comprise an alteration, i.e., a substitution, insertion, and/or deletion, of no more than 20 amino acids, preferably no more than 10 amino acids. In particular, the polypeptide may have alterations at no more than 11, 10, 9, 8, 7, 6, 5, 4, 3, 2 or 1 amino acids, e.g., may have substitution, insertion, and/or deletion of 1, 2, 3, 4, 5, 6, 7, 8, 9 or 10 amino acids. A substitution means replacement of the amino acid occupying a position with a different amino acid; a deletion means removal of the amino acid occupying a position; and an insertion means adding an amino acid adjacent to and immediately following the amino acid occupying a position. The substitution can be a conservative substitution. Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill (1979, In, The Proteins, Academic Press, New York). Common substitutions are the followings Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuA al, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like. Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for the capacity to produce 4-HBA from L-tyrosine to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for instance, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127). Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Conserved: By conserved amino acid is intended that a defined sequence is aligned with the reference sequence and the residue of the defined sequence corresponding the position indicated in the reference sequence is identical to the residue present in the reference sequence. The alignment can be performed by any available method, and in particular by the method disclosed for identity determination just above, more preferably by Clustal Omega. The residue position is indicated in the reference sequence.

Purify or Purified: As used herein, the term "purify," "purified," or "purification" means the removal or isolation of a molecule from its environment by, for example, isolation or separation. "Substantially purified" molecules are at least about 60% free, preferably at least about 75% free, and more preferably at least about 90% free from other components with which they are associated. As used herein, these terms also refer to the removal of contaminants from a sample. For example, the removal of contaminants can result in an increase in the percentage of alkanes/alkenes in a sample. For example, when alkanes/alkenes are produced in a host cell, the alkanes/alkenes can be purified by the removal of host cell proteins. After purification, the percentage of alkanes/alkenes in the sample is increased. The terms "purify," "purified," and "purification" do not require absolute purity. They are relative terms. Thus, for example, when olefins are produced in host cells, a purified alkane/alkene is one that is substantially separated from other cellular components (e.g., nucleic acids, polypeptides, lipids, carbohydrates, or other hydrocarbons). In another example, a purified alkanes/alkenes preparation is one in which the alkanes/alkenes is substantially free from contaminants, such as those that might be present following fermentation. In some embodiments, alkanes/alkenes is purified when at least about 50% by weight of a sample is composed of the alkanes/alkenes. In other embodiments, an olefin is purified when at least about 60%, 70%, 80%, 85%, 90%, 92%, 95%, 98%, or 99% or more by weight of a sample is composed of the alkanes/alkenes.

Fatty Acid Decarboxylase Activity:

By "fatty acid decarboxylase activity" is referred to the removal of the carboxylic acid group from fatty acid, in particular the direct removal without an aldehyde intermediate and without introducing a terminal unsaturation. The fatty acid decarboxylase activity can be measured by any method available to the skilled person. More preferably, the activity can be measured by the following method.

In vitro enzymatic assays, reactions are performed in sealed vials containing 100 nmoles of substrate (typically C16:0 free fatty acid) dissolved in the appropriate solvent (ethanol or dimethyl sulfoxide), 2 nmoles of C16 alkane as internal standard, and 5 to 10 µg of purified enzyme (containing its FAD cofactor) with 500 µL of the activity buffer (50 mM Tris-HCl pH 8.2 with 100 mM NaCl), or a total protein extract. Vials are incubated at 25° C. in the presence of white light (or any light containing blue photons) at 2000 µmole.photon.m$^{-2}$·s$^{-1}$ on a rotating agitator at 250 rpm. Concentrated sodium hydroxide (10 µL at 10 M) is then injected into the vial to stop the reaction and the samples are cooled down on ice. Hydrocarbons are extracted with hexane and quantified by gas chromatography coupled to flame ionization detector and mass spectrometry (GC-FID-MS).

Fatty Acid Decarboxylase Polypeptide:

The present invention relates to a polypeptide having a fatty acid decarboxylase activity, called herein "fatty acid decarboxylase", and comprising, essentially consisting in or consisting in a sequence having at least 40% of identity with SEQ ID No 1, SEQ ID No 5 or SEQ ID No 7, preferably SEQ ID No 1.

For instance, the fatty acid decarboxylase comprises, essentially consists in or consists in a sequence having at least 42%, 45%, 50% or 55% of identity with SEQ ID No 1, SEQ ID No 5 or SEQ ID No 7, preferably SEQ ID No 1.

In another aspect, the fatty acid decarboxylase comprises, essentially consists in or consists in a sequence at least 55, 55, 60, 65, 70, 75, 80, 85, 90, 95 or 99% of identity with any of the SEQ ID Nos 1-3 and 5-14.

In a further aspect, the fatty acid decarboxylase comprises, essentially consists in or consists in the sequence of any of the SEQ ID Nos 1-3 and 5-14. In a preferred embodiment, the fatty acid decarboxylase comprises, essentially consists in or consists in the sequence of any of the SEQ ID Nos 1, 5, 7-14, more preferably any of the SEQ ID Nos 1, 5, and 7.

In an embodiment, the fatty acid decarboxylase comprises the consensus sequence G-$X_1$-L-$(X)_4$-C-[D/E]-$X_2$-G-[A/G]-F-$X_3$-[K/R/S/E] (SEQ ID No 4), X being any amino acid (SEQ ID No 26). In a preferred embodiment, the fatty acid decarboxylase comprises the consensus sequence G-$X_1$-L-$(X)_4$-C-[D/E]-$X_2$-G-[A/G]-F-$X_3$-[K/R] (SEQ ID No 4), X being any amino acid.

Preferably, $X_1$ can be selected from the group consisting of P, L and G. Preferably, $(X)_4$ can be more specifically [T/A]-[T/S/C]-[P/T/A]-[G/A]. Preferably, $X_2$ can be selected from the group consisting of H, N and R. Preferably, $X_3$ can be a hydrophobic amino acid, especially selected from the group consisting of L, V A and F.

In a specific embodiment, the fatty acid decarboxylase comprises the consensus sequence G-$X_1$-L-$(X)_4$-C-[D/E]-$X_2$-G-[A/G]-F-$X_3$-[K/R/S/E] (SEQ ID No 26), wherein $X_1$ can be selected from the group consisting of P, L and G;

$(X)_4$ can be more specifically [T/A]-[T/S/C]-[P/T/A]-[G/A];

$X_2$ can be selected from the group consisting of H, N and R; and $X_3$ can be a hydrophobic amino acid, especially selected from the group consisting of L, V A and F.

In a very specific embodiment, the fatty acid decarboxylase comprises the consensus sequence G-$X_1$-L-$(X)_4$-C-[D/E]-$X_2$-G-[A/G]-F-$X_3$-[K/R] (SEQ ID No 4), wherein $X_1$ can be selected from the group consisting of P, L and G;

$(X)_4$ can be more specifically [T/A]-[T/S/C]-[P/T/A]-[G/A];

$X_2$ can be selected from the group consisting of H, N and R; and $X_3$ can be a hydrophobic amino acid, especially selected from the group consisting of L, V A and F.

In another or additional preferred embodiment, the fatty acid decarboxylase comprises conserved amino acids with reference to SEQ ID No 1. Based on the reference sequence of SEQ ID No 1, one, two, three, four, five or all of the residues C372, R391, Y406, Q426, H512 and N515 of SEQ ID No 1 are conserved. The same can be true for the corresponding residue at the positions in another fatty acid decarboxylase corresponding to these positions in SEQ ID No 1.

In another or additional preferred embodiment, the fatty acid decarboxylase comprises a region forming a hydrophobic tunnel in which the substrate, the free fatty acid, could enter. This region is located between residues from positions 391 to 426 in SEQ ID No 1. Accordingly, at least 40% of the amino acid residues between positions 388-428 are hydrophobic residues, preferably selected from the groups consisting of V, I, L, M, F, W, C A and Y.

The fatty acid decarboxylase is any origin such as from bacteria or algae.

Preferably, the fatty acid decarboxylase is from algae, preferably microalgae or cyanobacteria. For instance, the fatty acid decarboxylase is a GMC oxidoreductase having a fatty acid decarboxylase activity from *Chlorella, Chlamydomonas, Phaeodactylum, Coccomyxa, Volvox, Ectocarpus, Emiliania, Aureococcus, Chondrus, Galdieria* or *Nannochloropsis*. A lot of species of microalgae are known and can be found for instance on the database AlgaeBase (see Worldwide Web site: algaebase.org/).

In a particular embodiment, the fatty acid decarboxylase is from *Chlorella variabilis*, in particular *Chlorella variabilis* NC64A. In another particular embodiment, the fatty acid decarboxylase is from *Chlamydomonas reinhardtii*. In another particular embodiment, the fatty acid decarboxylase is from *Phaeodactylum tricornutum*. In another particular embodiment, the fatty acid decarboxylase is from *Coccomyxa subellipsoidea*, in particular *Coccomyxa subellipsoidea* C-169. In another particular embodiment, the fatty acid decarboxylase is from *Volvox carteri*. In another particular embodiment, the fatty acid decarboxylase is from *Ectocarpus siliculosus*. In another particular embodiment, the fatty acid decarboxylase is from *Emiliania huxleyi*. In another particular embodiment, the fatty acid decarboxylase is from

*Aureococcus anophagefferens*. In another particular embodiment, the fatty acid decarboxylase is from *Nannochloropsis gaditana*.

Preferably, the fatty acid decarboxylase has no more than about 750, 700, 650, or 600 amino acid residues in length.

The present invention also relates to a hybrid polypeptide or fusion polypeptide in which the amino acid sequence of the fatty acid decarboxylase as defined above is fused at the N-terminus or the C-terminus of a region of another polypeptide. The fatty acid decarboxylase activity remains in the hybrid polypeptide or fusion polypeptide. Preferably, the region of another polypeptide is fused at the N-terminus of the fatty acid decarboxylase. Alternatively, the region of another polypeptide is fused at the C-terminus of the fatty acid decarboxylase. Techniques for producing fusion polypeptides are known in the art, and include ligating the coding sequences encoding the enzyme and the addition region of another polypeptide so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

The addition region of the fusion polypeptide can be selected in order to enhance the stability of the enzyme according to the present disclosure, to promote the secretion (such as a N-terminal hydrophobic signal peptide) of the fusion protein from a cell (such as a bacterial cell or a yeast cell), or to assist in the purification of the fusion protein. More particularly, the additional region can be a tag useful for purification or immobilization of the enzyme. Such a tag is well-known by the person skilled in the art, for instance a His tag (His$_6$), a FLAG tag, a HA tag (epitope derived from the Influenza protein haemagglutinin), a maltose-binding protein (MPB), a MYC tag (epitope derived from the human proto-oncoprotein MYC), a STREP tag or a GST tag (small glutathione-S-transferase). The additional region can be the thioredoxin.

A fusion polypeptide can further comprise a cleavage site between the enzyme and the addition region. Upon secretion or purification of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48. For instance, the cleavage site can be a TEV (Tobacco Etch Virus) cleavage site. Other cleavage sites are well-known by the person skilled in the art.

In a particular embodiment, the present invention relates to a polypeptide comprising an histidine tag, a thioredoxin, a cleavage site and the fatty acid decarboxylase as defined above (e.g. see SEQ ID No 3 for such a construction with *Chlorella* fatty acid decarboxylase).

The present invention further relates to a recombinant nucleic acid construct or vector comprising a nucleic acid sequence encoding the fatty acid decarboxylase as defined above. More particularly, the nucleic acid construct or vector is suitable for expressing said fatty acid decarboxylase. In addition, it is provided a recombinant host cell comprising a nucleic acid, a recombinant nucleic acid construct or a recombinant vector comprising a nucleic acid sequence encoding the fatty acid decarboxylase as defined above.

Nucleic Acids Encoding Fatty Acid Decarboxylase and Nucleic Acid Constructs

The present invention relates to a polynucleotide encoding a fatty acid decarboxylase of the present invention. The nucleic acid can be DNA (cDNA or gDNA), RNA, or a mixture of the two. It can be in single stranded form or in duplex form or a mixture of the two. It can comprise modified nucleotides, comprising for example a modified bond, a modified purine or pyrimidine base, or a modified sugar. It can be prepared by any method known to one skilled in the art, including chemical synthesis, recombination, and mutagenesis.

Optionally, the encoding sequence can be optimized for the host cell expression. In particular, as the fatty acid decarboxylases of the present invention are from algae, in particular microalgae, the nucleic acid sequence encoding the enzyme can be optimized for a bacterial host, such as *E. coli*, a yeast host or even a microalga which is different from the one from which the enzyme originates.

The present invention also relates to nucleic acid constructs comprising a polynucleotide encoding a fatty acid decarboxylase according to the present disclosure operably linked to one or more control sequences that direct the expression of the coding sequence in a suitable host cell under conditions compatible with the control sequences. A polynucleotide may be manipulated in a variety of ways to provide for expression of the fatty acid decarboxylase. Manipulation of the polynucleotide prior to its insertion into a vector may be desirable or necessary depending on the expression vector. The techniques for modifying polynucleotides utilizing recombinant DNA methods are well known in the art.

The control sequence may include a promoter that is recognized by a host cell or an in vitro expression system for expression of a polynucleotide encoding a fatty acid decarboxylase of the present invention. The promoter contains transcriptional control sequences that mediate the expression of the fatty acid decarboxylase. The promoter may be any polynucleotide that shows transcriptional activity in the host cell including mutant, truncated, and hybrid promoters, and may be obtained from genes encoding extracellular or intracellular polypeptides either homologous or heterologous to the host cell. Optionally, the promoter can be inducible. Optionally, the promoter is a strong promoter allowing the overexpression of the fatty acid decarboxylase. Optionally, the promoter is a strong inducible promoter.

Examples of suitable promoters in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, Molecular Microbiology 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, Proc. Natl. Acad. Sci. USA 75: 3727-3731), as well as the tac promoter (DeBoer et al., 1983, Proc. Natl. Acad. Sci. USA 80: 21-25). Further promoters are described in "Useful proteins from recombinant bacteria" in Gilbert et al., 1980, Scientific American 242: 74-94; and in Sambrook et al., 1989. Examples of tandem promoters are disclosed in WO 99/43835.

Examples of suitable promoters in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene; and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

An inducible promoter can be responsive to, e.g., light intensity or high or low temperature, and/or can be responsive to specific compounds. The inducible promoter may be, for example, a hormone-responsive promoter (e.g., an ecdysone-responsive promoter, such as described in U.S. Pat. No. 6,379,945), a metallothionien promoter (U.S. Pat. No. 6,410,828), a pathogenesis-related (PR) promoter that can be responsive to a chemical such as, for example, salicylic acid, ethylene, thiamine, and/or BTH (U.S. Pat. No. 5,689,044), or the like, or some combination thereof. An inducible promoter can also be responsive to light or dark (U.S. Pat. Nos. 8,318,482; 5,750,385; 5,639,952), metals (Eukaryotic Cell 2:995-1002 (2003)) or temperature (U.S. Pat. No. 5,447,858; Abe et al. Plant Cell Physiol. 49: 625-632 (2008); Shroda et al. Plant J. 21: 121-131 (2000). The foregoing examples are not limiting as to the types of promoters or specific promoters that may be used. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

One skilled in the art will readily appreciate that a variety of known promoter sequences can be usefully deployed for microalgal species. For example, the promoters commonly used to drive transgene expression in microalgae include various versions of the of cauliflower mosaic virus promoter 35S (CaMV35S), which has been used in both dinoflagellates and chlorophyta (Chow et al, Plant Cell Rep., 18:778-780, 1999; Jarvis and Brown, Curr. Genet., 317-321, 1991; Lohuis and Miller, Plant J., 13:427-435, 1998). The SV40 promoter from simian virus has also reported to be active in several algae (Gan et al., J. Appl. Phycol., 151 345-349, 2003; Qin et al, Hydrobiologia 398-399, 469-472, 1999). The promoters of RBCS2 (ribulose bisphosphate carboxylase, small subunit) (Fuhrmann et al, Plant J., 19:353-361, 1999) and PsaD (abundant protein of photosystem I complex; Fischer and Rochaix, FEBS Lett. 581:5555-5560, 2001) from *Chlamydomonas* can also be useful. The fusion promoters of HSP70A/RBCS2 and HSP70A/p2TUB (tubulin) (Schroda et al, Plant J., 21: 121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al, Mar. Biotechnol, 1:239-251, 1999; Zaslayskaia et al, J. Phycol. 36:379-386, 2000) or the vcp gene encoding a eustigmatophyte violaxanthin-chlorophyll a/b binding protein (see U.S. Pat. No. 8,318, 482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, FEBS Lett 272:3413-3423, 2005), thus gene expression can be switched off or on when microalgal cells are grown in the presence of ammonium/nitrate. Various algal promoters are known and can be used, including those disclosed in US 2013/0023035; US 2013-0323780, US 2014-0154806; and US 2014-0363892.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a non-translated region of an mRNA that is important for translation by the host cell. The leader is operably linked to the 5'-terminus of the polynucleotide encoding the fatty acid decarboxylase. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide encoding the fatty acid decarboxylase and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of the fatty acid decarboxylase and directs the fatty acid decarboxylase into the cell's secretory pathway. The 5'-end of the coding sequence of the polynucleotide may inherently contain a signal peptide coding sequence naturally linked in translation reading frame with the segment of the coding sequence that encodes the fatty acid decarboxylase. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used. The signal peptide can also be a chloroplast transit peptide, the chloroplast transit peptide of the fatty acid decarboxylase or any other chloroplast transit peptide.

Effective signal peptide coding sequences for bacterial host cells are the signal peptide coding sequences obtained from the genes for *Bacillus* NCIB 1 1837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a nucleic acid construct as disclosed above, or a polynucleotide encoding a fatty acid decarboxylase of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the fatty acid decarboxylase at such sites. Alternatively, the polynucleotide may be expressed by inserting the polynucleotide or a nucleic acid construct comprising the polynucleotide into an appropriate vector for expression.

In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophy, and the like.

Examples of bacterial selectable markers are *Bacillus licheniformis* or *Bacillus subtilis* genes or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* gene.

The vector preferably contains an element(s) that permits integration of the vector into the host cell's genome or autonomous replication of the vector in the cell independent of the genome.

When integration into the host cell genome occurs, integration of the sequences into the genome may rely on homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo. Examples of bacterial origins of replication are the origins of replication of plasmids pBR322, pUC19, pACYC177, and pACYC184 permitting replication in *E. coli*, and pUB1 10, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention relates to a recombinant host cell expressing a fatty acid decarboxylase of the present invention, more specifically a recombinant host cell engineered to produce alkanes/alkenes. The recombinant host cell may express an endogenous fatty acid decarboxylase but with an overexpression thereof (for instance by controlling the expression by a strong heterologous promoter and/or by increasing the gene number encoding the fatty acid decarboxylase in the cell). Alternatively, the recombinant host cell may express a heterologous fatty acid decarboxylase of the present invention. In addition or in another alternative, the recombinant host cell has been genetically engineered to increase the production of fatty acids or favoring the production of preferential fatty acids. For instance, the host cell can be a bacterium (including a photosynthetic bacterium), a filamentous fungus, a yeast or a microalga from a different species than the one from which originates the fatty acid decarboxylase.

Accordingly, the present invention relates to recombinant host cells comprising a polynucleotide encoding a fatty acid decarboxylase according to the present disclosure operably linked to one or more control sequences that direct the production of the fatty acid decarboxylase of the present invention. A construct or vector comprising a polynucleotide encoding a fatty acid decarboxylase according to the present disclosure is introduced into a host cell so that the construct or vector is maintained as a chromosomal integrant or as a self-replicating extra-chromosomal vector as described earlier.

The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a fatty acid decarboxylase of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*. The bacterial host cell may be any *Bacillus* cell including, but not limited to, *Bacillus alkalophilus, Bacillus amyloliquefaciens, Bacillus brevis, Bacillus circulans,*

*Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells. The bacterial host cell may also be any *Streptococcus* cell including, but not limited to, *Streptococcus equisimilis, Streptococcus pyogenes, Streptococcus uberis, Streptococcus equi* and *Streptococcus zooepidemicus* cells. The bacterial host cell may further be any *Streptomyces* cell including, but not limited to, *Streptomyces achromogenes, Streptomyces avermitilis, Streptomyces coelicolor, Streptomyces griseus,* and *Streptomyces lividans* cells. In a particular embodiment, the host cell is a cyanobacteria. Cyanobacteriae include, but are not limited to, species of the genera *Synechococcus, Synechocystis, Anabaena, Spirulina.*

The introduction of DNA into a *Bacillus* cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, J. Mol. Biol. 166: 557-580) or electroporation (see, e.g., Dower et al, 1988, Nucleic Acids Res. 16: 6127-6145). The introduction of DNA into a *Streptomyces* cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a *Pseudomonas* cell may be effected by electroporation (see, e.g., Choi et al., 2006, J. Microbiol. Methods 64: 391-397) or conjugation (see, e.g., Pinedo and Smets, 2005, Appl. Environ. Microbiol. 71: 51-57). The introduction of DNA into a *Streptococcus* cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804), or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell. The host cell may be a fungal cell. "Fungi" as used herein includes the phyla *Ascomycota, Basidiomycota, Chytridiomycota,* and *Zygomycota* as well as the *Oomycota* and all mitosporic fungi (as defined by Hawksworth et al., In, Ainsworth and Bisby's Dictionary of The Fungi, 8th edition, 1995, CAB International, University Press, Cambridge, UK). The fungal host cell may be a yeast cell. "Yeast" as used herein includes ascosporogenous yeast (Endomycetales), basidiosporogenous yeast, and yeast belonging to the Fungi imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980). The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell. The fungal host cell may be a filamentous fungal cell. "Filamentous fungi" include all filamentous forms of the subdivision *Eumycota* and *Oomycota* (as defined by Hawksworth et al., 1995, supra). The filamentous fungi are generally characterized by a mycelial wall composed of chitin, cellulose, glucan, chitosan, mannan, and other complex polysaccharides. The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosurn, Fusarium trichothecioides, Fusarium venenatum, Humicola insolens, Humicola lanuginosa, Mucor miehei, Myceliophthora thermophila, Neurospora crassa, Penicillium purpurogenurn, Phanerochaete chrysosporium, Phlebia radiata, Pleurotus eryngii, Thielavia terrestris, Trametes villosa, Trametes versicolor, Trichoderma harzianurn, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

The cell can also be a mammalian cell, for example COS, CHO (U.S. Pat. Nos. 4,889,803; 5,047,335). In a particular embodiment, the cell is non-human and non-embryonic. In addition, the fatty acid decarboxylase of the invention could be produce by a non-human transgenic animal, for instance in the milk produces by the animal.

Algal species suitable for the method of the invention include microalgae such as, for example, species of the genera *Achnanthes, Amphiprora, Amphora, Ankistrodesmus,*

*Asteromonas, Aurantiochytrium, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eudorina, Eremosphaera, Ernodesmius, Euglena, Eustigmatos, Franceia, Fragilaria, Fragilaropsis, Gloeothamnion, Gonium, Haematococcus, Hantzschia, Heterosigma, Hymenomonas, Isochrysis, Lepocinclis, Lobosphaera, Micr actinium, Micrasterias, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pandorina, Parachlorella, Parietochloris, Parietichytrium, Pascheria, Pavlova, Pelagomonas, Phaiodactylum, Phagus, Picochlorum, Platymonas, Pleurochrysis, Pleurococcus, Prototheca, Pseudochlorella, Pseudochoricystis, Pseudoneochloris, Pseudostaurastrum, Pyramimonas, Pyrobotrys, Scenedesmus, Schizochlamydella, Schizochytrium, Skeletonema, Spyrogyra, Stichococcus, Tetrachlorella, Tetraselmis, Thalassiosira, Thrautochytrium, Tribonema, Ulva, Vaucheria, Viridiella, Vischeria,* and *Volvox.* Non-limiting examples of particularly suitable species include, for instance, diatoms such as, for example, a species of any of the genera *Amphora, Chaetoceros, Cyclotella, Cylindrotheca, Fistulifera, Fragilaria, Fragilaropsis, Navicula, Nitzschia, Phaeodactylum,* Pseudo-nitzia, or *Thalassiosira,* or eustigmatophytes, e.g., *Eustigmatos, Monodus, Nannochloropsis,* or *Vischeria.*

More specifically, microalgae that may be used include, but are not limited to, *Achnanthes orientalis, Agmenellum, Amphiprora hyaline, Amphora cojfeiformis, Amphora cojfeiformis linea, A mphora coffeijbrmis punctata, Amphora cojfeiformis taylori. Amphora cojfeiformis tenuis, Amphora delicatissima. Amphora delicatissima capitaia, Amphora* sp., *Anahaena, Anabaena variabilis, Ankistrodesrnus, Ankistrodesrnus jalcatus, Boekelovia hooglandii, Borodinella* sp., *Botryococciis braunii, Botryococcus sudeiicus, Bracteococcus minor, Bracteococcus medionucleatus, Carteria, Chaetoceros gracilis, Chaetoceros muelleri, Chaetoceros muelleri suhsalsum, Chaetoceros* sp., *Chlamydomonas reinhardtii, Chlamydomonase moewusi, Chlamydomonas nivalis, Chlamydomonas caudate. Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella in fusionurn* var. *auxenophila, Chlorella kessleri, Chlorella lobophora* (strain SAG 37.88), *Chlorella luteoviriais, Chlorella luteoviridis* var. *aureoviridis. Chlorella luteoviridis* var. *lutescens, Chlorella miniata, Chlorella minutissima, Chlorella mutabilis, Chlorella nocturna, Chlorella ova lis, Chlorella parva, Chlorella photophila, Chlorella pringsheimii, Chlorella protothecoides* var. *acidicola, Chlorella regularis, Chlorella regularis* var. *minima, Chlorella regularis* var. *umhricata, Chloreila reisiglii, Chlorella saccharophila, Chlorella saccharophila* var. *ellipsoidea. Chlorella salina, Chlorella simplex. Chlorella sorokiniana, Chlorella* sp., *Chlorella sphaerica. Chlorella stigmaiophora, Chlorella variabilis, Chlorella vanniellii, Chlorella vulgaris, Chlorella vulgaris* f. *tenia, Chlorella vulgaris* var. *autotrophica, Chlorella vulgaris* var. *viridis, Chlorella vulgaris* var. *vulgaris, Chlorella vulgaris* var. *vulgaris* f. *tertia, Chlorella vulgaris* var. *vulgaris* f. *viridis, Chlorella xanthella, Chlorella zojingiensis, Chlorella trehouxioides, Chlorella vulgaris, Chlorococcum infusionum, Chlorococcum* sp., *Chlorogonium, Chroomonas* sp., *Chrysosphaera* sp., *Coccomyxa suhellipsoidea* C-169, *Cricosphaera* sp., *Crypihecodinium cohnii. Cryptomonas* sp., *Cyclotella cryptica, Cyclotella meneghiniana, Cyclotella* sp., *Dunaiiella* sp., *Dimaliella bardawil, Dunaiiella hioculata, Dunaiiella granulate, Dunaiiella maritime, Dunaiiella minuta, Dunaiiella parva, Dunaiiella peircei, Dunaliella primolecta, Dunaliella saiina, Dimaliella terricola, Dunaliella tertiolecta, Dimaliella viridis, Dunaliella tertiolecta, Eremosphaera viridis, Eremosphaera* sp., *Ellipsoidon* sp. *Euglena. Franceia* sp., *Fragilaria crotonensis, Fragilaria* sp., *Gleocapsa* sp., *Gloeothamnion* sp., *Haematococcus plwialis, Hymenomonas* sp., *Isochrysis affgalhana, Isochrysis galbana, Lepocinclis, Micr actinium, Micr actinium, Micromonas, Micromonas pusilla, Monoraphidium minuium, Monoraphiaium* sp., *Nannochloris* sp., *Nannochloropsis saiina, Nannochloropsis* sp., *Navicula acceptata, Navicula hiskanterae, Navicula pseudotenelloides, Navicula pelliculosa, Navicula saprophila, Navicula* sp., *Nephrochloris* sp., *Nephroselrnis* sp., *Nitschia communis, Nitzschia alexandfjna, Nitzschia communis, Nitzschia dissipata, Nitzschia frustulum, Nitzschia hantzschiana. Nitzschia inconspicua, Nitzschia intermedia, Nitzschia microcephalia, Nitzschia pusilla, Nitzschia pusilla elliptica, Nitzschia pusilla monoensis, Nitzschia quadrangular, Nitzschia* sp., *Nostoc* sp., *Nostoc Pimctiforme, Ochromonas* sp., *Oocystis parva, Oocystis pusilla, Oocystis* sp., *Osc Ilatoria limnetica, Oscillatoria* sp., *Oscillatoria suborevis, Osterococcus, Osterococcus lucimariniis, Osterococcus tauri, Parachlorella kessleri, Pascheria acidophila, Pavlova* sp., *Phagus, Phaaodactylum tricornuturn, Pnormidium, Piaiymonas* sp., *Pleurochrysis carter ae, Pleurochrysis dentate, Pleurochrysis* sp., *Prochlorococcus marinus, Prototheca wickerhamii, Prototheca stagnant, Prototheca portoricensis, Prototheca moirforrms, Prototheca zopfii, Pseudochlorella aquatica, Pyramirnorias* sp., *Pyroboirys, Rhodococcus opacus. Sarcinoid chrysophyte, Scenedesmus armatus, Scynechocystis* sp., *Scynechococcus, Schizochytrim, Spirogyra, Spirulina platen sis, Stichococcus* sp., *Synechococcus* sp., *Tetraedron, Thalassiosira pseudonana, Tetraselmis* sp., *Tetraselmis suecica, Thalassiosira weissflogii, Viridiella fridericiana,* and *Volvox carteri.* In some embodiments, members of the genus *Nannochloropsis* are selected amoung *N. gaditana, N. granulata, N. limnetica, N. oceanica, N. oculata,* and *N. salina.*

Algal species suitable for the method of the invention also include, but are not limited to, algae species of the genera *Rhodophyta* such as *Cyanidioschyzon, Gracilaria, Kappaphycus, Porphyridium,* and *Porphyra;* Charophyta such as *Closterium* and *Penium;* Chlorophyta such as *Eudorina, Gonium, Haematococcus, Lobosphaera, Micrasterias, Ostreococcus, Pandorina, Parachlorella, Platymonas, Pseudochoricystis, Scenedesmus, Ulva,* and *Volvox;* Phaeophyta such as *Laminaria.*

The host cell can also be selected among species of the genera *Dinophyta* such as *Amphidinium* and *Symbiodinium;* Chlorarachniophyta such as *Lotharella;* Euglenozoa such as *Euglena.*

According to the present invention, alkanes/alkenes having particular branching patterns, levels of saturation, and carbon chain length can be produced from fatty acid substrates having those particular characteristics with the fatty acid decarboxylase of the invention. Accordingly, each step within a fatty acid biosynthetic pathway can be modified to produce or overproduce a fatty acid substrate of interest. For example, known genes involved in the fatty acid biosynthetic pathway can be expressed, overexpressed, or attenuated in host cells to produce a desired fatty acid substrate (see, for instance WO08/119082, U.S. Pat. No. 8,183,028). Exemplary genes are provided in FIG. 1 of WO08/119082 or in Table 1 and col 25-30 of U.S. Pat. No. 8,183,028 (the disclosure being incorporated herein by reference).

Then, the host cell can be modified for increasing or directing the lipid production and/or fatty acid production. The modified host cell can be selected for its capacity to produce free fatty acids or a particular profile of free fatty acids, for instance after random mutagenesis, or can be prepared by genetic engineering by introducing new genes or increasing the expression of some genes (genes involved in the free fatty acids anabolism) and/or by deleting other genes or reducing their expression (genes involved in the free fatty acids catabolism). In addition, the host cell can be modified in order to increase the production of preferential fatty acids and decrease the production of unwanted fatty acids.

For example, for production of lipid, a host cell (such as but not limited to an algal or heterokont host cell) can optionally include one or more non-native genes encoding polypeptides that functions in lipid biosynthesis, including, but not limited to, polypeptides that encode enzymes for the production of fatty acids, fatty acid derivatives, and/or glycerolipids including, but not limited to, diacylglycerol acyltransferase (DGAT) gene, a glycerolphosphate acyltransferase (GPAT) gene, a lysophosphatidic acid acyltransferase (dehydrogenase) (LPAAT) gene, a phosphatidic acid phosphatase (PAP) gene, and/or a monoacylglycerol acyltransferase (MGAT) gene.

In a preferred embodiment, the host cell has been modified for expressing or overexpressing a lipase. A lipase hydrolyses an acyl-lipid (such as a triglyceride or a glycerophospholipid or a glycerogalactolipid) for producing free fatty acids and glycerol. Preferably, the lipase will be a lipolytic enzyme with a broad triacylglycerol, phospholipase and galactolipase activity. Examples include the guinea pig pancreatic lipase-related protein type 2, the *Fusarium* cutinase or the *Staphylococcus hyicus* lipase (Liu et al. 2011, PNAS 108:6905). In a preferred embodiment, the host cell is bacterial and expresses, preferably overexpresses, a lipase. Accordingly, one object of the present invention is a recombinant host cell expressing, preferably overexpressing, a fatty acid decarboxylase of the present invention and a lipase, one of them or both being heterologous to the host cell. In a preferred embodiment, the host cell is bacterial.

In a preferred embodiment, the host cell has been engineered to express, overexpress or attenuate expression of a thioesterase to increase fatty acid production or favor the production of preferential fatty acids. Preferably, the host cell has been modified for expressing or overexpressing a thioesterase. Accordingly, one object of the present invention is a recombinant host cell expressing, preferably overexpressing, a fatty acid decarboxylase of the present invention and a thioesterase, one of them or both being heterologous to the host cell. In a preferred embodiment, the host cell is a microalga or a cyanobacterium.

By terminating fatty acid biosynthesis, the acyl-acyl carrier protein (ACP) thioesterase functionally determines the length and identity of the fatty acid end product (Salas et al., (2002) Archives of Biochemistry and Biophysics 403: 25-34). Based on amino acid sequence alignments, the plant thioesterases have been shown to cluster into two families, FatAs, which show marked preference for 18:1-ACP with minor activity towards 18:0- and 16:0-ACPs; and FatBs, which hydrolyze primarily saturated acyl-ACPs with chain lengths that vary between 8-16 carbons (Voelker, In Genetic Engineering Volume 18. Edited by: Setlow J K. New York, Plenum Press; 1996: 111-133; Ginalski, et al., Nucl Acids Res (2003) 31:3291-3292; and Jones, et al, (1995) Plant Cell 7: 359-371).

The thioesterase belongs to the enzyme from EC 3.1.2, more particularly from EC 3.1.2.2 (Palmitoyl-CoA hydrolase), EC 3.1.2.14 (Oleoyl-[acyl-carrier-protein] hydrolase), EC 3.1.2.18 (ADP-dependent short-chain-acyl-CoA hydrolase), EC 3.1.2.19 (ADP-dependent medium-chain-acyl-CoA hydrolase), EC 3.1.2.20, EC 3.1.2.21 (Dodecanoyl-[acyl-carrier-protein] hydrolase), EC 3.1.2.22 (Palmitoyl-protein hydrolase).

Examples of thioesterase have been disclosed in WO14120829, and WO16044779. They also include an *Escherichia coli* thioesterase encoded by tesB (see GenBank Accession No. AAA24665.1), a *Lactobacillus brevis* thioesterase (GenBank Accession No. ABJ63754.1), and a *Lactobacillus plantarum* esterase (GenBank Accession No. CCC78182.1). Another example of thioesterase from plant suitable for preparing medium chain fatty acid is disclosed in Radakovits et al, 2011, Metabolic Engineering 13(1):89-95.

In a preferred embodiment, the thioesterase is chosen for favoring short and medium chain fatty acids.

In a particular aspect of the present invention, it is also provided a method for producing a fatty acid decarboxylase according to the present invention, comprising culturing the host cell as defined above, under conditions conducive to the production of the fatty acid decarboxylase, and recovering and/or purifying the fatty acid decarboxylase. Alternatively, it is also provided a method for producing a fatty acid decarboxylase according to the present invention, comprising the in vitro expression of the fatty acid decarboxylase with a nucleic acid encoding the fatty acid decarboxylase as defined above. Optionally, the method further comprises a step of immobilizing the fatty acid decarboxylase on a solid support.

The enzyme may be recovered using methods known in the art. For example, the enzyme may be recovered from the nutrient medium by conventional procedures including, but not limited to, collection, centrifugation, filtration, extraction, spray-drying, evaporation, or precipitation.

The enzyme may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides. In an alternative aspect, the enzyme is not recovered, but rather a host cell of the present invention expressing the enzyme is used as a source of the enzyme.

Use for Producing Alkanes/Alkenes

The present invention also relates to the use of a fatty acid decarboxylase as defined above, or solid support comprising the fatty acid decarboxylase, or a recombinant host cell comprising a nucleic acid, a recombinant nucleic acid construct or a recombinant vector comprising a nucleic acid sequence encoding the fatty acid decarboxylase as defined above, for producing alkanes/alkenes from fatty acids.

Fatty Acid Substrates:

The alkanes/alkenes are produced by the enzyme according to the present invention from fatty acids. Especially, the fatty acids are free fatty acids comprising an aliphatic chain or a branched chain and a carboxyl acid group. They can be saturated or unsaturated. They can be monounsaturated or polyunsaturated. They may comprise from 2 to 36 carbon atoms. Generally, the fatty acids are classified into four groups based on the length of the aliphatic chain: (1) Short-chain fatty acids (SCFA) are fatty acids with aliphatic tails of fewer than six carbons (e.g. butyric acid): (2) Medium-chain fatty acids (MCFA) are fatty acids with aliphatic tails of 6-12 carbons, which can be found in medium-chain triglycerides; (3) Long-chain fatty acids (LCFA) are fatty acids with aliphatic tails 13 to 21; (4) Very long chain fatty acids (VLCFA) are fatty acids with aliphatic tails longer than 22 carbons. The present invention is highly relevant for the MCFA and LCFA, more specifically for the LCFA. In a preferred embodiment, the fatty acids comprise from 8 or 10 to 24 carbon atoms preferably from 12 to 22 carbon atoms. In some embodiments, the fatty acid substrate is a $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$ or $C_{22}$ fatty acid, preferably a $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$ or $C_{22}$ fatty acid, still more preferably a $C_{12}$, $C_{13}$, $C_{14}$, $C_{15}$, $C_{16}$, $C_{17}$, $C_{18}$, $C_{19}$, $C_{20}$, $C_{21}$ or $C_{22}$ fatty acid. More preferably, the fatty acid comprises from 8 to 20 carbon atoms preferably from 12 to 18 carbon atoms, still more preferably from 14 to 18 carbon atoms, and even more preferably from 16 or 17 carbon atoms. In a specific aspect, the fatty acid substrate is a $C_{12}$, $C_{13}$, $C_{14}$, $C_{15}$, $C_{16}$, $C_{17}$, $C_{18}$, $C_{19}$, $C_{20}$, or $C_{21}$ fatty acid, preferably a $C_{12}$, $C_{13}$, $C_{14}$, $C_{15}$, $C_{16}$, $C_{17}$, $C_{18}$, or $C_{19}$ fatty acid, still more preferably a $C_{12}$, $C_{14}$, $C_{16}$, $C_{17}$, or $C_{18}$, fatty acid. The aliphatic chain can be straight, branched or even include a cyclic moiety.

In a particular embodiment, the fatty acid comprise a branched chain. The branched chain may include a main chain with substitutions by $C_1$-$C_3$ alkyl group, preferably by methyl. In particular, the fatty acid may be a terpenoid fatty acids such as phytanic acid and pristanic acid.

In addition, the aliphatic chain of the fatty acid may be substituted by one or several groups such as an hydroxyl, a $C_1$-$C_3$ alcohol, a $C_1$-$C_3$ acyl, a $C_1$-$C_3$ ester, a $C_1$-$C_3$ amine, an amino group, a $C_1$-$C_3$ amide, a carboxyl, an aldehyde, an epoxy, an halogen, a $C_1$-$C_3$ alkoxy, a $C_1$-$C_3$ thioalkyl, a $C_1$-$C_3$ imine, a nitrile, a sulfur group such as $C_1$-$C_3$ sulfone or $C_1$-$C_3$ sulfoxide, a thiol, a nitro, a cyano, a $C_1$-$C_3$ halogenoalkyl, or may be interrupted by an heteroatom such as O, N or S, an acetylenic group, an ether such as a divinyl ether group, or an oxo group. Preferably, the aliphatic chain of the fatty acid may be substituted by one or several groups such as an hydroxyl, a carboxyl, an epoxy, an halogen, a thiol, or a nitrile, or may be interrupted by a S atom, an acetylenic group, or an ether such as a divinyl ether group. Preferably, the aliphatic chain is substituted by one group, in particular at the end of the aliphatic chain. In a very specific embodiment, the aliphatic chain of the fatty acid is substituted by an hydroxyl, especially at the end of the aliphatic chain.

In another embodiment, the aliphatic chain of the fatty acid is unsubstituted.

The fatty acid substrates can be an isolated or purified fatty acid or a mixture of fatty acids as mentioned above.

By "free fatty acid" is intended to refer to a form in which the fatty acid is in its form bearing a carboxyl group, i.e., not in an esterified form or other derivatives of fatty acids.

Alkanes/Alkenes:

The alkanes/alkenes of the present invention are obtained by decarboxylation of the corresponding fatty acids. Accordingly, the alkanes are obtained from saturated fatty acids and the alkenes from unsaturated fatty acid. The enzyme of the present invention does not introduce a terminal unsaturation. Therefore, in a preferred embodiment, the obtained alkenes do not present a terminal unsaturation.

The alkanes/alkenes obtained by the uses and methods of the present invention comprise from 8 or 10 to 24 carbon atoms preferably from 12 to 22 carbon atoms. In some embodiments, the alkane/alkene is a $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$ or $C_{22}$ alkane/alkene, preferably a $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$ or $C_{22}$ alkane/alkene, still more preferably a $C_{12}$, $C_{13}$, $C_{14}$, $C_{15}$, $C_{16}$, $C_{17}$, $C_{18}$, $C_{19}$, $C_{20}$, $C_{21}$ or $C_{22}$ alkane/alkene. More preferably, the alkane/alkene comprises from 8 to 20 carbon atoms preferably from 12 to 18 carbon atoms, still more preferably from 14 to 18 carbon atoms, and even more preferably from 16 to 17 carbon atoms. In a specific aspect, the alkane/alkene is a $C_{12}$, $C_{13}$, $C_{14}$, $C_{15}$, $C_{16}$, $C_{17}$, $C_{18}$, $C_{19}$, $C_{20}$, or $C_{21}$ alkane/alkene, preferably a $C_{12}$, $C_{13}$, $C_{14}$, $C_{15}$, $C_{16}$, $C_{17}$, $C_{18}$, or $C_{19}$ alkane/alkene, still more preferably a $C_{12}$, $C_{14}$, $C_{16}$, $C_{17}$, or $C_{18}$, alkane/alkene. The aliphatic/hydrocarbon chain can be straight, branched or even include a cyclic moiety.

In a particular embodiment, the alkane/alkene comprises a branched chain. The branched chain may include a main chain with substitutions by $C_1$-$C_3$ alkyl group, preferably by methyl. In particular, the fatty acids may be terpenoid alkanes such as phytane and pristane.

In addition, as the aliphatic chain of the fatty acids may be substituted or interrupted by one or several groups as detailed above, the corresponding alkane/alkenes after decarboxylation also comprise be substituted or interrupted by one or several groups.

Accordingly, the alkane/alkenes can be substituted by one or several groups such as an hydroxyl, a $C_1$-$C_3$ alcohol, a $C_1$-$C_3$ acyl, a $C_1$-$C_3$ ester, a $C_1$-$C_3$ amine, an amino group, a $C_1$-$C_3$ amide, a carboxyl, an aldehyde, an epoxy, an halogen, a $C_1$-$C_3$ alkoxy, a $C_1$-$C_3$ thioalkyl, a $C_1$-$C_3$ imine, a nitrile, a sulfur group such as $C_1$-$C_3$ sulfone or $C_1$-$C_3$ sulfoxide, a thiol, a nitro, a cyano, a $C_1$-$C_3$ halogenoalkyl, or may be interrupted by an heteroatom such as O, N or S, an acetylenic group, an ether such as a divinyl ether group, or an oxo group. Preferably, the alkane/alkenes may be substituted by one or several groups such as an hydroxyl, a carboxyl, an epoxy, an halogen, a thiol, or a nitrile, or may be interrupted by a S atom, an acetylenic group, or an ether such as a divinyl ether group. Preferably, the alkane/alkene is substituted by one group, in particular at the end of the aliphatic chain. In a very specific embodiment, the alkane/alkene is substituted by an hydroxyl, especially at the end of the aliphatic chain and is an alcohol.

The alkanes/alkenes can be an isolated or purified alkane/alkene or a mixture of alkanes/alkenes as mentioned above. In a very specific embodiment, the enzyme can produce C13-C17 alkanes and alkenes, especially when expressed in bacteria such as *E coli*.

Production of Alkanes/Alkenes in a Cell Free System

In a first aspect, the present invention relates to the use of a fatty acid decarboxylase as defined above for producing alkanes/alkenes from fatty acids, especially free fatty acid. Accordingly the present invention relates to a method for producing alkanes/alkenes wherein the fatty acid decarboxylase as defined above is contacted with a fatty acid or a mixture of fatty acids and is exposed to light, thereby converting the fatty acid or the mixture of fatty acids into the corresponding alkanes/alkenes. The fatty acid or mixture of fatty acids can be in a purified form or can be present in a raw composition/product. The fatty acid decarboxylase can be purified, isolated or present in a protein extract, in particular a total protein extract. Generally, FAD cofactor is already present with the fatty acid decarboxylase as a complex. Optionally, the FAD co-factor can be added with the fatty acid decarboxylase.

The enzyme needs exposure to a blue photon-containing light for its activity. In a preferred embodiment, the blue light has a wavelength from 400 to 520 nm, preferably from 450 nm to 495 nm, especially about 450 nm. The amount of light provided can be for instance from 10 to 3000 µmole.photon.m$^{-2}$·s$^{-1}$, preferably about 2000 µmole.photon.m$^{-2}$·s$^{-1}$.

However, the light may have a broader wavelength range between 300 to 540 nm. Indeed, the inventors observed that the FAD, cofactor of the enzyme, is capable of absorbing light in the range of wavelengths from 300 to 540 nm and the enzyme should be able to decarboxylate fatty acids in this range. Indeed, the FAD absorption spectrum is comprised between the wavelength range of 300 to 540 nm.

The enzyme also needs FAD (flavine adenine dinucleotide) as cofactor, which is usually bound to the enzyme purified from microalgal extracts or from the heterologous expression.

The method may comprise an additional step of recovering the alkanes/alkenes. The alkanes/alkenes can be extracted or purified by any method available to the skilled person. The alkanes/alkenes can be recovered in the organic phase. For instance, they can be extracted with an organic solvent, for instance with hexane. But alkanes/alkenes might also be recovered from the gas phase of the culture by condensation.

Production of Alkanes/Alkenes in a Recombinant Host Cell System

The present invention relates to the use of a recombinant host cell as described above for producing alkanes/alkenes from fatty acids, especially free fatty acid. It also relates to a method for producing alkanes/alkenes from fatty acids, wherein a recombinant host cell as described above is cultured under conditions effective to express the fatty acid decarboxylase of the present invention.

Accordingly, the present invention relates to a cell culture comprising a recombinant host cell as described above cultured under conditions effective to express the fatty acid decarboxylase of the present invention.

Optionally, the recombinant host cell can be cultured in a medium comprising fatty acids. Alternatively or in addition, the recombinant host cell produces or comprises fatty acids.

In the method, the recombinant host cell is preferably cultured in conditions for obtaining a biomass, preferably a biomass rich in lipid, especially fatty acids. Then, in a second step, the conversion of the fatty acids into alkanes/alkenes is initiated. For instance, if the fatty acid decarboxylase is already expressed in the recombinant host cell, the second step can be initiated by applying a blue photon-containing light to the recombinant host cell for allowing the fatty acid decarboxylase activity. Indeed, the inventors showed that the alkane production can be controlled by light, especially its wavelength. Blue light (>400 nm and <530 nm) allows the production of alkane while red light (>600 nm and <700 nm) does not. Then, in the method of the present invention, the alkane production can be modulated in vivo by light. Alternatively, if the expression of the fatty acid decarboxylase is controlled by an inducible promoter, the second step can be initiated by inducing the expression of the fatty acid decarboxylase and submitting cells to photons (300-540 nm). Moreover, light intensity (photons flux) modulates enzyme activity. A high photons flux increases enzyme activity whereas a low photons flux decreases enzyme activity.

Alternatively, the method can comprise the culture of the recombinant host cell in conditions conjointly promoting the production of a biomass, preferably rich in lipid, especially fatty acids, and the conversion of the fatty acids into alkanes/alkenes.

By "rich" is intended that the biomass comprises at least 20, 30, 40, 50, 60 or 70% in weight of lipids, especially fatty acids, by dry biomass.

The method may comprise an additional step of isolating or recovering the alkanes/alkenes from the recombinant host cell or from the culture medium.

The alkanes/alkenes can be extracted or purified by any method available to the skilled person. For instance, they can be extracted with an organic solvent, for instance with hexane. The alkanes/alkenes can be recovered in the organic phase.

One exemplary separation process is a two phase (biphasic) separation process. This process involves fermenting the genetically engineered host cells under conditions sufficient to produce alkanes/alkenes, allowing the alkanes/alkenes to collect in an organic phase, and separating the organic phase from the aqueous fermentation broth. This method can be practiced in both a batch and continuous fermentation setting.

The methods and uses according to the present invention for producing alkanes/alkenes can be used for preparing biofuel, materials useful in chemistry, in particular in cosmetics and other field such as plastics, resins, fibers, elastomers, pharmaceuticals, lubricants or gels.

The alkenes described herein can be used as or converted into a fuel. One of ordinary skill in the art will appreciate that, depending upon the intended purpose of the fuel, different alkenes can be produced and used. For example, branched alkenes may be desirable for automobile fuel that is intended to be used in cold climates. In addition, when the alkenes described herein are used as a feedstock for fuel production, one of ordinary skill in the art will appreciate that the characteristics of the olefin feedstock will affect the characteristics of the fuel produced. Hence, the characteristics of the fuel product can be selected for by producing particular alkenes for use as a feedstock.

Using the methods described herein, biofuels having desired fuel qualities can be produced from alkenes. Biologically produced alkenes represent a new source of biofuels, which can be used as jet fuel, diesel, or gasoline. Some biofuels made using alkenes have not been produced from renewable sources and are new compositions of matter.

Fatty Acid Dosage

The fatty acid decarboxylase of the invention is also useful for quantification of free fatty acids and can be included in a kit for quantification of free fatty acids. In particular, the present invention relates to a method for quantifying fatty acids in a sample, comprising contacting the sample with a fatty acid decarboxylase of the present invention in conditions suitable for converting fatty acids into alkanes/alkenes, recovering the alkanes/alkenes and quantifying the alkanes/alkenes. The sample can be a food sample or a biological sample, in particular a biological fluid sample such as blood, serum, plasma, urine and the like. The produced alkanes/alkenes can be extracted with an organic solvent and quantified, in particular by gas chromatography coupled to flame ionization detector and mass spectrometry (GC-FID-MS).

In a particular embodiment, the fatty acid decarboxylase of the invention is also useful for quantification of total fatty acids and can be included in a kit for quantification of total fatty acids. In particular, the present invention relates to a method for quantifying fatty acids in a sample, comprising contacting the sample with a lipase in conditions suitable for converting fatty acids into free fatty acids and quantifying the free fatty acids as detailed above. Accordingly, the method may comprise contacting the sample with a lipase in conditions suitable for converting fatty acids into free fatty acids, contacting a fatty acid decarboxylase of the present invention in conditions suitable for converting fatty acids into alkanes/alkenes, recovering the alkanes/alkenes and quantifying the alkanes/alkenes. The produced alkanes/alkenes can be extracted with an organic solvent and quantified.

When the fatty acid decarboxylase converts fatty acids into alkanes/alkenes, it produces CO2 as co-product. Then, in an alternative method, the present invention relates to a method for quantifying fatty acids in a sample, comprising contacting the sample with a fatty acid decarboxylase of the present invention in conditions suitable for converting fatty acids into alkanes/alkenes, recovering $CO_2$ and quantifying the $CO_2$. The amount of $CO_2$ can be measured by any method known by the person skilled in the art, for instance Gas chromatography-mass spectrometry (GC-MC).

In an additional aspect, the inventors observed that the fluorescence of the fatty acid decarboxylase varies as a function of the substrate concentration. Therefore, the fluorescence variation provides an additional means for quantifying fatty acids in a sample. Then, in an additional alternative method, the present invention relates to a method for quantifying fatty acids in a sample, comprising contacting the sample with a fatty acid decarboxylase of the present invention in conditions suitable for converting fatty acids into alkanes/alkenes, and measuring the fluorescence emitted by the fatty acid decarboxylase. Preferably, the fluorescence is measure at a wavelength from 500 to 700, kinetics are preferably performed at about 540 nm.

Of course, the method for quantifying fatty acids in a sample can combine several methods as detailed above, e.g. quantifying the alkanes/alkenes and $CO_2$, quantifying the alkanes/alkenes and measuring the enzyme fluorescence, quantifying $CO_2$ and measuring the enzyme fluorescence, or the combination of the three parameters.

The fatty acid dosage is useful for diagnosing diseases, for instance liver diseases (WO15089102), diabetes and preeclampsia (WO13170369).

Fatty Acid Removal

The fatty acid decarboxylase of the invention can also be useful for removing free fatty acids from a composition, for instance from alimentary oils, in particular refined alimentary oils. Indeed, the use of the fatty acid decarboxylase of the invention can allow the decarboxylation of fatty acids without any chemical process. Therefore, the present invention relates to the use of a polypeptide as defined above for decarboxylation of fatty acids, thereby removing fatty acids, or to a method for removing free fatty acids from a composition comprising contacting the fatty acid decarboxylase of the invention with the composition in conditions suitable for decarboxylating the free fatty acids of the composition.

Further aspects and advantages of this invention are disclosed in the following experimental section, which should be regarded as illustrative and not limiting the scope of this application.

Upper panel: portion of the chromatogram corresponding to the labeled pentadecane product; control: homogenate pre-heated at 95° C. for 30 minutes. Lower panel: mass spectrum of the labeled pentadecane.

Figure 1:
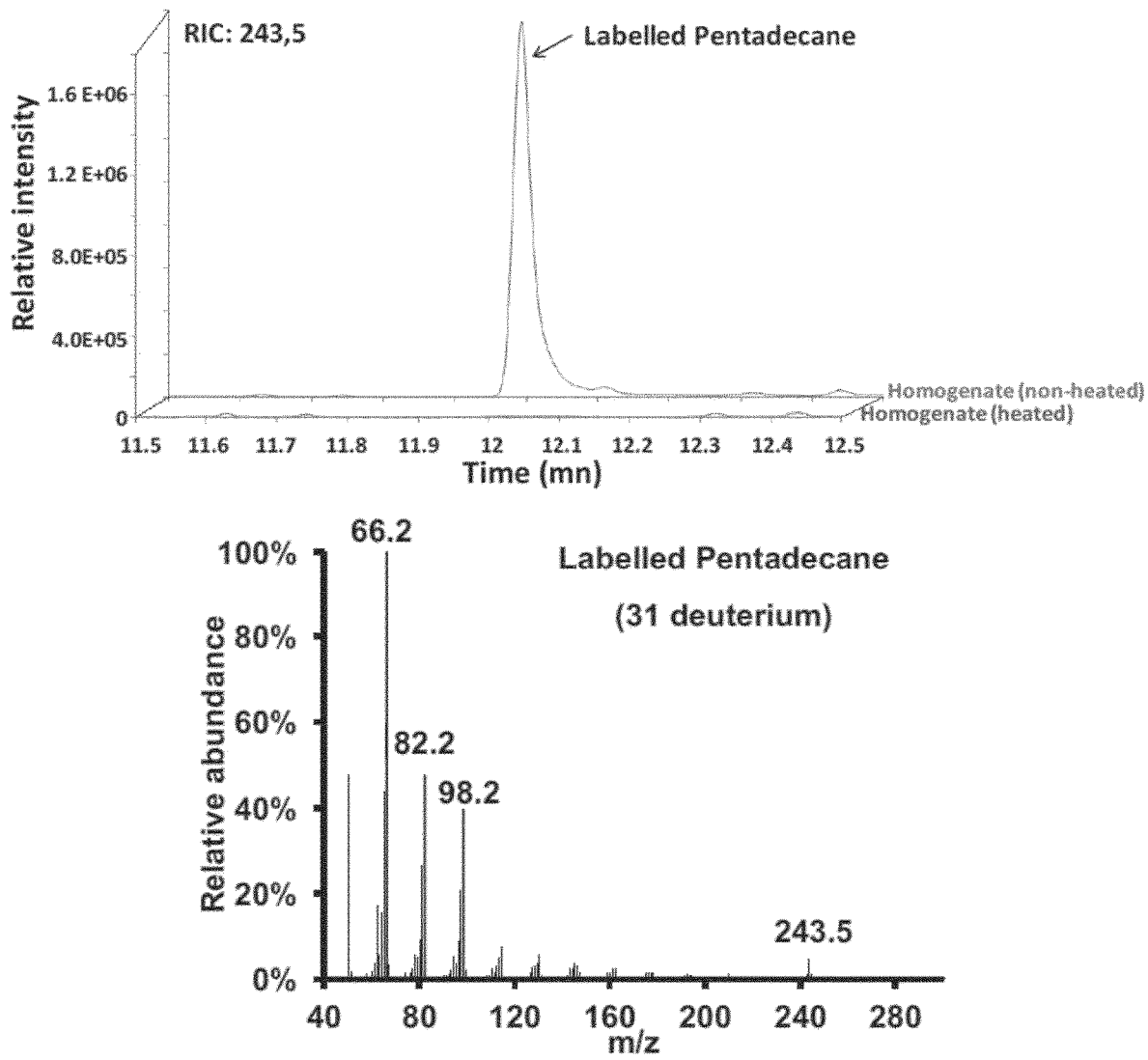
FIG. 1. Detection of an alkane synthase activity in a *Chlorella* homogenate. A cell homogenate of *Chlorella variabilis* NC64A was incubated overnight in a sealed vial with perdeuterated (D31) palmitic acid. The hydrocarbons of the gas phase were extracted by solid phase microextraction (SPME) and analyzed by gas chromatography coupled to mass spectrometry (GC-MS). Ions corresponding to m/z=243.5±0.5 were extracted.
Figure 2:
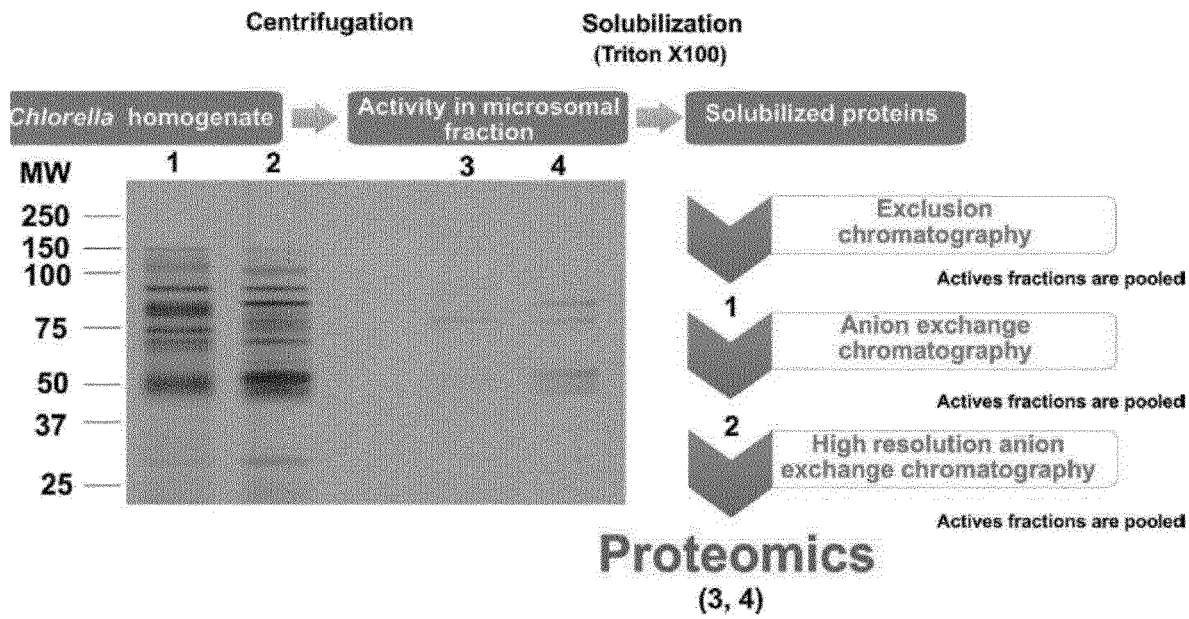

FIG. 2. Summary of the procedure of partial purification of the alkane synthase and analysis of protein profiles at various steps of the purification Alkane synthase activity assays were performed on cell fractions and elution fractions as described in FIG. 1 for the cell homogenate. Protein electrophoresis was performed on a 10% gel acrylamide under denaturating conditions. 1: after gel filtration; 2: after fast flow Q; 3 and 4: after Mono Q (fractions sent for proteomic analysis).

Figure 3:
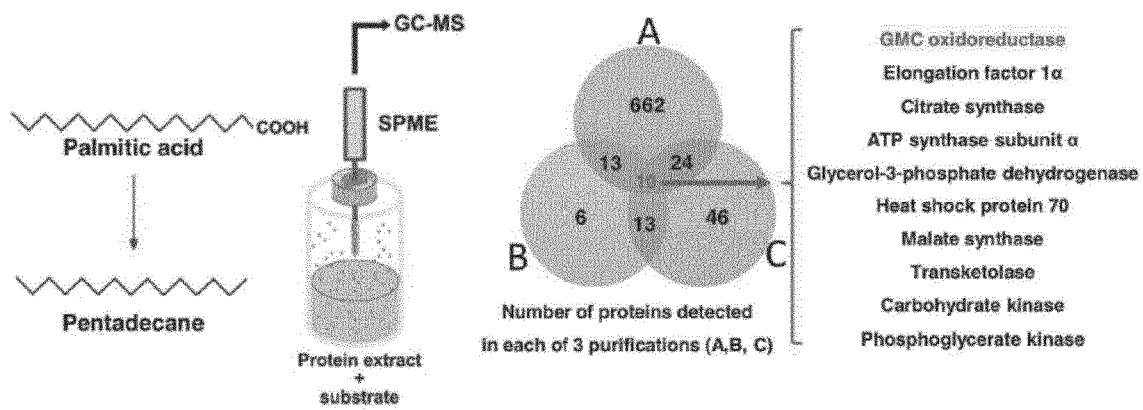

FIG. 3. Number of proteins detected by proteomic analysis after each of 3 purifications and list of the 10 proteins in common. Three independent purifications were performed (A,B,C).

Figure 4:
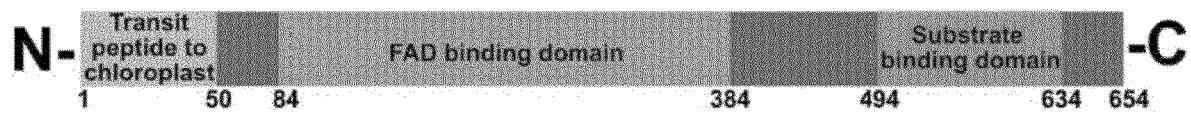

FIG. 4. The *Chlorella* alkane synthase is a chloroplast-predicted GMC oxidoreductase. Data were retrieved from PFAM and Protparam. Amino acids: 654; Molecular weight: 69070 Da Theoretical pI: 9.075. Predicted to be located in the chloroplast by Predalgo.

Figure 5:
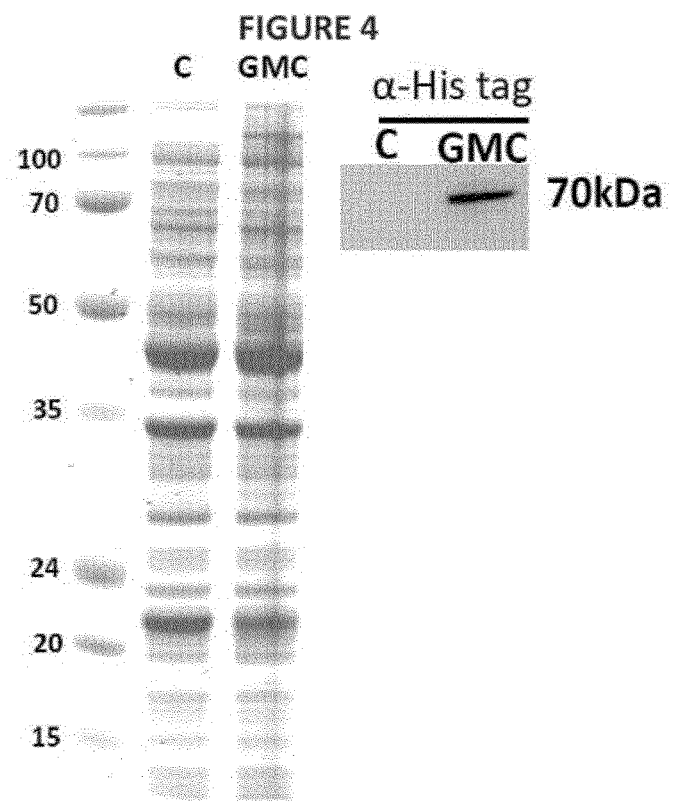

FIG. 5. Analysis of proteins in *E. coli* cells expressing the *Chlorella* GMC oxidoreductase. The *Chlorella* enzyme was expressed as a C-terminal His-tagged protein. Left: total protein profile as seen by SDS polyacrylamide gel electrophoresis. Right: Western blot using anti-His antibodies. C: control strain with empty vector; GMC: strain expressing the *Chlorella* GMC oxidoreductase.

Figure 6:
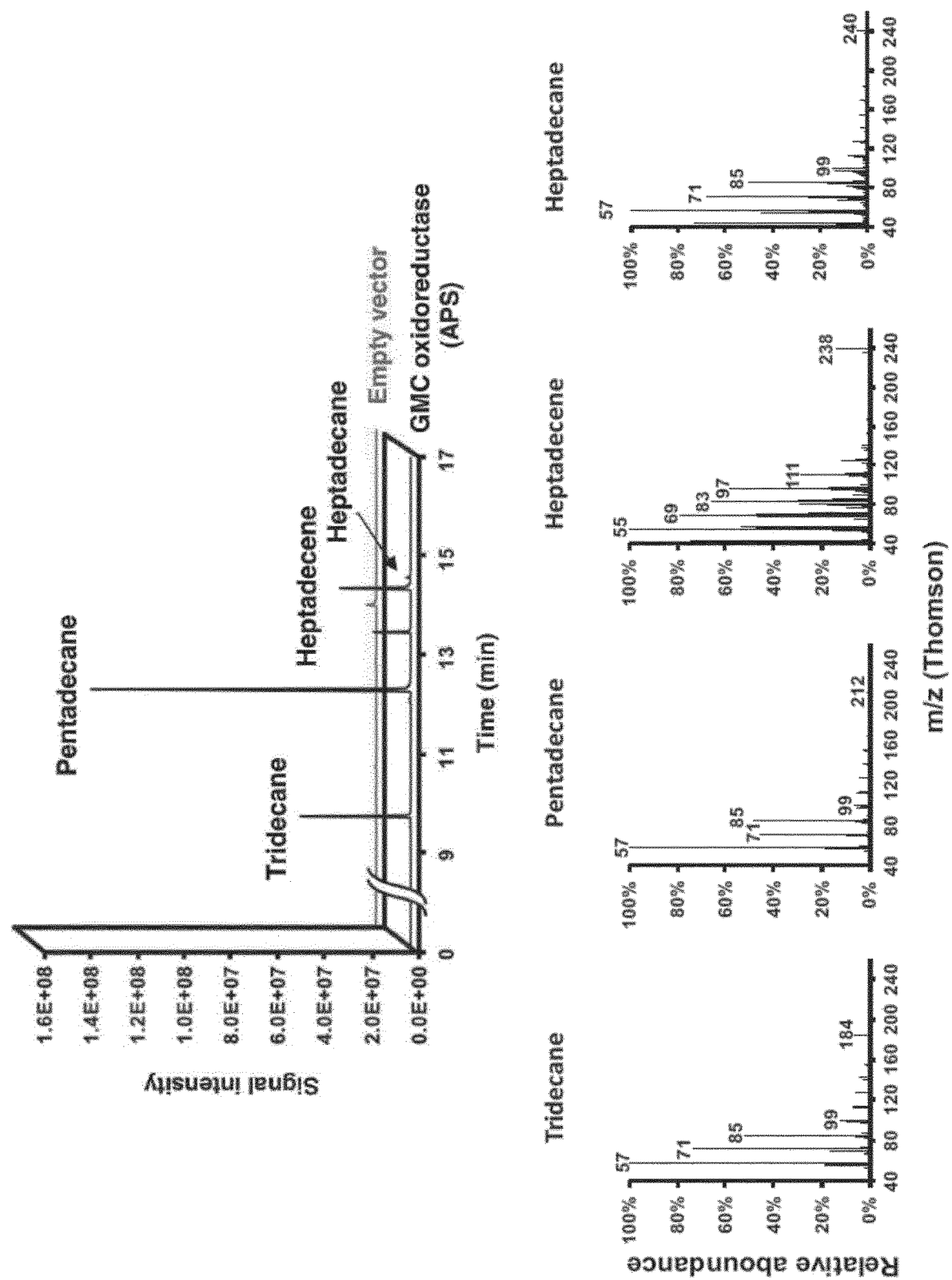

FIG. 6. Analysis of hydrocarbon content in *E. coli* cells expressing the *Chlorella* GMC oxidoreductase. Cells were saponified and hydrocarbon content was analyzed by SPME and GCMS. It should be highlighted that no fatty acid substrate was added. Upper panel: region of the chromatograms corresponding to the hydrocarbons. Lower panels: mass spectra of the alkanes detected. Control: strain with empty vector; GMC: strain expressing the *Chlorella* GMC oxidoreductase. Quantified data show mean±s.d. (n=3).

Figure 7:
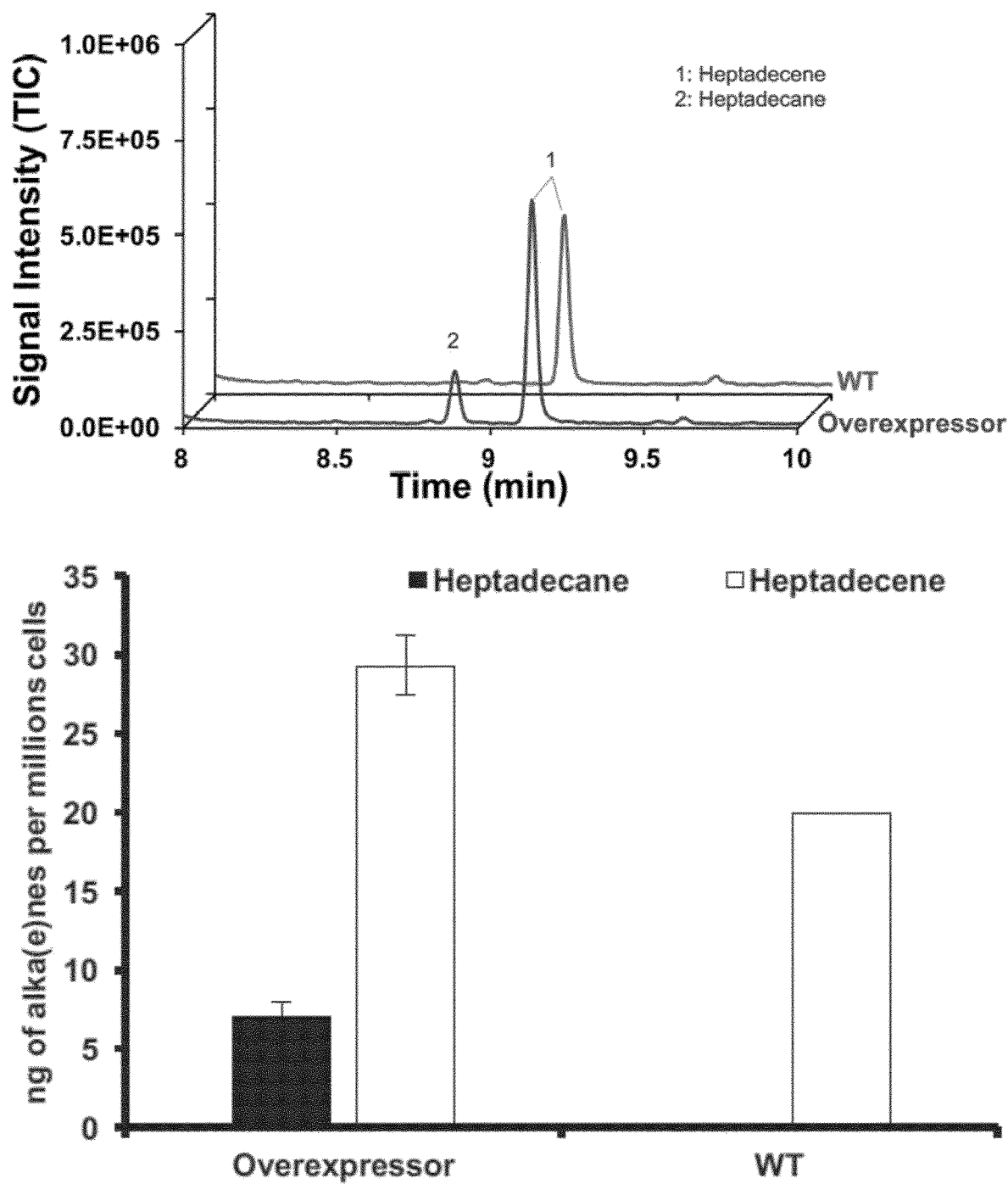

FIG. 7. Analysis of hydrocarbons in a transgenic microalga expressing the GMC oxidoreductase. Hydrocarbons were analyzed by GC-MS in a strain of the microalga *Chlamydomonas reinhardtii* in which the chloroplastic genome has been transformed with a gene encoding the GMC oxidoreductase. Upper panel: portion of the GC chromatogram showing the hydrocarbon peaks. Lower panel: quantification of the hydrocarbons. WT: wild type strain. GMC OE: strain expressing the *Chlorella* GMC oxidoreductase.

FIG. 8. Multiple alignment (A) and phylogenetic tree (B) of the GMC oxidoreductase family. The multiple alignment was built with Clustal O (1.2.1) using sequences from *Chlorella* (SEQ ID No 1); *Chlamydomonas* (SEQ ID No 5); *Coccomyxa* (SEQ ID No 9); *Volvox* (SEQ ID No 10); *Ectocarpus* (SEQ ID No 11); *Emiliania* (SEQ ID No 12); *Aureococcus* (SEQ ID No 13); *Phaeodactylum* (SEQ ID No 7); *Nannochloropsis* (SEQ ID No 14). The unrooted phylogenetic tree was built using a set of 56 GMC oxidoreductase protein sequences from various origin (neighbor-joining method). The *Chlorella* GMC oxidoreductase is boxed.

Figure 9:
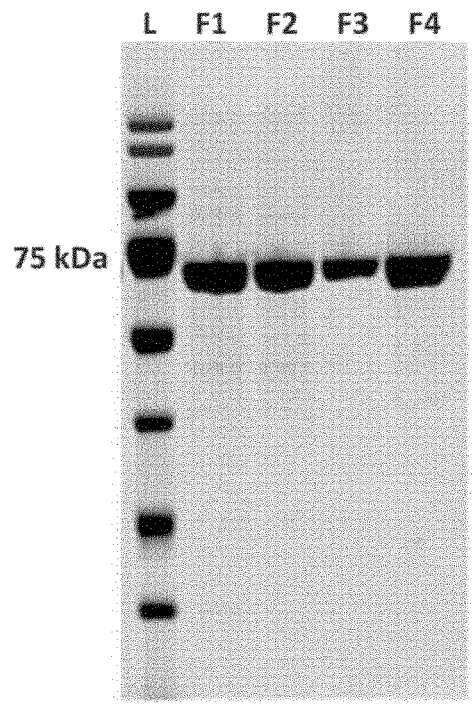

FIG. 9. Purified fractions of the recombinant *Chlorella* GMC oxidoreductases. The enzyme was expressed in *E. coli* as a N-terminal His-tagged protein and purified on a Ni column. F1 to F4 are elution fractions. L: molecular weight ladder.

Figure 10:
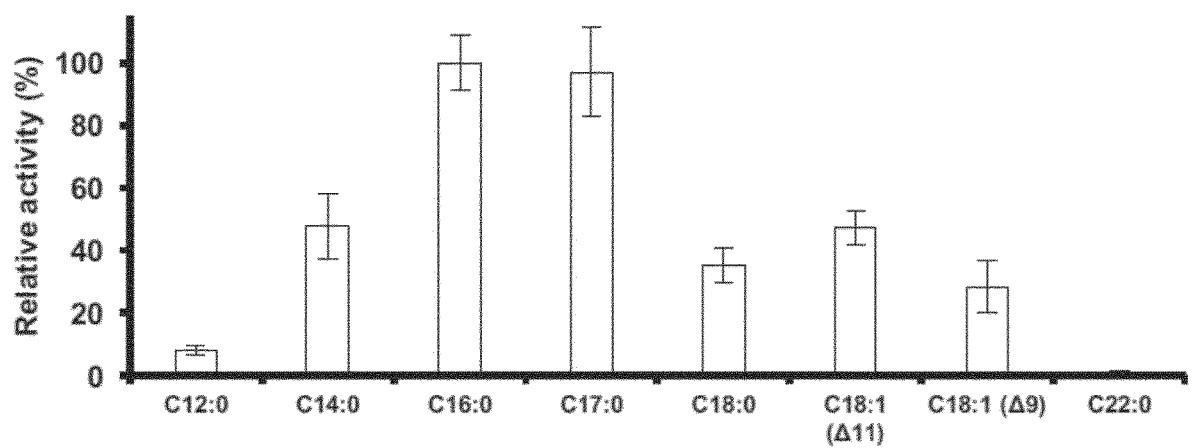

FIG. 10. Relative activity of the *Chlorella* GMC oxidoreductase on various fatty acids. The purified recombinant enzyme was incubated with fatty acids of various chain length under white light and products were analysed by GC-MS. Quantified data show mean±s.d. (n=3).

Figure 11:
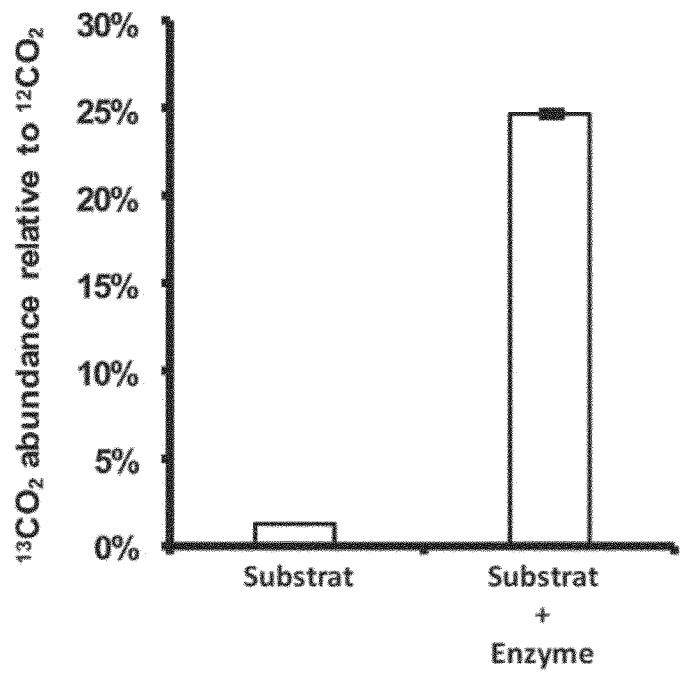

FIG. 11: $CO_2$ as co-product of the decarboxylation catalyzed by the alkane synthase. Relative quantification of $^{13}CO_2$ released upon incubation of 1-$^{13}C$-palmitate with the purified recombinant enzyme. Quantified data show mean±s.d. (n=3).

Figure 12:
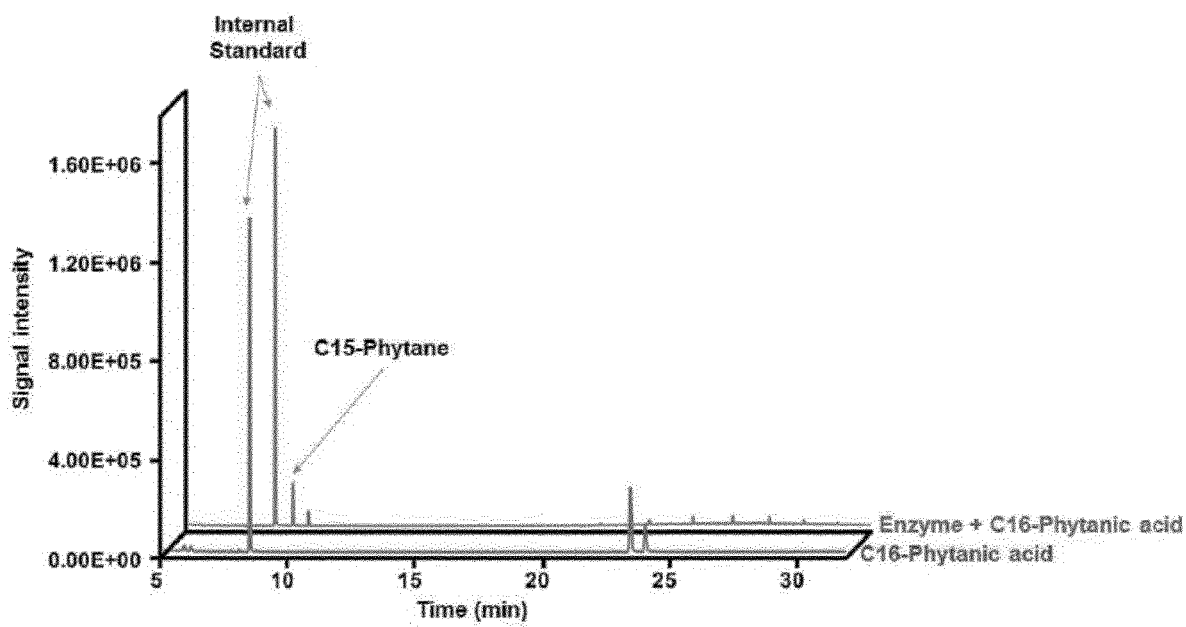

FIG. 12: The *Chlorella* GMC oxidoreductase converts terpenoic acids into methyl alka(e)nes. The purified recombinant enzyme was incubated with phytanic acid under white light and products were analysed by GC-MS.

Figure 13:
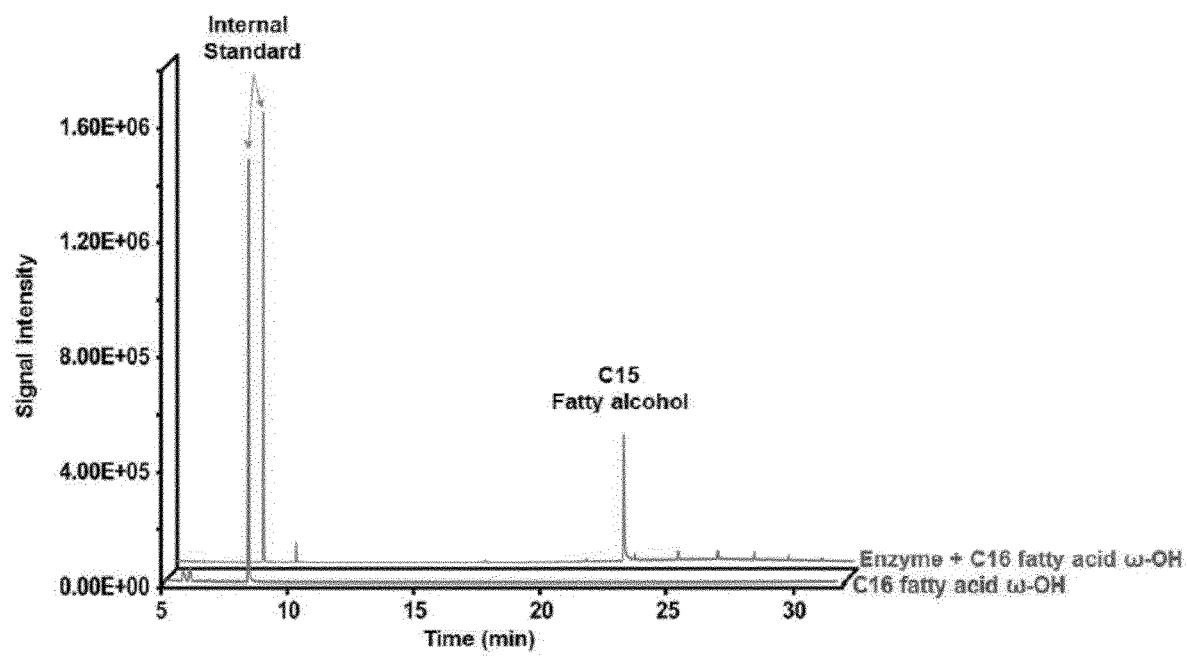

FIG. 13: The *Chlorella* GMC oxidoreductase converts hydroxy fatty acids into alkanols. The purified recombinant enzyme was incubated with hydroxypalmitate under white light and products were analysed by GC-MS.

Figure 14:
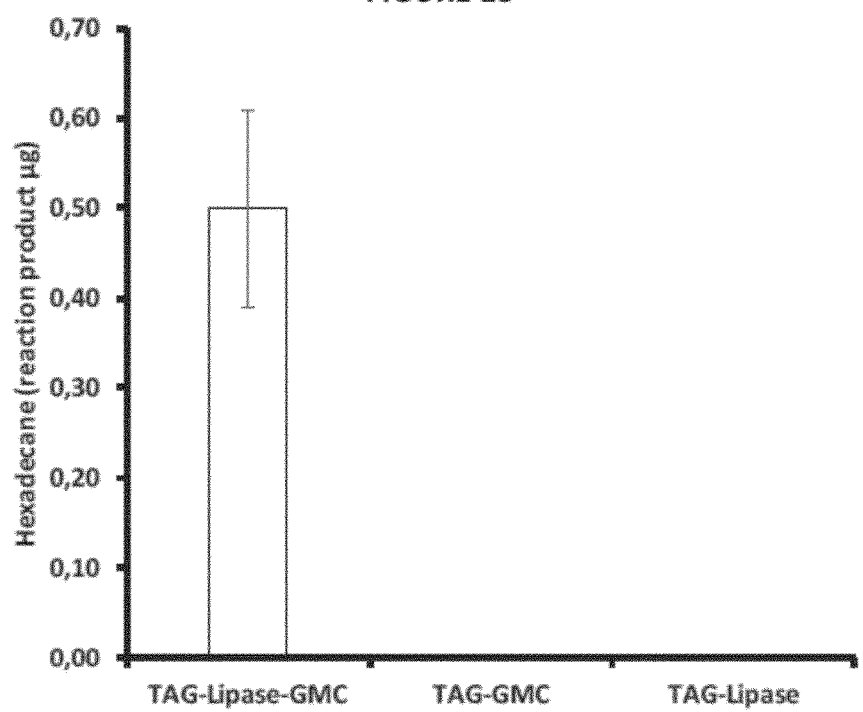

FIG. 14. In vitro production of alkanes from fatty acids using GMC oxidoreductase in combination with a lipase. Purified *Chlorella* GMC reductase and *Rhizopus* lipase were incubated with glyceryl triheptadecanoate and products were analysed by GC-MS. Quantified data show mean±s.d. (n=3).

Figure 15:
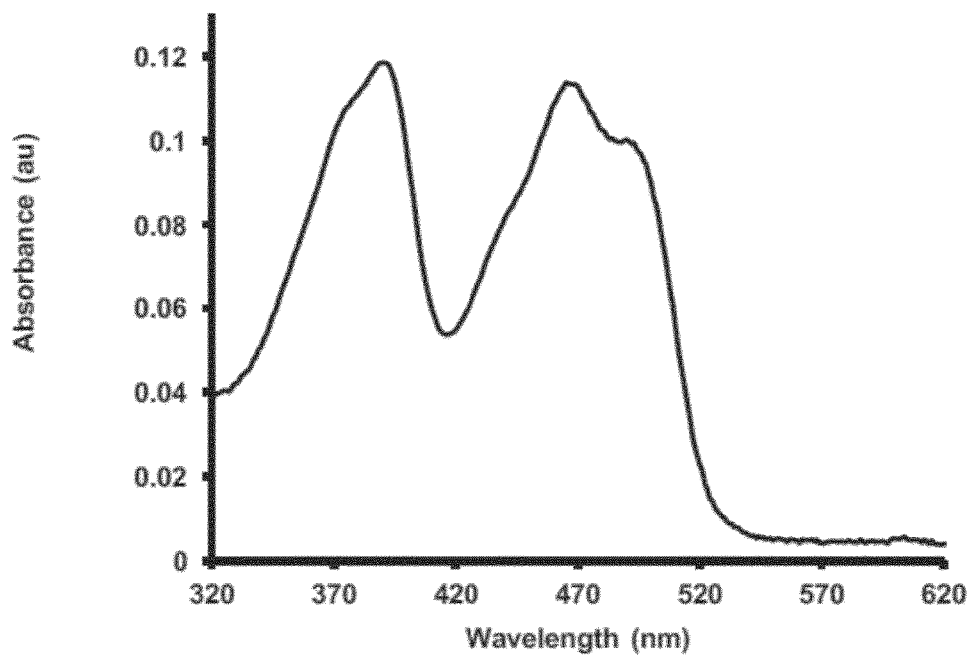

FIG. 15: Absorption spectrum of the *Chlorella* GMC oxidoreductase.

Figure 16:
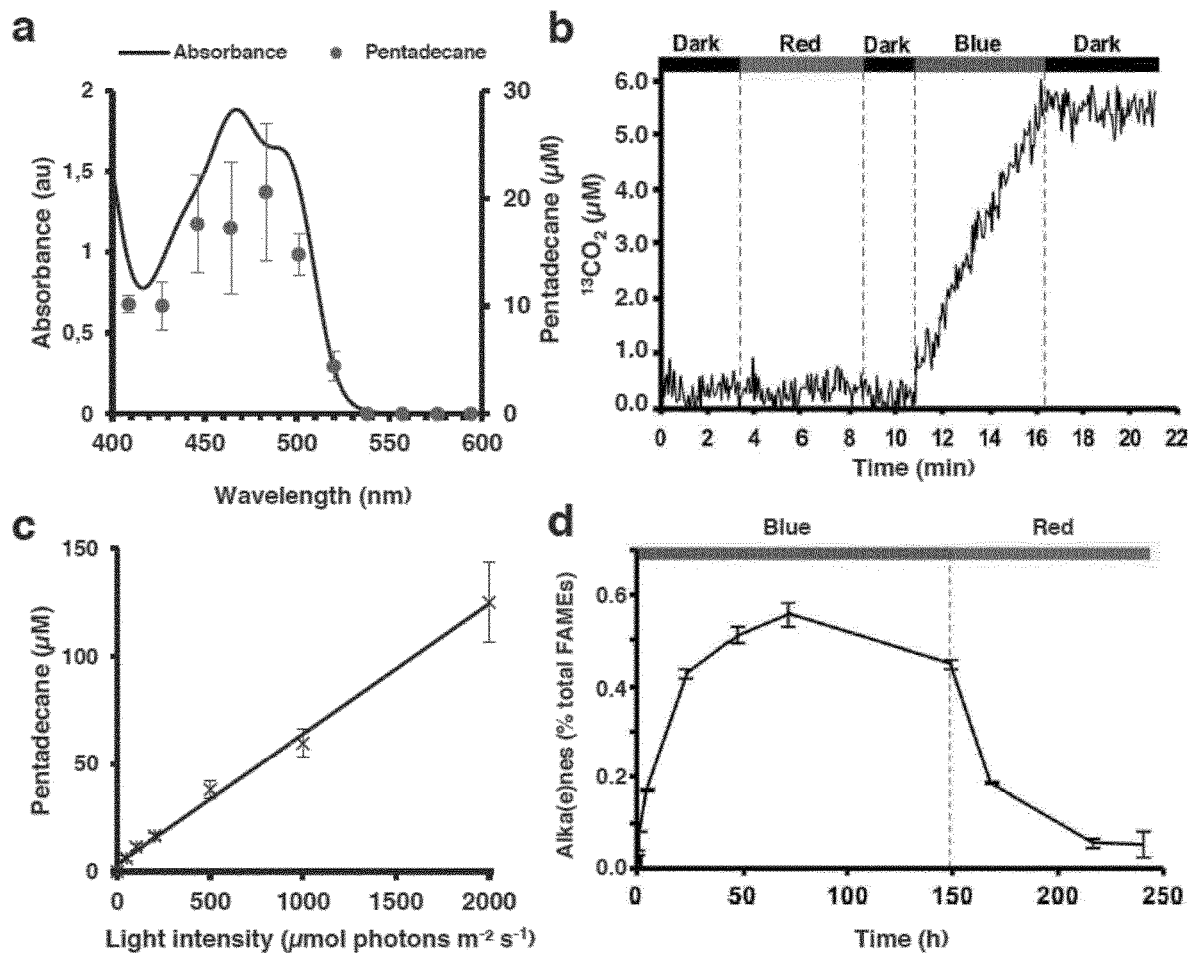

FIG. 16: Light dependency of the algal GMC oxidoreductases. a, Absorbance spectrum and action spectrum of the *Chlorella* GMC oxidoreductase. b, Monitoring of $^{13}CO_2$ release by membrane inlet mass spectrometry upon incubation of 1-$^{13}C$-palmitate with the *Chlorella* enzyme. The reaction mixture was exposed to successive light (blue or red) conditions at 850 µmoles photons $m^{-2}$ $s^{-1}$. c, Dependence of *Chlorella* GMC oxidoreductase activity with light intensity. d, Variation of total hydrocarbons in *Chlamydomonas* cells during a culture in blue and then red light at 30 µmoles photons $m^{-2}$ $s^{-1}$. Quantified data show mean±s.d. (n=3).

Figure 17:
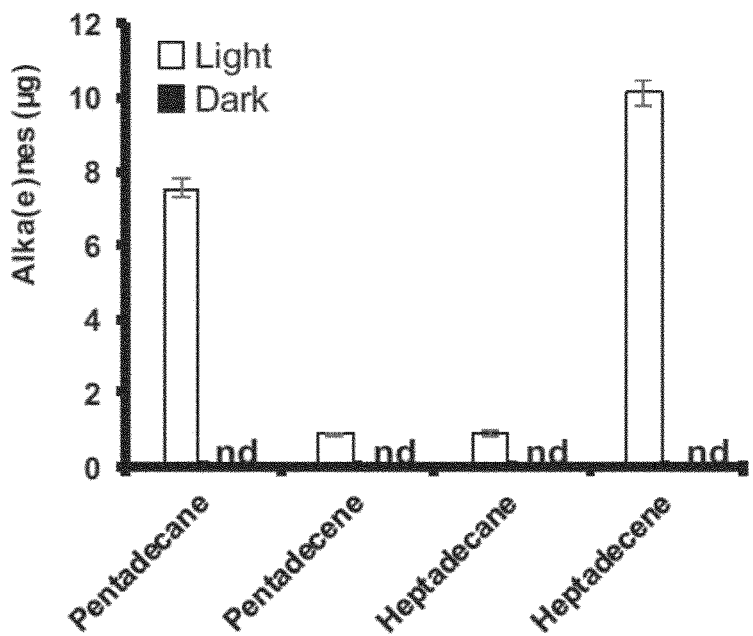

FIG. 17: Quantification of hydrocarbons in *E. coli* cells expressing the *Chlorella* alkane synthase and cultivated under dark or light (1000 µmol photons $m^{-2}$ $s^{-1}$ of white light containing photons from 400 to 800 nm). Quantified data show mean±s.d. (n=3). Nd, not detected.

Figure 18:
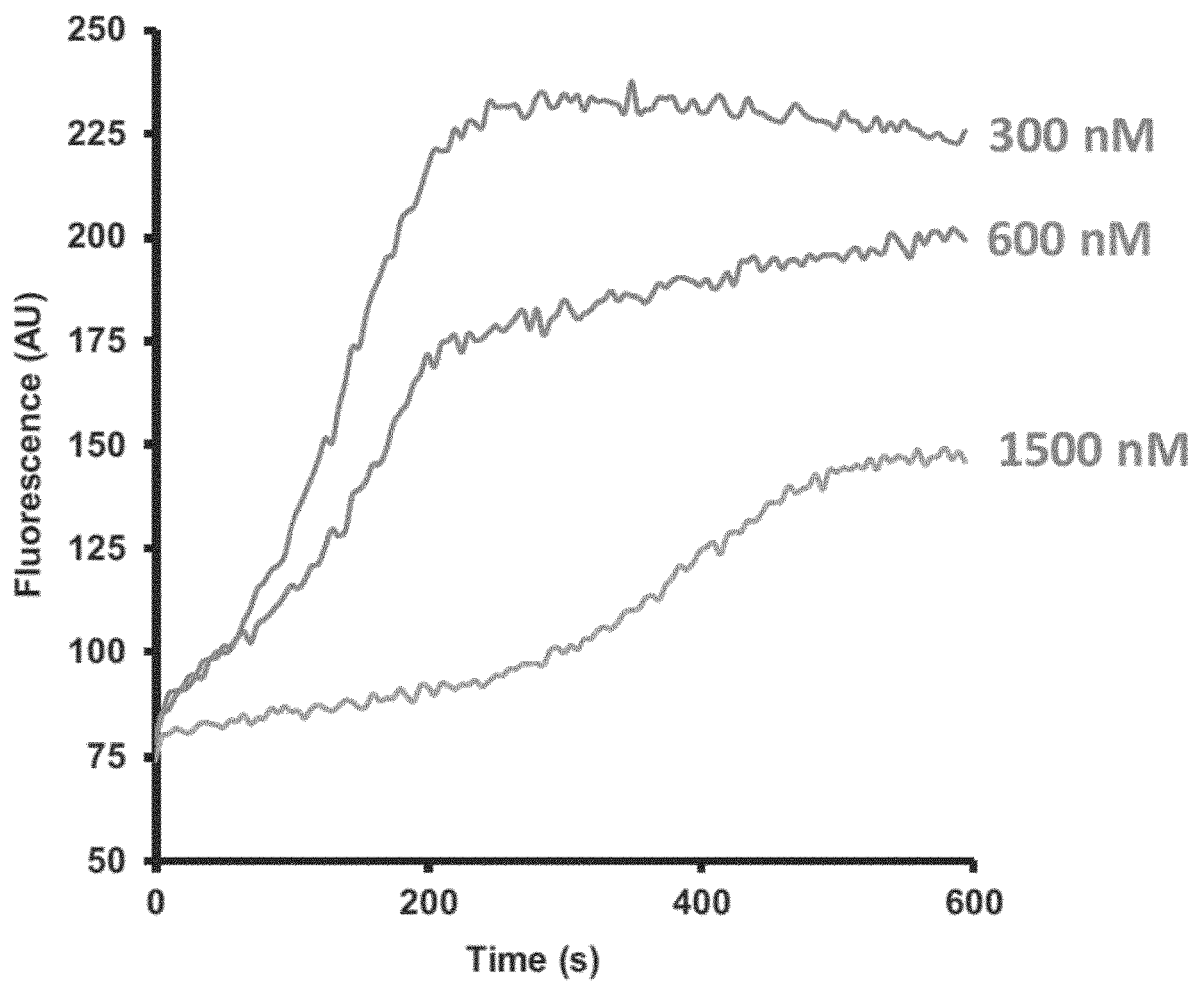

FIG. 18. Kinetics of GMC oxidoreductase fluorescence in presence of substrate. Excitation was at 450 nm±5 and emission at 540 nm. Various concentrations of palmitic acid were used.

Figure 19:
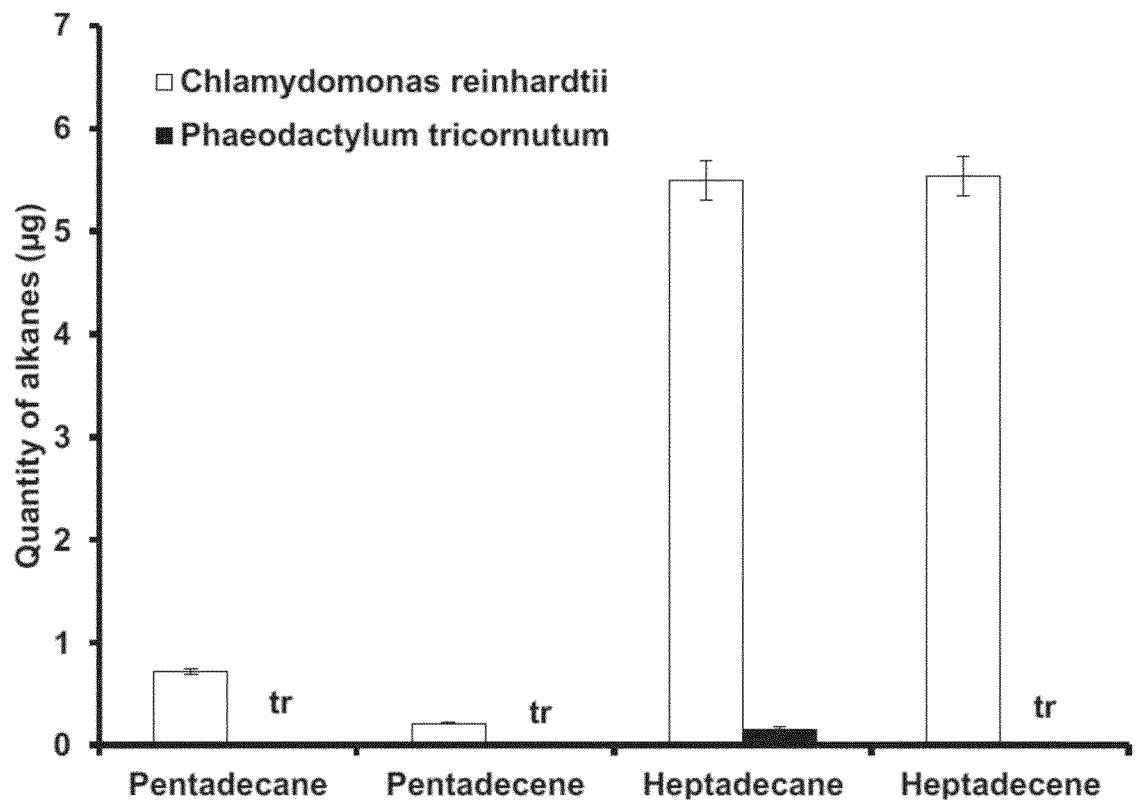

FIG. 19: Quantification of hydrocarbons in *E. coli* cells expressing the *Chlamydomonas* or the *Phaeodactylum* GMC oxidoreductase. Cells were transmethylated and hydrocarbon content was analyzed by solvent extraction and GCMS. It should be highlighted that no fatty acid substrate was added. No alkanes were detected in *E. coli* cells transformed with an empty vector. Tr, traces. Quantified data show mean±s.d. (n=3).

Figure 20:
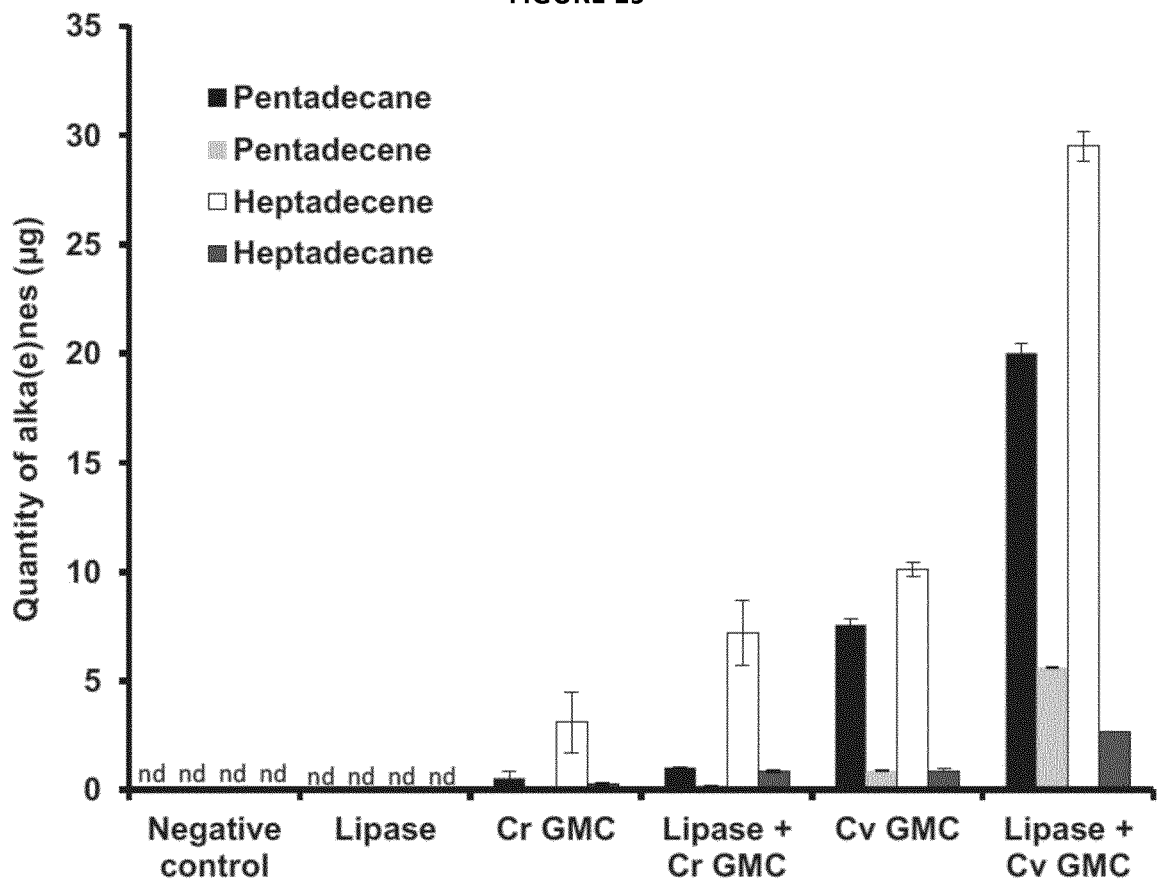

FIG. 20: Quantification of hydrocarbons in *E. coli* cells co-expressing an algal GMC oxidoreductase and a lipase. Cells were transmethylated and hydrocarbon content was analyzed by solvent extraction and GCMS. It should be highlighted that no fatty acid substrate was added. Negative control: *E. coli* cells transformed with an empty vector. Nd, not detected. Cr: *Chlamydomonas reinhardtii*; Cv: *Chlorella variabilis*. The lipase is from the bacterium *Staphylococcus hyicus* (Uniprot P04635). Quantified data show mean±s.d. (n=3).

BRIEF DESCRIPTION OF THE SEQUENCE LISTING

| SEQ ID No | Description |
| --- | --- |
| 1 | Amino acid sequence of GMC protein from *Chlorella variabilis* NC64A without the putative chloroplast transit peptide |
| 2 | Amino acid sequence of GMC protein from *Chlorella variabilis* NC64A with the putative chloroplast transit peptide |
| 3 | Amino acid sequence of a GMC protein from *Chlorella variabilis* NC64A without the putative chloroplast transit peptide but with a histidine tag, thioredoxin and a TEV (Tobacco Etch Virus) cleavage site at the N terminal end |
| 4 | consensus sequence |
| 5 | Amino acid sequence of GMC protein from *Chlamydomonas reinhardtii* without the putative chloroplast transit peptide |
| 6 | Amino acid sequence of GMC protein from *Chlamydomonas reinhardtii* with the putative chloroplast transit peptide |
| 7 | Amino acid sequence of GMC protein from *Phaeodactylum tricornutum* without the putative chloroplast transit peptide |
| 8 | Amino acid sequence of GMC protein from *Phaeodactylum tricornutum* with the putative chloroplast transit peptide |
| 9 | Amino acid sequence of GMC protein from *Coccomyxa subellipsoidea* without the putative chloroplast transit peptide |
| 10 | Amino acid sequence of GMC protein from *Volvox carteri* without the putative chloroplast transit peptide |
| 11 | Amino acid sequence of GMC protein from *Ectocarpus siliculosus* without the putative chloroplast transit peptide |
| 12 | Amino acid sequence of GMC protein from *Emiliania huxleyi* without the putative chloroplast transit peptide |
| 13 | Amino acid sequence of GMC protein from *Aureococcus anophagefferens* without the putative chloroplast transit peptide |
| 14 | Amino acid sequence of GMC protein from *Nannochloropsis gaditana* without the putative chloroplast transit peptide |
| 15 | Nucleic acid sequence encoding SEQ ID No 1 |
| 16 | Nucleic acid sequence encoding SEQ ID No 5 |
| 17 | Nucleic acid sequence encoding SEQ ID No 7 |
| 18 | Nucleic acid sequence encoding SEQ ID No 9 |
| 19 | Nucleic acid sequence encoding SEQ ID No 10 |
| 20 | Nucleic acid sequence encoding SEQ ID No 11 |
| 21 | Nucleic acid sequence encoding SEQ ID No 12 |
| 22 | Nucleic acid sequence encoding SEQ ID No 13 |
| 23 | Nucleic acid sequence encoding SEQ ID No 14 |

Examples

Here, the inventors identified in the model microalga *Chlorella variabilis* NC64A an enzyme catalyzing the synthesis of alka(e)nes. The enzyme was partially purified using deuterium-labeled palmitic acid as a substrate and solid phase microextraction to capture the pentadecane product. A candidate protein belonging to the Glucose-Methanol-Choline oxidoreductase family was identified by proteomic analysis of three independent partial purifications. Heterologous expression of this *Chlorella* candidate gene in *Escherichia coli* resulted in the production of linear hydrocarbons from 13 to 17 carbons, showing that a single enzyme is sufficient to produce fuel-like alka(e)nes. The *Chlorella* alkane synthase is 69 kDa chloroplast-predicted protein using FAD as a cofactor. In vitro assays show that it can use C12 to C22 fatty acids to form alka(e)nes. The activity of this enzyme was found to be strictly dependent on presence of photons from 400 to 540 nm but could also work from 300 to 400 nm. These results thus expand the current knowledge on the catalytic repertoire of the Glucose-Methanol-Choline oxidoreductase family and open a new avenue for the renewable and light-driven production of alka(e)nes in microorganisms.

Results

Partial Purification of an Alkane Synthase Activity from *Chlorella variabilis* NC64A The inventors have shown that various microalgae, including *Chlorella variabilis* NC64A, had the capacity to synthesize C15-C17 alkanes and alkenes. In the same work, they have also shown that deuterated palmitic acids added exogenously to *Chlorella* cultures can be converted into alkanes and alkenes. In order to identify the enzymatic pathway of alkane synthesis in microalgae, they have chosen a traditional purification approach based on the use of deuterium-labeled palmitic acid as substrate.

The first step was to confirm that an enzyme activity can be measured in a *Chlorella* cell homogenate. Deuterated palmitic acid was added to a cell homogenate and incubated overnight in a sealed vial. The expected pentadecane product was extracted by solid phase micro-extraction (SPME) and analyzed by gas chromatography coupled to mass spectrometry (GC-MS). A peak at 12.03 minutes corresponding to labelled pentadecane could be detected on intact cells but was absent on pre-heated control homogenate (FIG. 1).

This experiment thus showed that *Chlorella* homogenate has an alkane synthesis enzyme activity. Because the alkane synthesis pathways identified in most organisms have an aldehyde intermediate, the inventors performed the same experiment using labelled C16 aldehyde but labelled pentadecane could not be detected.

The labelled palmitic acid was thus used to assay activity in all the purification procedure (FIG. 2). When cells were centrifuged at 50000 g, most activity was found in the supernatant fraction. But after a second centrifugation at 105000 g, the activity was found mostly in the pellet (microsomal fraction). Different detergents were tested to solubilize the activity and the most efficient were found to be Triton X100.

Some preliminary tests were then performed before purifying further the activity. Several co-factors such ferredoxine, ferredoxine reductase, NADP, NADPH and ATP were added in different combinations on the solubilized microsomal fraction. None of them were found to increase the activity and they were not added to the assays on purified fractions. The inventors also observed that in three days, the solubilized microsomal fraction activity stored at 4° C. decreased by 90%, indicating that the whole purification process had to be performed within a few days.

The partial purification of the solubilized activity involved a first step of gel filtration with a preparative column Superdex 200 and then two anion exchange columns, a fast flow Q and a final more resolutive mono Q. Most fractions were assayed for alkane synthase activity using the assay previously described. Protein content of the most active fractions was analyzed by electrophoresis on an acrylamide gel under denaturing conditions (FIG. 2).

Three independent partial purifications were performed. Fractions with the highest activity after the final purification step were sent for proteomic analysis. By taking a cut off of 2 peptides counts at least, only ten proteins were common between the three purifications (FIG. 3). Nine of these proteins were clear homologs to well-characterized enzymes. The only candidate belonging to a group of enzymes with a diverse range of activities was a putative enzyme from the Glucose-Methanol-Choline (GMC) oxidoreductase family. This candidate was also the one with the highest peptide count. It was therefore chosen for heterologous expression.

The *Chlorella* Alkane Synthase is a Member of the GMC Oxidoreductase Family

The gene encoding the *Chlorella* GMC oxidoreductase was not completely covered by publicly available ESTs. A cDNA around 2 kb was cloned using a total RNA extract from *Chlorella*. It encoded a 69 kDa protein (FIG. 4) and was predicted to be localized to chloroplast by the microalgal sequence-adapted software Predalgo. The N-terminal chloroplast targeting signal is predicted to be 50 residue long. The TMHMM software predicted no transmembrane domain. This cDNA was expressed in *Escherichia coli* as a C-terminal His-tagged protein (FIG. 5). Presence of the recombinant protein was checked by western blotting. Analysis by SPME and GC-MS of the volatile products of *E. coli* cells expressing the GMC oxidoreductase showed the presence of long chain alkanes from 13 to 17 carbons, which were absent from *E. coli* cells transformed with an empty vector (FIG. 6). These results therefore demonstrated that the expression of the *Chlorella* GMC oxidoreductase was sufficient to produce alkanes and alkenes in *E. coli*. In addition, in a *Chlamydomonas* strain whose chloroplastic genome was transformed with the cDNA encoding the *Chlorella* enzyme, an increase was noted in the heptadecene content, and heptadecane also appeared (FIG. 7). This result thus, indicates that the *Chlorella* enzyme is functional within a chloroplast.

Figure 8A:
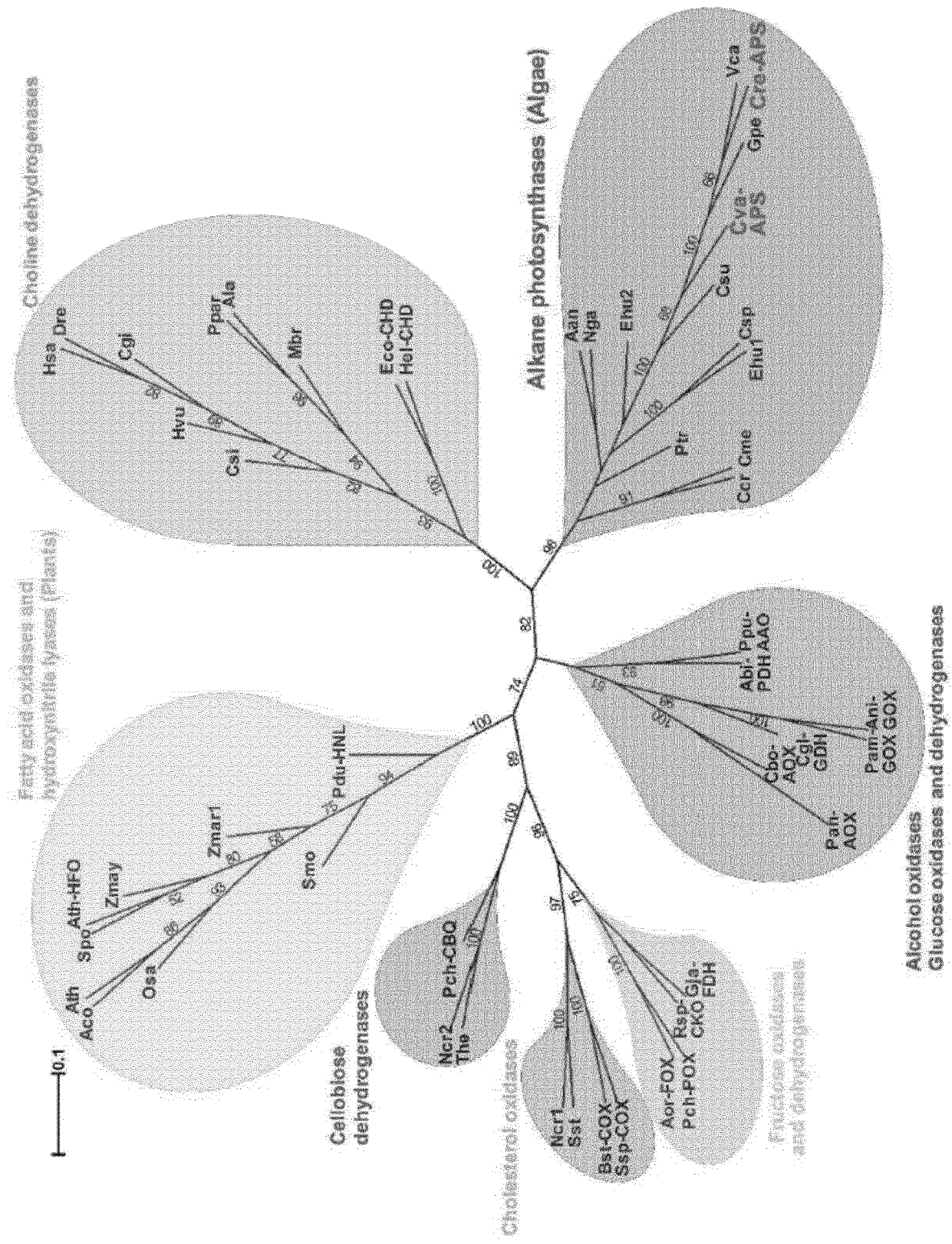

BlastP searches using the *Chlorella* GMC oxidoreductase or other biochemically characterized GMC oxidoreductases from other species were performed in public databases to retrieve a variety of GMC oxidoreductase protein sequences. Multiple alignment of algal sequences indicated that some *Chlorella* residues such as C372, R391, Y406, Q426, H512 and N515 were highly conserved in other algae (FIG. 8A) and an unrooted phylogenetic tree was performed (FIG. 8B). Blast searches indicated that in most organisms GMC oxidoreductases are single gene families. In *Chlorella variabilis* NC64A, the *Chlorella* alkane synthase is the only GMC oxidoreductase. The phylogenetic tree showed that the GMC oxidoreductase family consisted of at least 7 groups, one of which still had no biochemically-characterized member. Interestingly, sequences of brown macroalgae (*Ectocarpus*), of red macroalgae (*Chondrus*) and of microalgae from various origin (the Trebouxiophyceae *Chlorella*, the Chlorophyceae *Chlamydomonas* and *Volvox*, the Coccomyxaceae *Coccomyxa*, the Eustigmatophyceae *Nannochloropsis*, the Coccolithophyceae *Emiliana*, the Diatom *Phaeodactylum*) grouped together. The *Chlorella* enzyme is the first to be functionally characterized in this algal group of GMC oxidoreductases.

The *Chlorella* Alkane Synthase is a Light-Driven Photoenzyme Acting on a Variety of Fatty Acids In order to characterize further its activity, the *Chlorella* GMC oxidoreductase was expressed in *Escherichia coli* as a His-tagged protein and purified on a nickel column (FIG. 9). The purified recombinant was found to be active on a variety of saturated free fatty acids ranging from C12 to C22 carbons (FIG. 10), which explains the wide profile of fatty acids formed in *E. coli* (FIG. 6).

In order to determine the co-product of the reaction, the inventors used palmitic acid labelled with $^{13}C$ on the carboxylic group. They observed the production of $^{13}CO_2$ demonstrating that the enzyme releases $CO_2$ as a co-product, i.e. is a fatty acid decarboxylase. (FIG. 11)

To characterize further alkane synthase activity, substituted fatty acids were used as substrate. Phytanic acid (3,7,11,15-tetramethylhexadecanoic acid) was found to be converted into branched alkanes, indicating that the alkane synthase is active on terpenoic acids (FIG. 12). Use of 16-OH palmitic acid as substrate lead to the production of pentadecanol showing that the *Chlorella* GMC oxidoreductase could be used to produce fatty alcohols (FIG. 13).

In vitro, the alkane synthase cannot use TAGs (triacylglycerol) directly as substrate (FIG. 14). However, in presence of a TAG (triacylglycerol) lipase releasing fatty acids the production of hydrocarbons is observed. This observation shows that the GMC oxidoreductase could be used to produce hydrocarbons from oils and waste rich in lipids.

FIG. 15 shows that the FAD can absorb photons from 320 to 540 nm. This was consistent with the action spectrum of the enzyme (FIG. 16A).

To determine if the alkane synthase was a light-driven enzyme (photoenzyme) or a light-activated enzyme, the production of $CO_2$ was monitored during the reaction. The activity of the enzyme is driven by the presence of photons and stops immediately when light is turned off. (FIG. 16B). Production of pentadecane increases linearly with light intensity confirming the fact that the *Chlorella* GMC oxidoreductase is a photoenzyme (FIG. 16C). The light-dependency of the algal alkane synthase could be used to modulate hydrocarbon production of algal cells using light quality (blue or red) as observed on *Chlamydomonas reinhardtii* (FIG. 16D). The microalgae produce hydrocarbons in presence of blue photons, whereas in red, production stops and alkane content decreases. In *E. coli* cells expressing the alkane photosynthase hydrocarbons light can also be used as an inducer to select the time for an optimal production of alkanes and alkenes. (FIG. 17).

Substrate Concentration Modify Enzyme Fluorescence.

Based on the light dependence of the enzyme we suspect that enzyme fluorescence could change during the activity of the enzyme with or without substrate. To this aim, we made fluorescence spectrum and kinetics (FIG. 18). The inventors observed that fluorescence and kinetic drastically changes with substrate concentration. It can be useful to use fluorescence parameter to determine fatty acid concentrations.

The GMC Oxidoreductases from *Chlamydomonas* and *Phaeodactylum* are Also Alkane Synthases To investigate the possibility that other algal GMC oxidoreductases also have a fatty acid decarboxylase activity and are thus alkane synthases, the GMC oxidoreductases of another Chlorophyceae (*Chlamydomonas reinhardtii*) and a diatom (*Phaeodactylum tricornutum*) were expressed in *Escherichia coli* and total fatty acids and hydrocarbons of the bacterial cells were analyzed by GC-MS-FID. The *Chlamydomonas* enzyme caused the formation in *E. coli* cells of pentadecane and heptadecane as well as their mono-unsaturated analogs (FIG. 19). The same compounds were formed by the *Phaeodactylum* enzyme, albeit in lower amounts.

Co-Expressing a Lipase with a GMC Oxidoreductase Boost Alkane Synthesis in *E. coli*

Free fatty acid pools are usually small in living cells because free fatty acids are deleterious to membrane structure. In order to see if the production of alkanes and alkenes could be boosted in *E. coli* by increasing the amount of free fatty acids available, a bacterial lipase (Uniprot P04635) was coexpressed with the *Chlorella* or the *Chlamydomonas* alkane synthase (FIG. 20). This resulted in a two to three-fold increase in most hydrocarbons compared to the *E. coli* strains expressing the GMC oxidoreductases alone.

Discussion

Alkanes and alkenes are interesting compounds for biofuel production and alkenes are particularly interesting for chemical industry. In this work, using partial purification and proteomic analysis, the inventors were able to identify a microalgal alkane synthase from *Chlorella*. It is a member of the GMC oxidoreductase family. When expressed in *E. coli*, this protein alone is able to yield alkanes and alkenes. The main interest of this enzyme is its apparent capacity to catalyze a formal decarboxylation of free fatty acids to form saturated hydrocarbons and the fact that it is a photoenzyme. Mechanism and possibly cofactor requirements are expected to be different from the bacterial cytochrome P450 alkane synthase. The *Chlorella* GMC oxidoreductases thus extend the pool of alkane-synthetizing enzymes and offers new possibilities for biotechnological applications.

The Algal Group of GMC Oxidoreductases

The GMC oxidoreductase family was first described in 1992. Comparison of protein sequence from glucose dehydrogenase, choline dehydrogenase, glucose oxidase and methanol oxidase from various organisms (respectively: *Drosophila melanogaster*, *Escherichia coli*, *Aspergillus niger*, and *Hansenula polymorpha*) showed low similarity but conserved motifs. These enzymes contain a flavoenzyme site and a canonical ADP-binding βαβ fold close to their amino termini. Structural studies confirm that these proteins are composed of an N-terminal FAD-binding domain, and a C-terminal substrate-binding domain. The FAD-binding domain forms the alpha-beta fold typical of dinucleotide binding proteins, while the substrate-binding domain consists of a beta sheet surrounded by alpha helices. The general topology of these proteins is conserved, though inserted structural elements occur in both choline dehydrogenase and alcohol dehydrogenase.

Members of the GMC oxidoreductase family catalyze diverse reactions, mostly oxidation of alcohols to aldehydes. This family includes glucose and methanol oxidases, fatty alcohol oxidase, choline dehydrogenase. But the family also includes a lyase from almond acting on hydroxymandelonitrile, which shows that the family harbors very diverse catalytic mechanisms. Strict dependence of the activity on light is likely to be mediated by the FAD cofactor found to be associated with the recombinant enzyme. Presence of FAD was consistent with the fact that the *Chlorella* enzyme has a FAD binding domain like all GMC oxidoreductases (FIG. 15).

Interestingly, all the microalgal species that have been shown to produce long or very long chain alka(e)nes have a homolog to the *Chlorella* GMC oxidoreductase, but the only species that has no detectable alka(e)nes (*Ostreococcus tauri*) has no GMC homolog. It seems thus very likely that the members of the algal group of GMC oxidoreductases are all alkane synthases. This idea is supported by the demonstration that the GMC oxidases from *Chlamydomonas reinhardtii* and *Phaeodactylum tricornutum* bear a fatty acid decarboxylase activity (FIG. 19).

Possible Biotechnological Applications of the Microalgal Alkane Synthase

The discovery of a microalgal pathway for alkane synthesis is of biotechnological interest because microalgae are promising platform for lipid production but harvest of biomass, extraction of oil and conversion to biodiesel is very costly. Production in microalgae of fuel-like volatile alkanes that could be easily recovered from the culture medium might thus circumvent these issues.

In vitro, the *Chlorella* enzyme is able to act on a variety of fatty acids, including medium chains (FIG. 10). The fact that the enzymes acts on free fatty acids is a clear advantage compared to the plant, cyanobacterial or insect enzymes acting on fatty aldehydes because these intermediates can be degraded by many endogenous reductases (Rodriguez & Atsumi, 2014, Metabolic Engineering, 25, 227-37). Also, free fatty acids can be generated by various types of lipases, some of which are highly active and can use a variety of lipid substrates (Andersson, 1996, Biochim Biophys Acta, 1302, 236-240). Increasing availability of free fatty acids by coexpression of a lipase boosts alkane production (FIG. 20). In *E. coli*, some tridecane is produced when the *Chlorella* GMC oxidoreductase is expressed (FIG. 6). This alkane is shorter than those observed in algae and is due to the presence in *E. coli* of a new substrate (myristic acid) for the enzyme. Accordingly, microalgal GMC oxidoreductases could be used to generate high amounts of medium to short chain alkanes, in particular when used together with a lipase in a microorganism that accumulates short to medium chain fatty acids.

As alkane synthase is a photoenzyme, light can be used to finely modulate alkane production in vitro and in vivo. First, presence or absence of photons from 320-540 can be used to select the moment of the alkane production. Second, light intensity can be used to increase or decrease the rate of alkane synthesis. Experiments were performed here under continuous light but it is possible that other conditions such flashes could be interesting for hydrocarbons synthesis.

Finally, products (alkanes and alkenes), coproduct ($CO_2$), and enzyme fluorescence can be used to estimate the concentration of free fatty acids in a sample (or total fatty acids if used in combination with a lipase).

Materials & Methods

Strains and Culture Conditions

*Chlamydomonas reinhardtii* wild-type strains CC124 (nit1 nit2; mt−) and CC125 (nit1 nit2; 415 mt+) were used. *Chlorella variabilis* NC64A was from the laboratory of J. L. Van Etten (University of Nebraska). All strains were grown routinely in conical flasks in incubation shakers at 25° C. (Infors HT) under air enriched with 2% (v/v) $CO_2$, with agitation at 140 rpm and light intensity at 120 μmol photons $m^{-2}s^{-1}$ for *Chlamydomonas* and 70 for *Chlorella*. *Chlamydomonas* and *Chlorella* were cultivated in Tris-Acetate-Phosphate (TAP) medium and minimal medium. Cells were routinely counted using a Multisizer™ 3 (Coulter).

Purification of Native Alkane Synthase

A Fast Protein Liquid Chromatography system (AKTA-purifier 900, GE Healthcare) was used. The alkane synthase activity assay is described in next section. *Chlorella* cells ($200.10^9$) were centrifuged for one hour at 6000 g and cell pellets were frozen in liquid nitrogen and stored for one hour at minus 80° C. Cells were resuspended in lysis buffer containing 20 mM Tris (pH 8.0), 100 mM NaCl and 1 mM EDTA (buffer A) and disrupted using a Cell Disruption (Constant) at 2 kbar pressure. Homogenate was centrifuged twice for 40 min at 50 000 g. Supernatant was collected and centrifuged for 90 min at 105 000 g. The resulting microsomal pellet was resuspended overnight at 4° C. under agitation in a buffer A added with 2.7 mM Triton X100. Ultracentrifugation was performed at 105 000 g for 90 min and the supernatant was loaded on a gel filtration column. Most active fractions were pooled, concentrated using a 30 kDa Amicon® ultracentrifugal filter and buffer was changed by dilution to a 20 mM Tris (pH 8.0), 50 mM NaCl, 1 mM EDTA, 0.05% (w/v) Triton X100 buffer (buffer B). The second purification step involved an anion exchange column (HiTrap Q FF, GE Healthcare). Proteins were eluted using a gradient (0-100%) of a buffer 20 mM Tris (pH 8.0), 1 M NaCl, 1 mM EDTA and 0.05% (w/v) Triton X100 (buffer C). Most active fractions were pooled, concentrated using a 30 kDa an Amicon® ultracentrifugal filter and buffer was changed by dilution to buffer B. The third purification step involved a strong anion exchange column (Mono Q GI, GE Healthcare). Proteins were eluted using a gradient of buffer C. Most active fractions were kept for proteomic analysis.

Activity Assay for Protein Purification

Enzymatic assays were performed in transparent glass vials sealed using caps with septum. Reaction mixtures contained 500 μL of each purification fraction, 200 μM of perdeuterated palmitic acid (10 mM stock solution in ethanol) and 45 nmol hexadecane as internal standard (4.5 mM stock solution in chloroform). Vials were agitated at 120 rpm overnight at 25° C. under a white light (intensity 120 μmol photons $m^{-2}s^{-1}$). Reaction was stopped by the addition of 10 μL NaOH 10 M through the septum using a syringe. Hydrocarbons produced were analyzed by incubating in the headspace of the vial a solid phase microextraction (SPME) fiber (DVB PDMS fused silica, 65 μm double-polar, Supelco) mounted on a holder. After 15 min incubation at room temperature the SPME fiber was immediately inserted into the injector of the GC-MS and desorbed at 250° C. GC-MS analysis was carried out as described below.

Proteomic Analysis

Protein preparation, in-gel digestion and nanoLC-MS/MS analyses were performed as previously described. In brief, proteins solubilized in Laemmli buffer were stacked on top of a 4-12% (w/v) NuPAGE gel (Invitrogen) and stained by R-250 Coomassie Blue (BioRad). Gel bands were then excised and proteins in-gel digested using trypsin (Promega). Resulting peptides were analysed by nanoliquid chromatography coupled to tandem mass spectrometry (Ultimate 3000 coupled to LTQ-Orbitrap Velos Pro, Thermo Scientific) using a 120 min gradient. Peptides and proteins were identified through concomitant searches against Uniprot (*Chlorella variabilis* taxonomy, September 2016 version), classical contaminants (homemade) and the corresponding reversed databases using Mascot (version 2.5.1). The Proline software was used to filter the results (conservation of rank 1 peptides, peptide identification FDR <1% as calculated on peptide scores by employing the reverse database⊠ strategy, peptide length ≥7, and minimum of 1 specific peptide per identified protein group) before performing a compilation, grouping and comparison of the protein groups from the different samples. Only proteins identified with a minimal specific spectral count of 2 were taken into account for further comparison.

Protein Analysis and Western Blots

Protein extracts were added with LDS NuPAGE loading dye 1× final, boiled for 10 min at 95° C., resolved using reducing 10% (w/v) SDS-PAGE with MOPS running buffer and stained with silver nitrate. For detection of His-tagged proteins, polypeptides resolved by SDS-PAGE were transferred onto a nitrocellulose membrane using a semi-dry blotting system, and His-tags were revealed using rabbit anti-His antibodies, horseradish peroxidase-conjugated anti-rabbit antibodies and ECL substrate (Amersham Biosciences).

Cloning of Alkane Synthase cDNA and Purification of Recombinant Alkane Synthase

Total RNAs were extracted from *Chlorella* cells by a phenol-chloroform method and cDNAs⊠ were synthesized using SuperScript® III reverse transcriptase. The cDNA encoding the GMC oxidoreductase was amplified using primers designed in putative 5' and 3'UTRs Primer forward: ATGGCGTCAATTACATCGCG (SEQ ID No 24); Primer reverse: TCATGCTGCCACTGTCGC (SEQ ID No 25), cloned into a TOPO XL plasmid and sequenced. The sequence corresponding to residues 62-654 of the Alkane synthase was amplified from a synthetic gene codon-optimized for E. coli expression using a primer forward 5'-CTG TAC TTC CAA TCA GCC AGC GCA GTT GAA GAT ATT C-3' (SEQ ID No 27) and a reverse primer: 5'-TAT CCA CCT TTA CTG TTA TCA TGC TGC AAC GGT TGC CGG TG-3' (SEQ ID No 28). and cloned into pLIC07 vector, which introduced downstream of the ATG start codon a cassette coding for a 6 His-tagged thioredoxin and a tobacco etch virus (TEV) protease-cleavage site. The recombinant alkane synthase was produced in BL21-CodonPlus (DE3)-RIL E. coli cells cultured in TB medium at 37° C. up to OD 0.9. At this stage, the temperature was decreased to 17° C. and the cells were grown for an additional 18 h. The cells were harvested by centrifugation (4000 g for 10 min) and the pellet was frozen. Cell pellet was resuspended in lysis buffer during 30 min at 4° C. (10 mL of lysis buffer for one liter of cells at OD=1). Lysis buffer contained 300 mM NaCl, 50 mM Tris pH 8.0, 10 mM imidazol, 5% (w/v) glycerol, 0.25 mg mL$^{-1}$ lysozyme, 20 mM MgSO$_4$, 10 µg mL$^{-1}$ DNase, and antiproteases. After resuspension, cells were lysed by sonication and centrifuged for 30 min at 8000 g. Supernatant was collected and enzyme was purified by FPLC. First purification was made on a nickel column and protein was eluted by a step gradient using 50% (v/v) of a second buffer containing 300 mM NaCl, 50 mM Tris pH 8.0, 500 mM imidazole 5% (w/v) glycerol. Tobacco etch virus protease (at 1 mg per 10 mg total protein) was used to cut off the His tag and the thioredoxin. A dialysis was performed overnight in the presence of TEV to change the buffer to a buffer containing 300 mM NaCl, 50 mM Tris pH 8.0, 10 mM imidazol, 5% (w/v) glycerol. A second FPLC chromatography using a nickel column was made to separate the protein from the His-tagged thioredoxin. The last purification step was a gel filtration column (Superdex200 26/600 mm GE Healthcare). Buffer used for this step contained 150 mM NaCl, 10 mM Tris pH 8.0, 5% (w/v) glycerol. The protein was concentrated using ultracentrifugal filters 50 kDa Amicon® and stored at −80° C. after adding 20% (w/v) glycerol.
Expression of Chlorella variabilis, Chlamydomonas reinhardtii and Phaeodactylum tricornutum GMC Oxidoreductase in E. coli.

Chlamydomonas reinhardtii and Phaeodactylum tricornutum Alkane synthase was amplified from a synthetic gene codon-optimized for E. coli using for Chlamydomonas reinhardtii a primer forward 5'-TAC TTC CAA TCA ATG ATG CTG GGT CCG AAA ACC-3' (SEQ ID No 29) and a primer reverse, 5'-TAT CCA CCT TTA CTG TTC TAC TAA ACT GCA ACC GGC TGA CG-3' (SEQ ID No 30). For Phaeodactylum tricornutum, forward primer 5'-TAC TTC CAA TCA ATG AAA AAA AGC CTG CGT AGC-3' (SEQ ID No 31), reverse primer 5'-TAT CCA CCT TTA CTG TTC TAC TAT GCG CTT GCG GTG-3' (SEQ ID No 32). Genes were cloned into pLIC07 vector, which introduced downstream of the ATG start codon a cassette coding for a 6 His-tagged thioredoxin and a tobacco etch virus (TEV) protease-cleavage site. E. coli strain expressing the GMC oxidase from Chlorella variabilis NC64A, Chlamydomonas reinhardtii or Phaeodactylum triconutum were grown at 37° C. with agitation at 180 rpm and light at 100 µmole.photon.m$^{-2}$·s$^{-1}$. When OD reached 0.6, 500 µM of isopropyl β-D-1-thiogalactopyranoside was added. Cells were then grown for 24 hours at 37° C., harvested, transmethylated using methanol added with 5% sulfuric acid and hydrocarbons were extracted with hexane and analyzed by GC-MS as previously described.
Co-Expression in E. coli of a GMC Oxidoreductase and a Lipase E. coli strain transformed with a vector expressing the GMC oxidase from Chlorella variabilis NC64A (or Chlamydomonas reinhardtii) and/or a vector expressing the lipase from the bacterium Staphylococcus hyicus, were grown in TB medium at 37° C. Expression was induced with 1 mM of isopropyl β-D-1-thiogalactopyranoside (added with 0.2% arabinose for co-expression). Cells were then grown overnight at 25° C. at 100 µmole.photon.m$^{-2}$·s$^{-1}$ and 6 h at 2000 µmole.photon.m$^{-2}$·s$^{-1}$. Cells were harvested (4 ml at OD=5), transmethylated using methanol added with 5% sulfuric acid and hydrocarbons were analyzed by SPME and GC-MS as previously described.
Enzymatic Assay with Purified Enzyme All assays were performed in transparent glass vials sealed using caps with septum. Optimum pH was determined using a Teorell Stenhagen universal buffer (33 mM citric acid monohydrate, 33 mM phosphoric acid, 100 mM NaOH, 16.7 mM of boric acid, pH 8.5 adjusted with 1N HCl). Other assays were performed in 100 mM Tris HCl pH 8.5, 100 mM NaCl. Reaction mixtures (500 µL) typically contained 160 nM purified enzyme (stock ⊠ solution 2.5 mg ml$^{-1}$) and 400 µM substrate (stock solution 10 mM in ethanol). In some assays, a lipase was used with the alkane synthase. In this case, substrate was a triacylglycerol. Generally, samples were shaken at 200 rpm during 15 min under LED-made white light at 2000 µmol⊠ photons m$^{-2}$s$^{-1}$. After the incubations, samples were heated at 95° C. during 15 min to stop the enzymatic reaction. Samples were cooled down and internal standard (hexadecane) was added (45 nmol from a 4.5 mM stock solution in chloroform). NaOH was then added to the reaction mixture (10 µL from a stock solution of 10 M) and samples were vortexed for 5 min. Then 250 µL of hexane was added and samples were vortexed for 5 min to extract alkanes and alkenes. The hexane phase was collected by centrifugation and analyzed by GC-MS-FID. The analysis was done by direct injection of 100 µl of the headspace into a GC-MS. In FIG. 11 activity on 1-$^{13}$C-palmitate was monitored by release of $^{13}CO_2$ using membrane inlet mass spectrometry. Illuminations were provided by CBT-120 LEDs (Luminous, Billerica) either blue (peak at 460 nm, 25 nm FWHM), or red (peak at 635 nm, 15 nm FWHM) at an intensity of 850 µmol photons m$^{-2}$ s$^{-1}$.
Fluorescence of the Alkane Synthase Enzyme was analyzed by UV-Vis spectroscopy (Uvikon XS spectrophotometer from Secomam). Absorbance spectrum was measured on purified enzyme in a buffer containing 100 mM tris pH 8.5 and 100 mM NaCl. Fluorescence spectrum (500 to 700 nm) was measured on a Varian Cary Eclipse using an excitation flux at 450 nm with a 10 nm slit For kinetic, fluorescence was measured at 540 nm using an excitation flux at 450 nm with a 10 nm slit.
Membrane Inlet Mass Spectrometry (MIMS)

Online measurements of $^{12}CO_2$ (m/z=44) and $^{13}CO_2$ (m/z=45) were monitored using mass spectrometry (model Prima B, Thermo Scientific). The membrane inlet system consists of a thermo-regulated oxygen electrode chamber (Hansa Tech), which is connected to the vacuum line of the mass spectrometer via a gas-permeable thin Teflon membrane (0.001 inch thickness, YSI Inc.), which seals the bottom of the chamber. For analyses, 20 µL of purified enzyme at 2.5 mg mL$^{-1}$ and 30 µL substrate at 10 mM in dimethylsulfoxide ($^{13}$C-palmitic acid) was added to 1.45 mL of Tris/Acetate/Borate buffer 100 mM, pH 6.5 containing NaCl 100 mM, placed into the measuring chamber, thermoregulated at 25° C., and stirred continuously. Gases dissolved in the medium diffuse through the Teflon membrane to the ion source of the mass spectrometer.

Cultures in Photobioreactors

*Chlamydomonas reinhardtii* CC124 (nit1 nit2; mt−) and *Chlamydomonas reinhardtii* overexpressing the alkane synthase gene were cultured in minimal medium (Harris, 1989) in one liter photobioreactors (BIOSTAT Aplus, Sartorius Stedim Biotech) operated as turbidostats. $A_{880}$ was measured continuously using a biomass probe (Excellprobe, Exner) and cultures were maintained at constant $A_{880}$ by injection of fresh medium. The pH was maintained at a constant value of 7 by injection of KOH (0.2 N) or HCl (0.2 N). The cultures were stirred using a metal propeller (250 rpm). The gas flow rate was adjusted to 0.5 L min$^{-1}$. Air enriched with 2% (v/v) $CO_2$ was generated using mass flow meters (EL flow, Bronkhorst). White light was supplied by eight fluorescent tubes (Osram Dulux L 18 W) placed radially around the photobioreactor. We used a blue filter (363 special medium blue, Lee filters, USA) and a red filter (113 magenta, Lee filters, USA) to provide respectively blue and red light. Both lights were at same intensity (35 µmol photons m$^{-2}$s$^{-1}$).

Transmethylation

To quantify hydrocarbons together with fatty acids, transmethylation of whole cells was used. Briefly, cell pellets (one hundred million cells for *Chlamydomonas*, two hundred million cells for *Chlorella variabilis* NC64A and 20 mL OD$^{-1}$ unit of *E. coli*) were added with 2 mL of a solution containing methanol with 5% (v/v) sulfuric acid and 25 µg of triheptadecanoate (from a stock solution 2.5 mg mL$^{-1}$ in chloroform) and 5 µg of 16:0-alkane (stock solution 1 mg mL$^{-1}$ in chloroform) were included as internal standards. Samples were incubated at 85° C. for 90 min in sealed glass tubes. After cooling down, FAMEs and hydrocarbons were extracted by adding 250 µL hexane and 500 µL NaCl 0.9% (w/v). Samples were vortexed for 10 min and the organic phase was separated from the aqueous phase by centrifugation at 3000 g for 2 min. The hexane phase was recovered and 1 µl was injected in the GC-MS/FID.

GC-MS Analyses

Analyses by gas chromatography coupled to mass spectrometry (GC-MS), which were performed after solid phase microextraction (SPME), were carried out using the following setup. A Thermo-Fischer gas chromatography Focus series coupled to a Thermo-Fischer DSQII mass spectrometer (simple quadrupole) was used with a DB-5HT (Agilent) apolar capillary column (length 30 m, internal diameter 0.25 mm, film thickness 0.1 µm). Helium carrier gas was at 1 mL min$^{-1}$. Oven temperature was programmed with an initial 2 min hold time at 50° C., then a ramp from 50° C. to 300° C. at 10° C. min$^{-1}$, and a final 3 min hold time at 300° C. Samples were injected in splitless mode (2 min) at 250° C. The MS was run in full scan over 40-500 amu (electron impact ionization, 70 eV) and peaks were quantified based on total ion current using the internal standards. For cosubstrate determination, a column HP-PLOT Q was used (0.32 mm diameter×30 m) and $CO_2$, $^{13}CO_2$ and argon were analysed using an oven temperature of 40° C. and single ion monitoring (m/z 40, 44, 45).

GC-MS/FID Analyses

Analyses by gas chromatography coupled to mass spectrometry and flame ionization detection (GC-MS/FID) were performed only after transmethylation reactions in order to quantify fatty acids and hydrocarbons together. Analyses were carried out on an Agilent 7890A gas chromatographer coupled to an Agilent 5975C mass spectrometer (simple quadrupole). A Zebron 7HG-G007-11 (Phenomenex) polar capillary column (length 30 m, internal diameter 0.25 mm, film thickness 0.25 µm) was used. Hydrogen carrier gas was at 1 mL min$^{-1}$. Oven temperature was programmed with an initial 2 min hold time at 60° C., a first ramp from 60° C. to 150° C. at 20° C. min$^{-1}$ with a 5 min hold time at 150° C., then a second ramp from 150° C. to 240° C. at 6° C. min$^{-1}$ and a final 3 min hold time at 240° C. Samples were injected in splitless mode (1 min) at 250° C. The MS was run in full scan over 40-350 amu (electron impact ionization at 70 eV) and peaks were quantified based on the FID signal using the internal standards.

Phylogeny

To build the phylogenetic tree, 56 amino acid sequences of GMC oxidoreductases from prokaryotes and eukaryotes were retrieved from Cyanobase (see Worldwide Web site: genome.kazusa.or.jp/cyanobase/), NCBI (see Worldwide Web site: ncbi.nlm.nih.gov/), Phytozome (see Worldwide Web site: phytozome.Jgi.doe.gov) or Cyanidioschyzon merolae see Worldwide Website: merolae.biol.s.u-tokyo-.ac.jp/). Sequences were aligned with the MAFFT version 7 program. The resulting alignment was manually refined using SeaView version 4 and regions where homology was doubtful were removed from further analysis. A total of 266 amino acids positions were kept for the phylogenetic analysis. The tree was obtained using Neighbor-Joining (NJ), approaches in the Phylogenetic Inference Package Phylip version 3.69. The PROTDIST program was used to create distance matrices. The NEIGHBOR program was used for NJ analysis and the sequence input order was randomized (20 jumbles). The SEQBOOT and CONSENSE programs were used for bootstrap value calculations on 100 replications and consensus tree reconstructions, respectively. The phylogenetic trees were drawn with Dendroscope version 3.

The invention claimed is:

1. A method for producing alkanes and/or alkenes from fatty acids comprising contacting a polypeptide having fatty acid decarboxylase activity, comprising a sequence having at least 80% sequence identity with one of SEQ ID NOs: 1-3 or 5-8 with fatty acids having from 12 to 18 carbon atoms in length and in the presence of light having a wavelength between 300 and 540 nm, the polypeptide also comprising a FAD binding domain and the consensus sequence G-X-L-$(X)_4$-C-[D/E]-X-G-[A/G]-F-X-[K/R] (SEQ ID NO: 4), X being any amino acid, said fatty acids being optionally substituted with at least one hydroxyl group or methyl group.

2. The method according to claim 1, wherein the polypeptide comprises the consensus sequence G-$X_1$-L-$(X)_4$-C-[D/E]-$X_2$-G-[A/G]-F-$X_3$-[K/R] (SEQ ID NO: 4), wherein
$X_1$ is selected from the group consisting of P, L and G;
$(X)_4$ is [T/A]-[T/S/C]-[P/T/A]-[G/A];
$X_2$ is selected from the group consisting of H, N and R; and
$X_3$ is selected from the group consisting of L, V A and F.

3. The method according to claim 1, wherein positions C372, R391, Y406, Q426, H512 and N515, corresponding to the amino acid numbering of SEQ ID NO: 1, are conserved.

4. The method according to claim 1, wherein the polypeptide having fatty acid decarboxylase activity comprises a region forming a hydrophobic tunnel in which the fatty acid can enter and wherein at least 40% of the amino acid residues between positions 388-428, corresponding to the amino acid numbering of SEQ ID NO: 1, are hydrophobic residues selected from the groups consisting of V, I, L, M, F, W, C, A and Y.

5. The method according to claim 1, wherein the polypeptide comprises SEQ ID NOs: 1, 2, 3, 5, 6, 7, or 8.

6. The method according to claim 1, wherein the polypeptide is algal.

7. The method according to claim 1, wherein the fatty acid is selected from saturated and unsaturated fatty acids having 12 to 18 carbon atoms in length substituted with at least one hydroxyl group or methyl group.

8. The method according to claim 1, wherein the light has a wavelength between 400 and 520 nm.

9. A method for producing alkanes and/or alkenes from fatty acids, wherein a recombinant host cell expressing a polypeptide having at least 80% identity with one of SEQ ID NOs: 1, 2, 3, 5, 6, 7 or 8, the polypeptide also comprising a FAD binding domain and the consensus sequence G-X-L-$(X)_4$-C-[D/E]-X-G-[A/G]-F-X-[K/R] (SEQ ID NO: 4), X being any amino acid, is cultured and alkanes and/or alkenes are recovered.

10. The method of claim 9, wherein the host cell further expresses a lipase.

11. The method of claim 1, wherein the polypeptide having fatty acid decarboxylase activity is from an algae species.

12. A method for producing alkanes and/or alkenes from fatty acids comprising contacting a polypeptide having fatty acid decarboxylase activity with fatty acids and light with a wavelength between 300 and 540 nm, wherein the polypeptide having fatty acid decarboxylase comprises a sequence having at least 85% identity with a sequence selected from the group consisting of SEQ ID NO: 1, SEQ ID NO: 2, SEQ ID NO: 3, SEQ ID NO: 5, SEQ ID NO: 6, SEQ ID NO: 7, and SEQ ID NO: 8 and wherein the fatty acids and the corresponding decarboxylated alkanes and/or alkenes have from 12 to 18 carbon atoms in length, said fatty acids being optionally substituted with at least one hydroxyl group or methyl group.

13. The method of claim 12, wherein the fatty acids are selected from saturated and unsaturated fatty acids having 12 to 18 atom carbons in length substituted with at least one hydroxyl group or methyl group.

14. The method of claim 12, wherein the polypeptide having fatty acid decarboxylase comprises a sequence having at least 90% identity with a sequence selected from the group consisting of SEQ ID NO: 1, SEQ ID NO: 2, SEQ ID NO: 3, SEQ ID NO: 5, SEQ ID NO: 6, SEQ ID NO: 7, and SEQ ID NO: 8.

15. The method of claim 12, wherein the polypeptide having fatty acid decarboxylase activity comprises a sequence having at least 95% sequence identity with a sequence selected from the group consisting of SEQ ID NO: 1, SEQ ID NO: 2, SEQ ID NO: 3, SEQ ID NO: 5 and SEQ ID NO: 6.

16. The method of claim 9, wherein the polypeptide having fatty acid decarboxylase comprises a sequence having at least 80% identity with a sequence selected from the group consisting of SEQ ID NO: 1, SEQ ID NO: 2, SEQ ID NO: 3, SEQ ID NO: 5, and SEQ ID NO: 6 and wherein the recovered alkanes and/or alkenes have 12 to 18 carbon atoms in length, are optionally substituted with at least one hydroxyl group or methyl group, and optionally have an unsaturation.

17. The method of claim 1, wherein the polypeptide has a sequence having at least 80% identity with a sequence selected from SEQ ID NO: 1, SEQ ID NO: 2, SEQ ID NO: 3, SEQ ID NO: 5, and SEQ ID NO: 6.

18. The method of claim 1, wherein the polypeptide has a sequence having at least 80% identity with a sequence selected from SEQ ID NO: 1, SEQ ID NO: 2, and SEQ ID NO: 3.

* * * * *

UNITED STATES PATENT AND TRADEMARK OFFICE
CERTIFICATE OF CORRECTION

PATENT NO. : 11,236,367 B2
APPLICATION NO. : 16/302112
DATED : February 1, 2022
INVENTOR(S) : Frédéric Beisson et al.

It is certified that error appears in the above-identified patent and that said Letters Patent is hereby corrected as shown below:

In the Specification

Column 5,
Line 23, "ettings" should read --settings--.

Signed and Sealed this
Fourth Day of October, 2022

Katherine Kelly Vidal
*Director of the United States Patent and Trademark Office*